(12) United States Patent
Lee et al.

(10) Patent No.: US 10,615,347 B2
(45) Date of Patent: Apr. 7, 2020

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG DISPLAY CO., LTD., Seoul (KR)

(72) Inventors: Seung-Jae Lee, Paju-si (KR); Jong-Kwan Bin, Paju-si (KR); Bo-Min Seo, Paju-si (KR); Hye-Ock Choi, Hwaseong-si (KR)

(73) Assignee: LG DISPLAY CO., LTD., Seoul (KR)

( * ) Notice: Subject to any disclaimer, the term of this patent is extended or adjusted under 35 U.S.C. 154(b) by 188 days.

(21) Appl. No.: 15/718,980

(22) Filed: Sep. 28, 2017

(65) Prior Publication Data

US 2018/0097184 A1 Apr. 5, 2018

(30) Foreign Application Priority Data

Sep. 30, 2016 (KR) .................. 10-2016-0126656

(51) Int. Cl.
*H01L 51/00* (2006.01)
*C07D 213/38* (2006.01)
(Continued)

(52) U.S. Cl.
CPC ........ *H01L 51/0061* (2013.01); *C07D 213/38* (2013.01); *C07D 239/26* (2013.01); *C07D 251/24* (2013.01); *C07D 401/12* (2013.01); *C07D 405/12* (2013.01); *C07D 409/12* (2013.01); *H01L 27/3244* (2013.01); *H01L 51/006* (2013.01); *H01L 51/0052* (2013.01); *H01L 51/0059* (2013.01);
(Continued)

(58) Field of Classification Search
None
See application file for complete search history.

(56) References Cited

U.S. PATENT DOCUMENTS 8,586,206 B2 * 11/2013 Kato .................... C07D 209/82
257/40
2011/0210318 A1 * 9/2011 Bae ...................... C07D 209/80
257/40

(Continued)

FOREIGN PATENT DOCUMENTS

CN 103137879 A 6/2013
CN 104347807 A 2/2015

(Continued)

*Primary Examiner* — Robert S Loewe
(74) *Attorney, Agent, or Firm* — Birch, Stewart, Kolasch & Birch, LLP

(57) ABSTRACT

The present invention provides an organic compound for an organic light emitting diode. The organic compound is represented by:

$$\begin{array}{c} X_4{-}X_5 \\ \| \\ X_3 \\ \| \\ X_2{=}X_1 \end{array} {-}L_1{-}N \begin{array}{c} (L_3)_n{-}A_2 \\ \\ (L_2)_m{-}A_1 \end{array}$$

The organic compound is capable of reducing a driving voltage of an organic light emitting diode by an excellent charge transporting property. The present invention also provides an organic light emitting diode and an organic light emitting display device including the organic compound.

17 Claims, 17 Drawing Sheets

(51) Int. Cl.

| | |
|---|---|
| C07D 239/26 | (2006.01) |
| C07D 251/24 | (2006.01) |
| C07D 401/12 | (2006.01) |
| C07D 405/12 | (2006.01) |
| C07D 409/12 | (2006.01) |
| H01L 27/32 | (2006.01) |
| H01L 51/52 | (2006.01) |
| H01L 51/50 | (2006.01) |

(52) U.S. Cl.
CPC ...... *H01L 51/0067* (2013.01); *H01L 51/0072* (2013.01); *H01L 51/0073* (2013.01); *H01L 51/0074* (2013.01); *H01L 51/0058* (2013.01); *H01L 51/506* (2013.01); *H01L 51/5056* (2013.01); *H01L 51/5064* (2013.01); *H01L 51/5072* (2013.01); *H01L 51/5088* (2013.01); *H01L 51/5092* (2013.01); *H01L 51/5096* (2013.01); *H01L 51/5278* (2013.01)

(56) References Cited

U.S. PATENT DOCUMENTS

| | | | | |
|---|---|---|---|---|
| 2012/0330025 | A1* | 12/2012 | Osaka | C07D 235/18 548/219 |
| 2013/0001526 | A1* | 1/2013 | Kwak | H01L 51/5265 257/40 |
| 2013/0032788 | A1* | 2/2013 | Lee | C07D 403/12 257/40 |
| 2013/0105771 | A1* | 5/2013 | Ryu | C09K 11/06 257/40 |
| 2013/0140530 | A1* | 6/2013 | Kho | H01L 51/006 257/40 |
| 2013/0153865 | A1* | 6/2013 | Kho | H01L 51/006 257/40 |
| 2013/0187137 | A1* | 7/2013 | Mizuki | C07C 211/54 257/40 |
| 2013/0200338 | A1* | 8/2013 | Kim | C07D 213/74 257/40 |
| 2014/0001444 | A1* | 1/2014 | Kim | H01L 51/5064 257/40 |
| 2014/0295058 | A1* | 10/2014 | Kitamura | G01N 21/95 427/8 |
| 2014/0374713 | A1* | 12/2014 | Cho | H01L 51/5004 257/40 |
| 2016/0099421 | A1* | 4/2016 | Kim | H01L 51/0067 257/40 |
| 2016/0118595 | A1* | 4/2016 | Itoi | H01L 51/0062 257/40 |
| 2016/0181524 | A1* | 6/2016 | Lee | H01L 51/006 257/40 |
| 2017/0244047 | A1* | 8/2017 | Lee | C07D 209/82 |
| 2017/0331039 | A1* | 11/2017 | Lim | H01L 51/0072 |

FOREIGN PATENT DOCUMENTS

| | | | | |
|---|---|---|---|---|
| CN | 105720203 A | 6/2016 | | |
| KR | 20140063428 A | * 5/2014 | ............ | H01L 51/50 |
| WO | WO 2014/030921 A1 | 2/2014 | | |

* cited by examiner

ORGANIC COMPOUND, AND ORGANIC LIGHT EMITTING DIODE AND ORGANIC LIGHT EMITTING DISPLAY DEVICE INCLUDING THE SAME

CROSS REFERENCE TO RELATED APPLICATIONS

The present application claims the priority benefit of Korean Patent Application No. 10-2016-0126656 filed in the Republic of Korea on Sep. 30, 2016, which is hereby incorporated by reference into the present application.

BACKGROUND OF THE INVENTION

Field of the Invention

The present invention relates to an organic compound. More particularly, the present invention relates to an organic compound capable of reducing a driving voltage of an organic light emitting diode by an excellent charge transporting property, and the organic light emitting diode and the organic light emitting display device including the organic compound.

Discussion of the Related Art

As recent requirements of a flat panel display device having a small occupied area have increased, an organic light emitting display (OLED) device including an organic light emitting diode have been developed. The OLED device may be referred to as an organic electroluminescent device (OELD).

The organic light emitting diode emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. The OLED device can be operated at a voltage (e.g., 10V or below) lower than a voltage required to operate other display devices. Moreover, the OLED device has an excellent color purity.

An organic emitting layer of the OLED device may have a single-layered structure of an emitting material layer (EML). Alternatively, to improve an emitting efficiency, the organic emitting layer may have a multi-layered structure. For example, the organic emitting layer may include a hole injection layer (HIL), a hole transporting layer (HTL), the EML, an electron transporting layer (ETL) and an electron injection layer (EIL).

To further improve the property or characteristic of the organic light emitting diode, a white emitting diode including at least two stacks is introduced. It may be referred to as a tandem structure organic light emitting diode. The tandem structure organic light emitting diode includes a charge generation layer (CGL) between adjacent stacks.

The organic materials used for the organic light emitting diode may be classified into an emitting material and a charge transporting material. In addition, the charge transporting material may be classified into a hole injection material, a hole transporting material, an electron transporting material and an electron injection material. Since high driving voltage and high current density in the organic light emitting diode may provide strong stress on the organic materials, there are bad effect on the stability and the lifetime.

The research for increasing the efficiency of the organic light emitting diode and reducing the power consumption of the organic light emitting diode by controlling an energy level of the charge transporting layer and/or the charge injection layer has been carried out. For example, Korean Patent Publication No. 2015-0026463 discloses the lifetime of the organic light emitting diode may be improved by using a charge transporting material having a vinyl end-group to decrease thermal degradation and prevent a pixel contraction.

However, a charge transporting material being capable of improving the current density, the lifetime and the emitting efficiency and decreasing the driving voltage and the stress to the organic light emitting diode is still required.

SUMMARY OF THE INVENTION

Accordingly, an embodiment of the present invention is directed to an organic compound, an organic light emitting diode and an organic light emitting display (OLED) device including the same that substantially obviates one or more of the problems due to limitations and disadvantages of the related art.

An object of the present invention is to provide an organic compound having an excellent hole transporting property and a charge generation property.

Another object of the present invention is to provide an organic light emitting diode and an OLED device having advantages in the driving voltage and the lifetime.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, an organic compound is represented by following Formula:

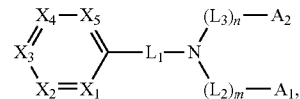

each of $X_1$ to $X_5$ is independently CR or N, and at least one of $X_1$ to $X_5$ is N, wherein R is selected from the group consisting of hydrogen, deuterium, tritium, hydroxyl group, cyano group, nitro group, $C_1$ to $C_{20}$ alkylhalide group, halogen, substituted or non-substituted $C_1$ to $C_{20}$ alkyl group, substituted or non-substituted $C_1$ to $C_{20}$ alkoxy group, substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, substituted or non-substituted $C_6$ to $C_{30}$ aryloxyl group, substituted or non-substituted $C_6$ to $C_{30}$ hetero-aryloxyl group, substituted or non-substituted $C_1$ to $C_{20}$ alkylamine group, substituted or non-substituted $C_5$ to $C_{30}$ arylamine group, substituted or non-substituted $C_5$ to $C_{30}$ hetero-arylamine group, substituted or non-substituted $C_1$ to $C_{30}$ alkylsilyl group, substituted or non-substituted $C_5$ to $C_{30}$ arylsilyl group and substituted or non-substituted $C_5$ to $C_{30}$ hetero-arylsilyl group, wherein each of $A_1$ and $A_2$ is independently selected from the group consisting of substituted or non-substituted $C_1$ to $C_{20}$ alkyl group, substituted or non-substituted $C_1$ to $C_{20}$ alkoxy group, substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, substituted or non-substituted $C_6$ to $C_{30}$ aryloxyl group, substituted or non-substituted $C_6$ to $C_{30}$ hetero-aryloxyl group, substituted or non-substituted $C_1$ to $C_{20}$ alkylamine group, substituted or non-substituted $C_5$ to $C_{30}$ arylamine group and substituted or non-substituted $C_5$ to $C_{30}$ hetero-arylamine group, and wherein each of $L_1$ to $L_3$ is independently selected from the group of consisting substituted or non-substituted $C_5$ to $C_{30}$ arylene group, substituted or non-substituted $C_5$ to $C_{30}$ heteroarylene group, substituted or non-substituted $C_6$ to $C_{30}$ arylalkylene group, substituted or non-substituted $C_6$ to $C_{30}$ hetero-arylalkylene group, substituted or non-substituted $C_6$ to $C_{30}$ aryloxylene group and substituted or non-substituted $C_6$ to $C_{30}$ hetero-aryloxylene group, and each of "m" and "n" is 0 or 1.

In another aspect, an organic light emitting diode comprises a first electrode; a second electrode facing the first electrode; and an emitting part between the first and second electrodes and including an emitting material layer and an organic layer, wherein the organic layer includes the above organic compound.

In another aspect, an organic light emitting diode comprises first and second electrodes facing each other; a first emitting part between the first and second electrodes and including a first emitting material layer; a second emitting part between the first emitting part and the second electrode and including a second emitting material layer; and a P-type charge generation layer between the first and second emitting parts, wherein the P-type charge generation layer includes the above organic compound.

In another aspect, an organic light emitting diode comprises first and second electrodes facing each other; a first emitting part between the first and second electrodes and including a first emitting material layer; a second emitting part between the first emitting part and the second electrode and including a second emitting material layer; and a charge generation layer between the first and second emitting parts, wherein the second emitting part further includes an electron blocking layer between the charge generation layer and the second emitting part and includes the above organic compound.

In another aspect, an organic light emitting display device comprises a substrate; the above organic light emitting diode: and a thin film transistor between the substrate and the organic light emitting diode and connected to the organic light emitting diode.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Figure 1:
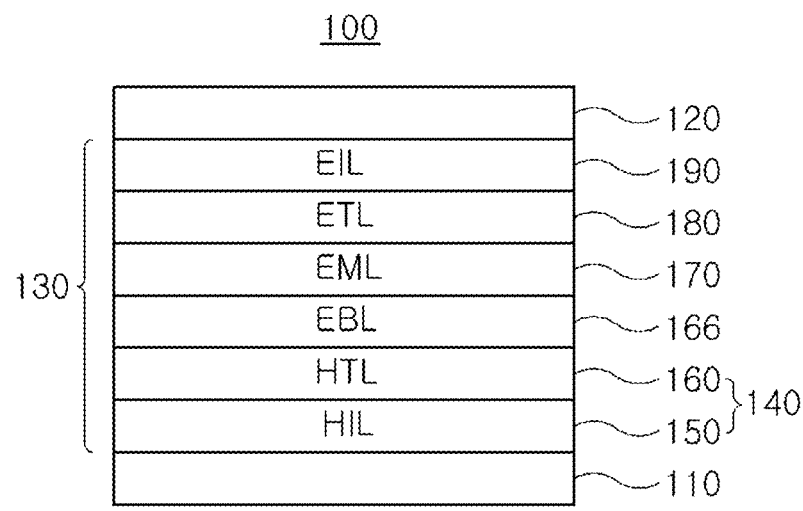
FIG. 1 is a schematic cross-sectional view of an organic light emitting diode according to a first embodiment of the present invention.

Reference will now be made in detail to the preferred embodiments, examples of which are illustrated in the accompanying drawings.

In an embodiment of the present invention, an organic compound includes an arylamine moiety and a hetero-aromatic moiety connected (or linked) to a nitrogen atom of the arylamine moiety. The organic compound is represented in Formula 1.

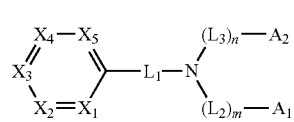

[Formula 1]

In Formula 1, each of $X_1$ to $X_5$ is independently CR or N, and at least one of $X_1$ to $X_5$ is N. R is selected from the group consisting of hydrogen, deuterium, tritium, hydroxyl group, cyano group, nitro group, $C_1$ to $C_{20}$ alkylhalide group, halogen, substituted or non-substituted $C_1$ to $C_{20}$ alkyl group, substituted or non-substituted $C_1$ to $C_{20}$ alkoxy group, substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, substituted or non-substituted $C_6$ to $C_{30}$ aryloxyl group, substituted or non-substituted $C_6$ to $C_{30}$ hetero-aryloxyl group, substituted or non-substituted $C_1$ to $C_{20}$ alkylamine group, substituted or non-substituted $C_5$ to $C_{30}$ arylamine group, substituted or non-substituted $C_5$ to $C_{30}$ hetero-arylamine group, substituted or non-substituted $C_1$ to $C_{30}$ alkylsilyl group, substituted or non-substituted $C_5$ to $C_{30}$ arylsilyl group and substituted or non-substituted $C_5$ to $C_{30}$ hetero-arylsilyl group.

Each of $A_1$ and $A_2$ is independently selected from the group consisting of substituted or non-substituted $C_1$ to $C_{20}$ alkyl group, substituted or non-substituted $C_1$ to $C_{20}$ alkoxy group, substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, substituted or non-substituted $C_5$ to $C_{30}$ aryloxyl group, substituted or non-substituted $C_5$ to $C_{30}$ hetero-aryloxyl group, substituted or non-substituted $C_1$ to $C_{20}$ alkylamine group, substituted or non-substituted $C_5$ to $C_{30}$ arylamine group and substituted or non-substituted $C_5$ to $C_{30}$ hetero-arylamine group.

Each of $L_1$ to $L_3$ is independently selected from the group consisting of substituted or non-substituted $C_5$ to $C_{30}$ arylene group, substituted or non-substituted $C_5$ to $C_{30}$ heteroarylene group, substituted or non-substituted $C_6$ to $C_{30}$ arylalkylene group, substituted or non-substituted $C_6$ to $C_{30}$ hetero-arylalkylene group, substituted or non-substituted $C_6$ to $C_{30}$ aryloxylene group and substituted or non-substituted $C_6$ to $C_{30}$ hetero-aryloxylene group, and each of "m" and "n" is 0 (zero) or 1.

In the term of "substituted", the substituent may include halogen-substituted or non-substituted alkyl group, halogen-substituted or non-substituted alkoxy group, halogen, cyano group, carboxyl group, carbonyl group, amino group, alkylamino group, nitro group, hydroxyl group, sulfonate group, alkyl silyl group, alkoxy silyl group, cycloakyl silyl group, aryl silyl group, substituted or non-substituted aryl group or heteroaryl group, but it is not limited thereto.

The term of "hetero", which is used in heteroaryl, heteroarylene, and so on, means that at least one carbon atom in the aromatic ring or alicyclic ring is substituted by a heteroatom being selected from the group consisting of nitrogen atom (N), oxygen atom (O) and sulfur atom (S).

When each of $A_1$ and $A_2$ is an aromatic ring and some of $X_1$ to $X_5$ is CR, each of the fused ring of $A_1$ and $A_2$ and R may independently be fused or non-fused homo-aromatic ring, such as phenyl, biphenyl, terphenyl, tetraphenyl, naphtyl, anthracenyl, indenyl, phenalenyl, phenanthrenyl, azulenyl, pyrenyl, fluorenyl, tetracenyl, indacenyl or spiro-fluorenyl, or fused or non-fused hetero-aromatic ring, such as pyrrolyl, pyridyl (or pyridinyl), pyrimidyl (pyrimidinyl), pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, quinolinyl, isoquinolinyl, phthalazinyl, quinoxalinyl, cinnolinyl, quinazolinyl, benzoquinolinyl, benzo iso-quinolinyl, benzoquinazolinyl, benzoquinoxalinyl, acrydinyl, phenanthrolinyl, furanyl, pyranyl, oxazinyl, oxazolyl, oxadiazolyl, triazolyl, dioxynyl, benzofuranyl, dibenzofuranyl, thiopyranyl, thiazinyl, thiophenyl or N-substituted spiro-fluorenyl.

For example, each of $A_1$ and $A_2$ may be selected from the group consisting of phenyl, biphenyl, terphenyl, where each benzene ring is connected in a meta-position or a para-position, fluorenyl, benzothiophenyl, dibenzothiophenyl, benzofuranyl, dibenzofuranyl, pyrrolyl, pyridinyl, pyrimidinyl, pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, quinolinyl, isoquinolinyl, phthalazinyl, quinoxalinyl, cinnolinyl, quinazolinyl, benzoquinolinyl, benzo iso-quinolinyl, benzoquinazolinyl and benzoquinoxalinyl.

Each of $L_1$ to $L_3$ may be an aromatic linker. For example, each of $L_1$ to $L_3$ may be selected from the group consisting of phenylene, biphenylene, terphenylene, tetraphenylene, indenylene, naphthylene, azulenylene, indacenylene, acenaphthenylene, fluorenylene, spiro-fluorenylene, phenalenylene, phenanthrenylene, anthracenylene, fluoranthrenylene, triphenylenylene, pyrenylene, chrysenylene, naphthacenylene, picenylene, perylenylene, pentaphenylene, hexacenylene, pyrrolylene, imidazolylene, pyrazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, benzo-isoquinolinylene, benzoquinazolinylene, benzoquinoxalinylene, cinnolinylene, phenanthridinylene, acridinylene, phenanthrolinylene, phenazinylene, benzoxazolylene, benzimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazolylene, triazinylene, dibenzofuranylene, dibenzothiophenylene, carbazolylene, benzocarbazolylene, dibenzocarbazolylene, indolocarbazolylene, indenocarbazolylene, imidazopyrimidinylene and imidazopyridinylene.

When the number of rings of $L_1$ and $L_2$ is increased, the conjugation length of the organic compound is increased such that the energy band gap of the organic compound is decreased. Accordingly, the number of rings of $L_1$ and $L_2$ may be 1 or 2, and beneficially 1. To improve the electron injection/transporting property of the organic compound, $L_1$ and $L_2$ may be 5-numbered atom ring to 7-numbered atom ring, and beneficially 6-numbered atom ring. In this instance, each of $L_1$ and $L_2$ may be phenylene, pyrrolylene, imidazolylene, pyrazolylene, pyrazinylene, pyrimidinylene, pyridazinylene, furanylene or thiophenylene, but it is not limited thereto.

The organic compound in Formula 1 has excellent properties, including the hole transporting property, the emitting efficiency and the color purity. When the organic compound is included in the organic layer of an organic light emitting diode, the hole transporting efficiency in the organic light emitting diode is improved such that there is an advantage in the driving voltage. In addition, since the balance of the hole and the electron in the organic light emitting diode is improved, the emitting efficiency is increased.

In an embodiment of the present invention, the organic compound includes an arylamine moiety and a heteroaromatic moiety directly or indirectly connected to a nitrogen atom of the arylamine moiety. The organic compound may be used for the hole auxiliary layer and/or an electron blocking layer. Due to the organic compound, the hole is efficiently injected and/or transported, and the electron migration to the anode is blocked.

In addition, when the organic compound, which has excellent hole transporting property, is used for the charge generation layer with a dopant having the deep lowest unoccupied molecular orbital (LUMO), the electron is migrated toward the anode and the hole migrated toward the cathode. Namely, the charge generation property is provided by the organic compound.

Namely, the organic compound singly or in combination with the dopant is used for an organic layer, e.g., a hole auxiliary layer such as a hole transporting layer or a hole injection layer, an electron blocking layer and a p-type charge transporting layer.

The organic compound, which includes an arylamine moiety and a pyridine moiety connected to a nitrogen atom of the arylamine moiety via a phenelene linker, may be represented in one of Formulas 2a to 2c.

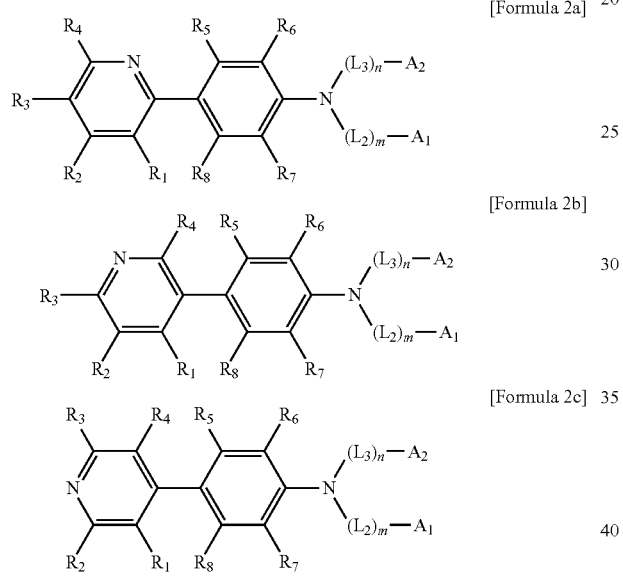

[Formula 2a]

[Formula 2b]

[Formula 2c]

In Formulas 2a to 2c, each of $R_1$ to $R_8$ may be independently selected from the group consisting of hydrogen, deuterium, tritium, hydroxyl group, cyano group, nitro group, $C_1$ to $C_{20}$ alkylhalide group, halogen, substituted or non-substituted $C_1$ to $C_{20}$ alkyl group, substituted or non-substituted $C_1$ to $C_{20}$ alkoxy group, substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, substituted or non-substituted $C_6$ to $C_{30}$ aryloxyl group, substituted or non-substituted $C_6$ to $C_{30}$ hetero-aryloxyl group, substituted or non-substituted $C_1$ to $C_{20}$ alkylamine group, substituted or non-substituted $C_5$ to $C_{30}$ arylamine group, substituted or non-substituted $C_5$ to $C_{30}$ hetero-arylamine group, substituted or non-substituted $C_1$ to $C_{30}$ alkylsilyl group, substituted or non-substituted $C_5$ to $C_{30}$ arylsilyl group and substituted or non-substituted $C_5$ to $C_{30}$ hetero-arylsilyl group. $A_1$, $A_2$, $L_2$, $L_3$, m and n are same as defined in Formula 1.

On the other hand, the organic compound, which includes an arylamine moiety and a hetero-aromatic moiety connected to a nitrogen atom of the arylamine moiety via a phenelene linker, may be represented in one of Formula 3.

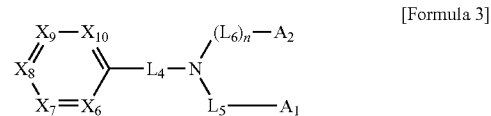

[Formula 3]

In Formula 3, one of $X_6$ to $X_{10}$ is N, and the rest of $X_6$ to $X_{10}$ is CR. R, $A_1$, $A_2$, n are same as defined in Formula 1. Each of $L_4$ to $L_6$ is substituted or non-substituted phenylene.

The organic compound of the present invention may be one of the materials in Formula 4.

[Formula 4]

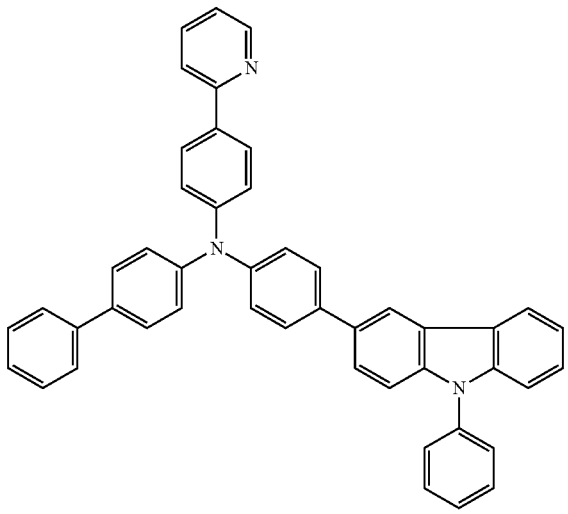

H-01

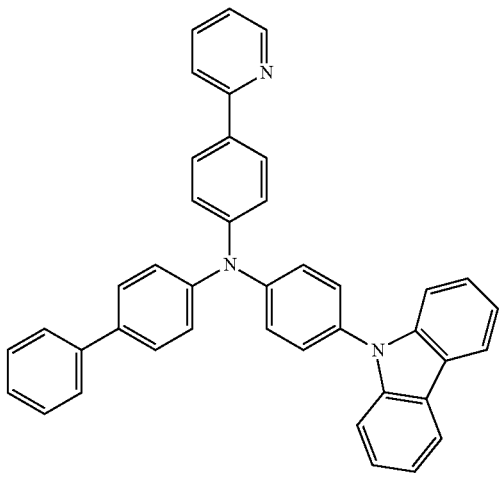

H-02

H-03
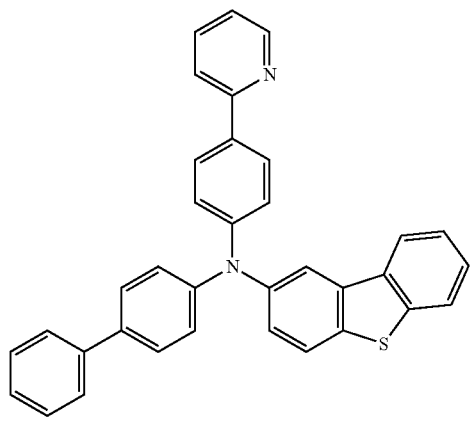
H-06
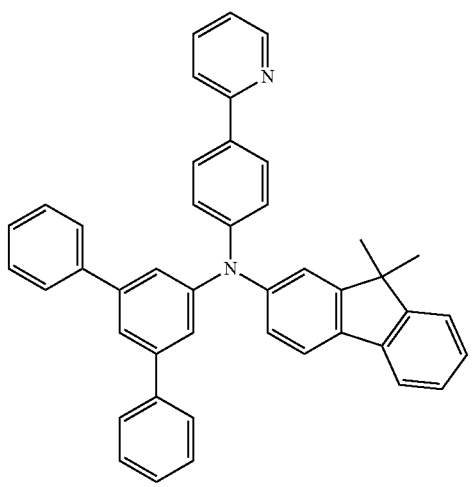
H-04
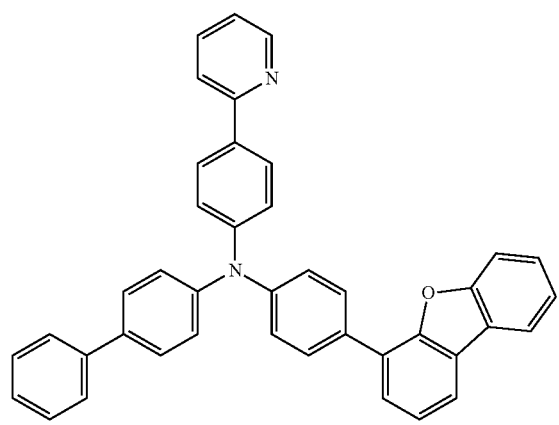
H-07
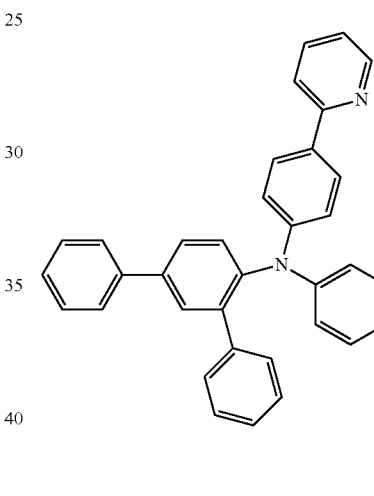
H-05
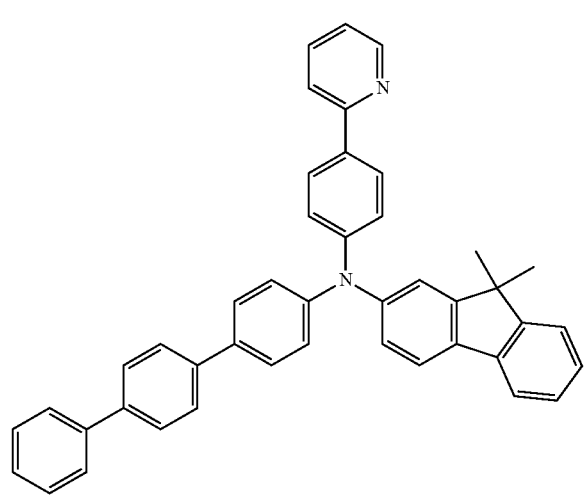
H-08
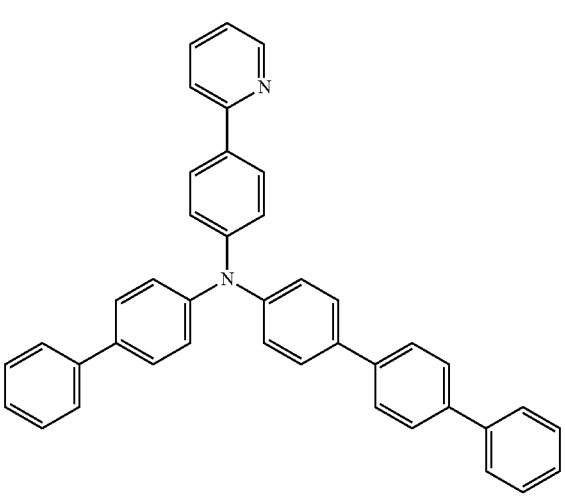

H-09
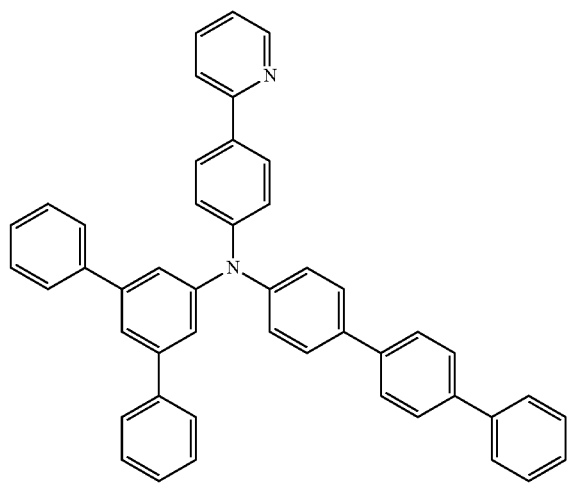
H-10
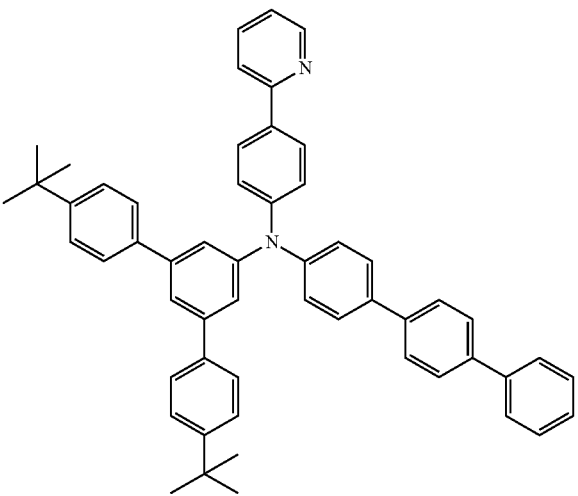
H-11
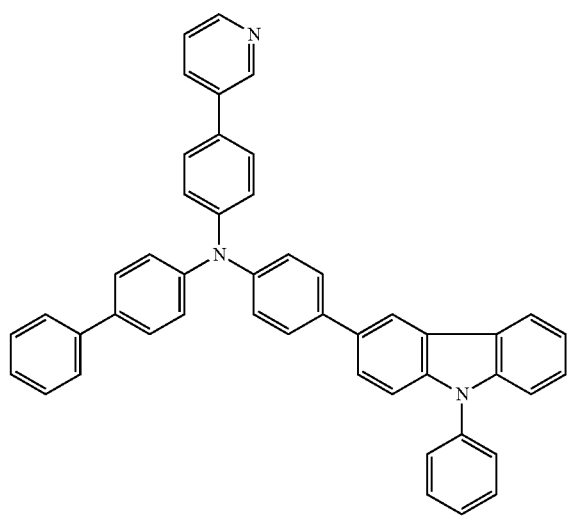
H-12
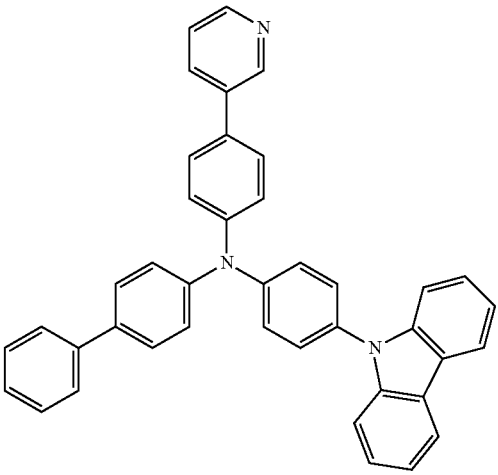
H-13
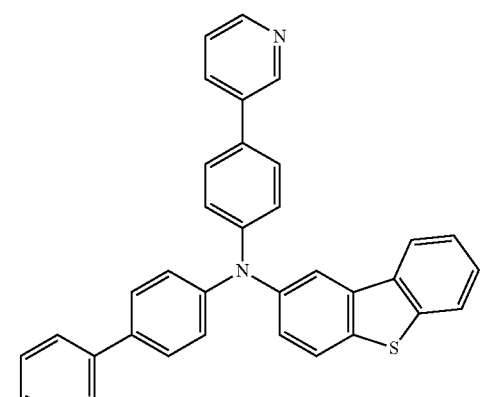
H-14
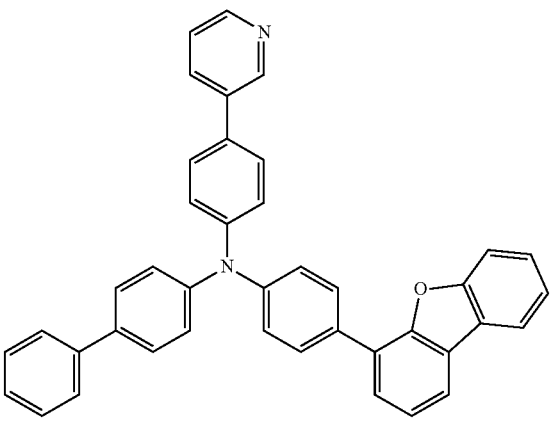

H-15
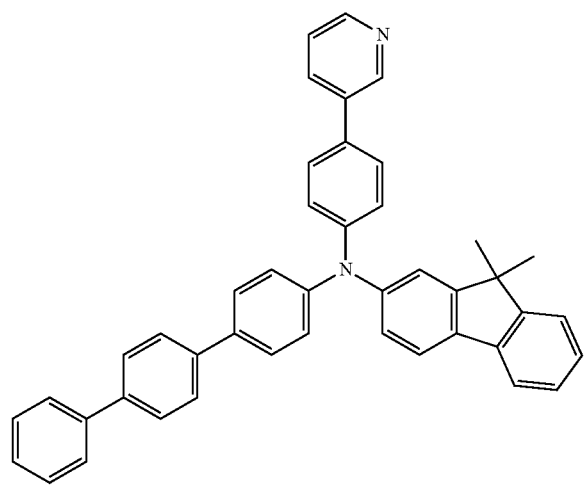
H-16
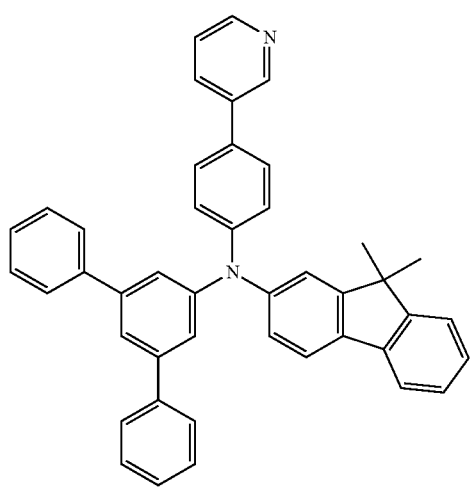
H-17
H-18
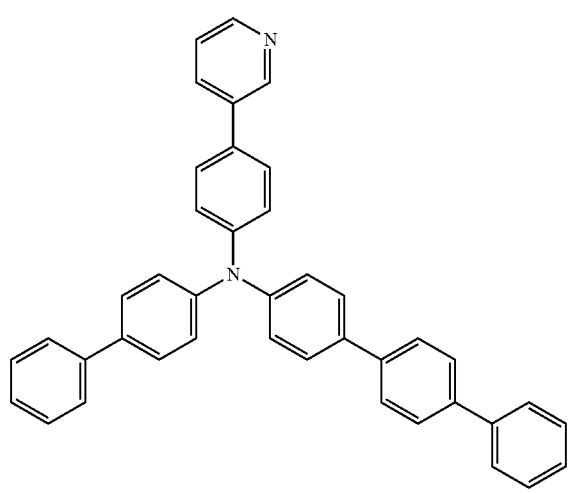
H-19
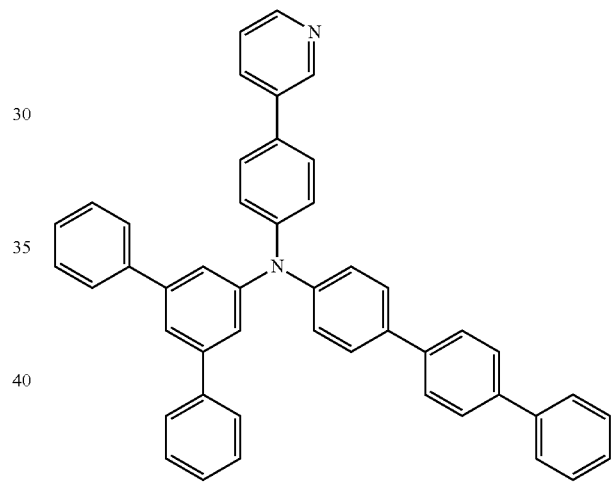
H-20
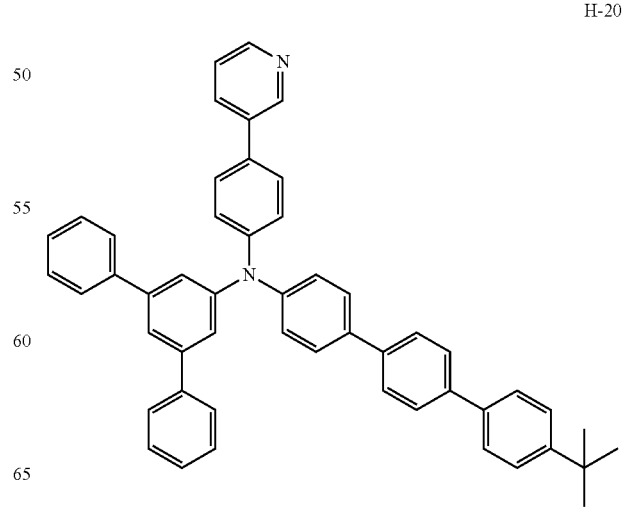

H-21
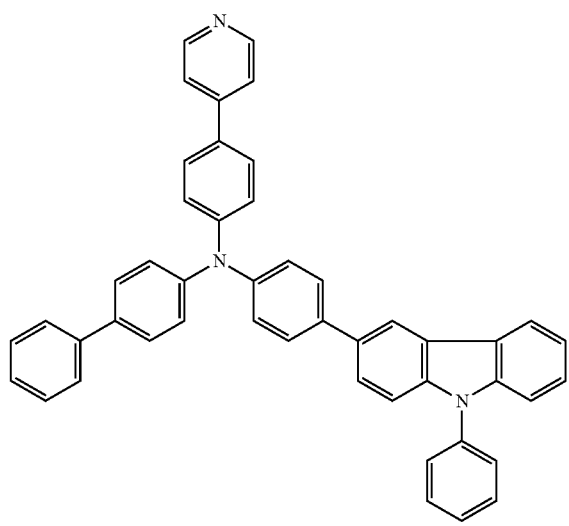
H-22
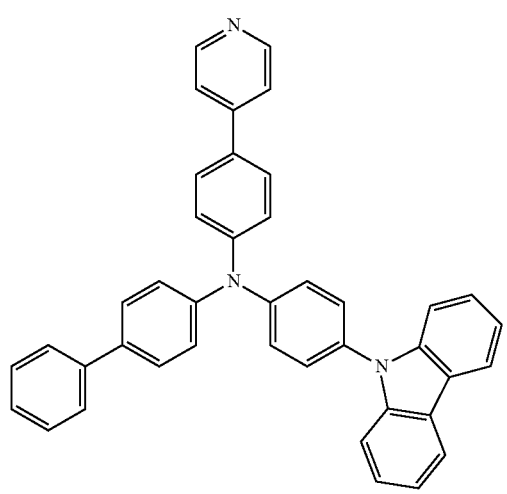
H-23
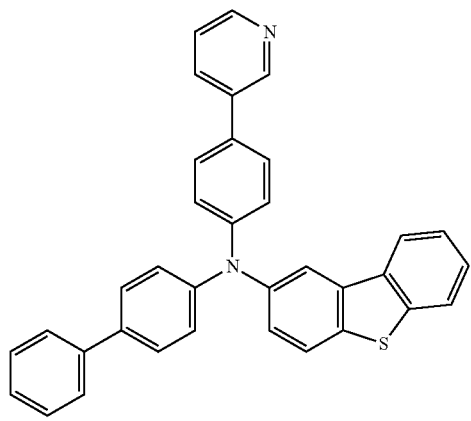
H-24
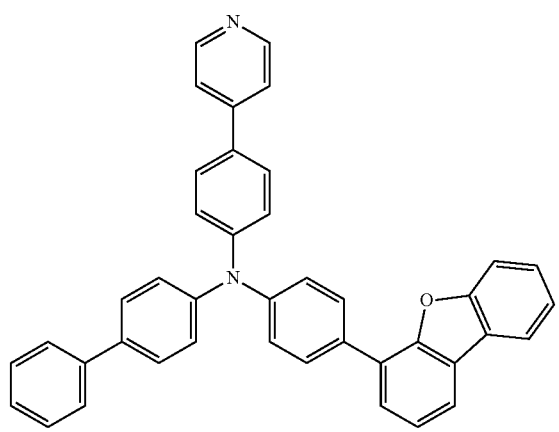
H-25
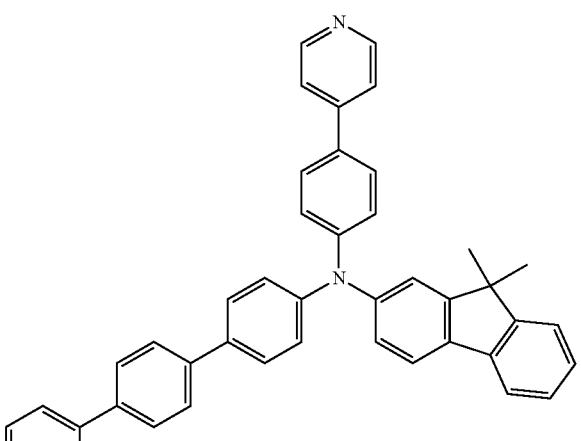
H-26
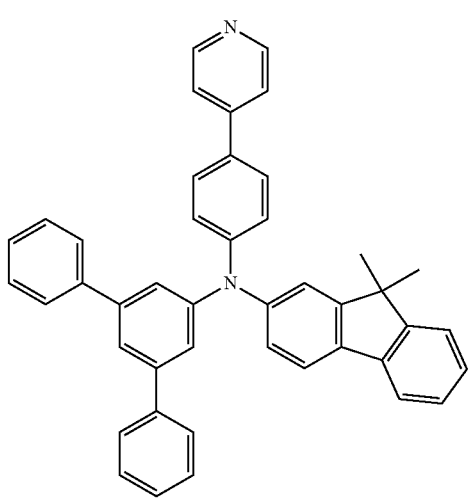

H-27
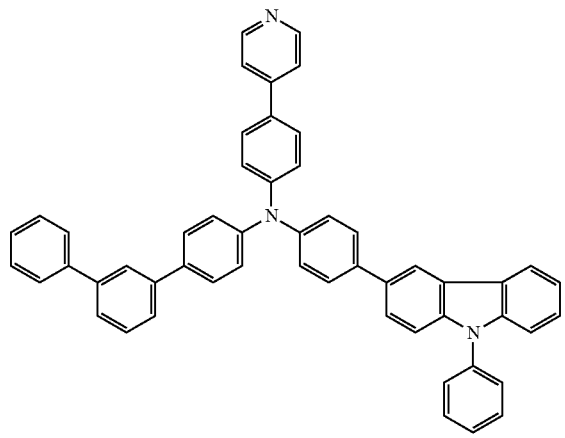
H-28
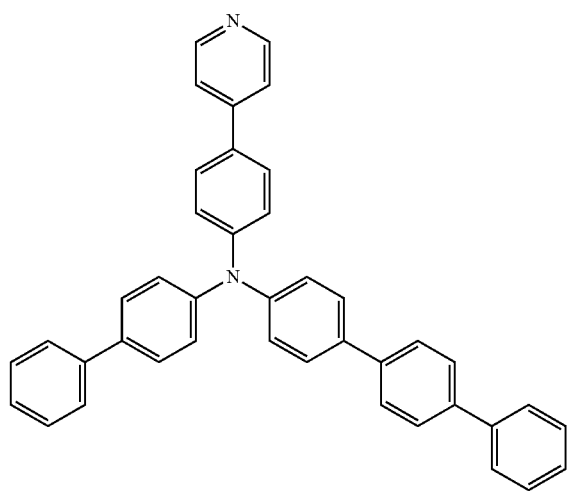
H-29
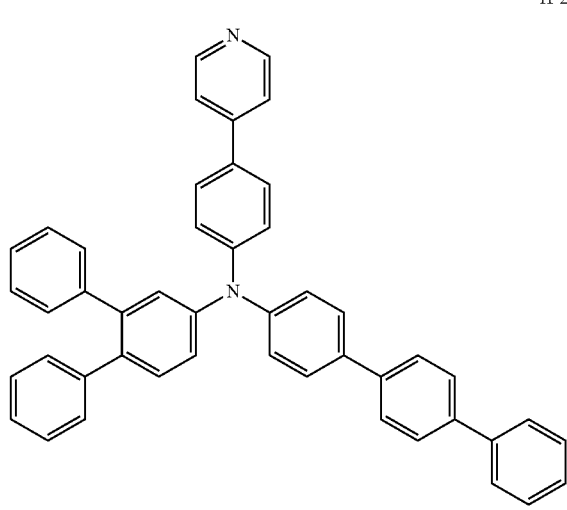
H-30
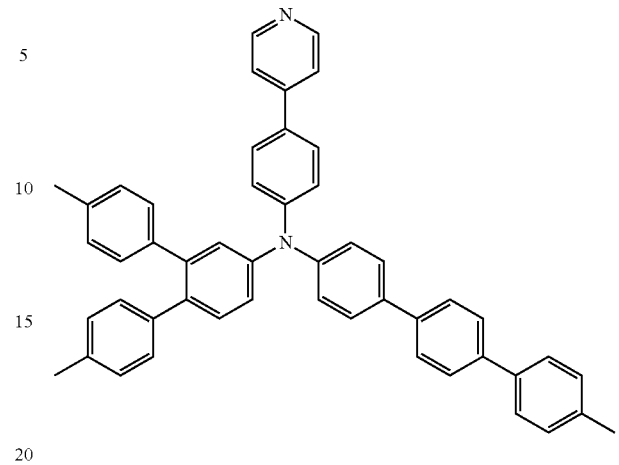
H-31
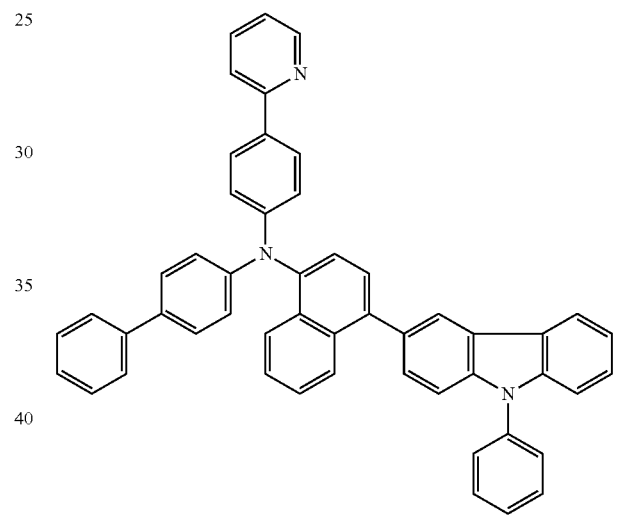
H-32
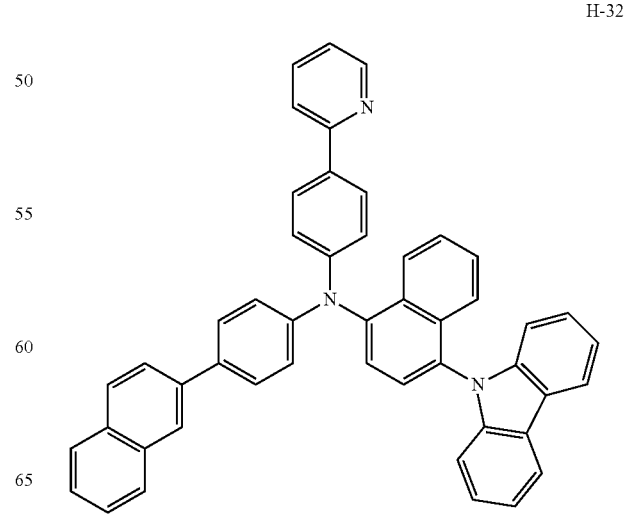

H-33
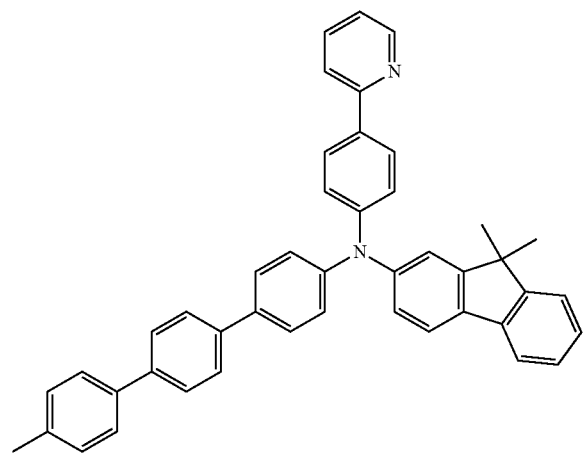
H-34
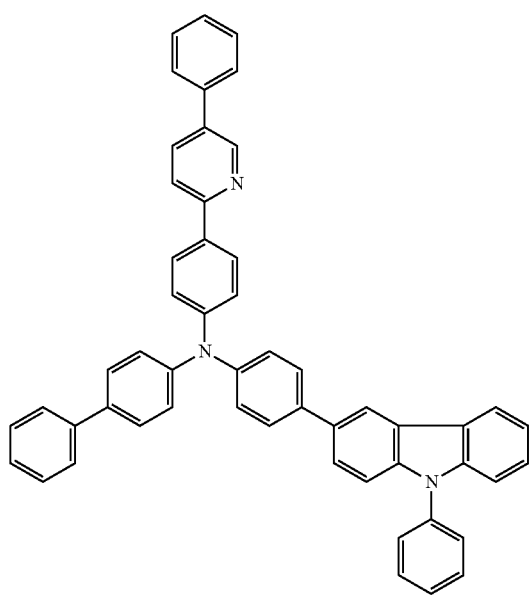
H-35
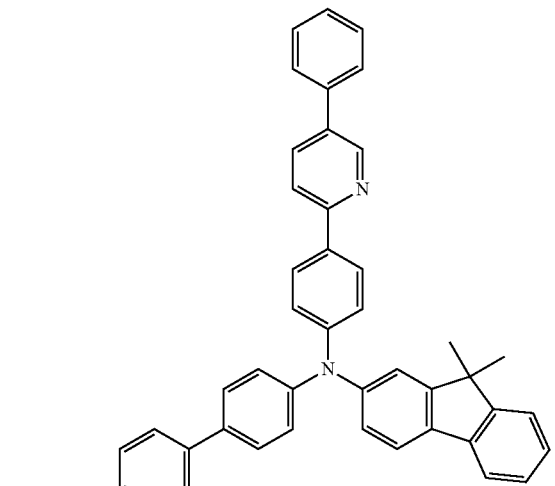
H-36
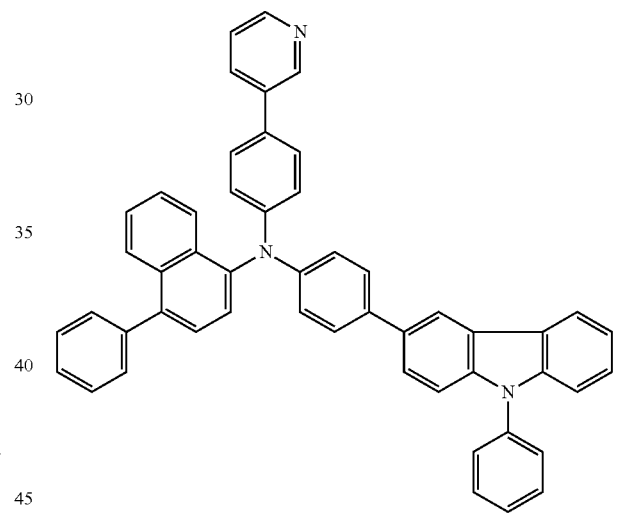
H-37
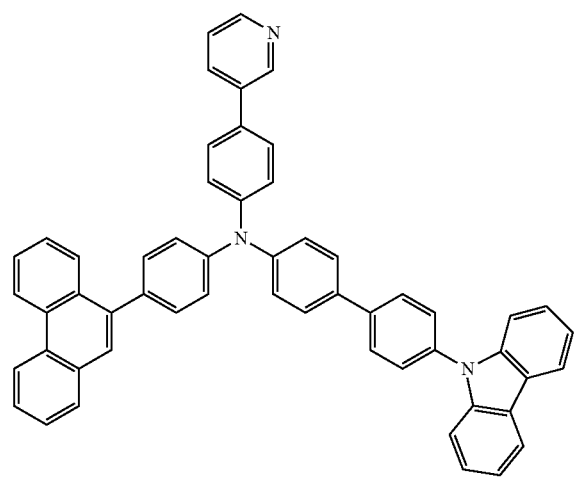

H-38
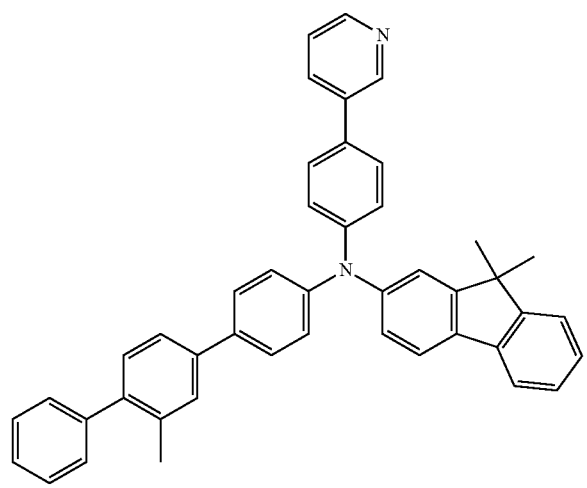
H-39
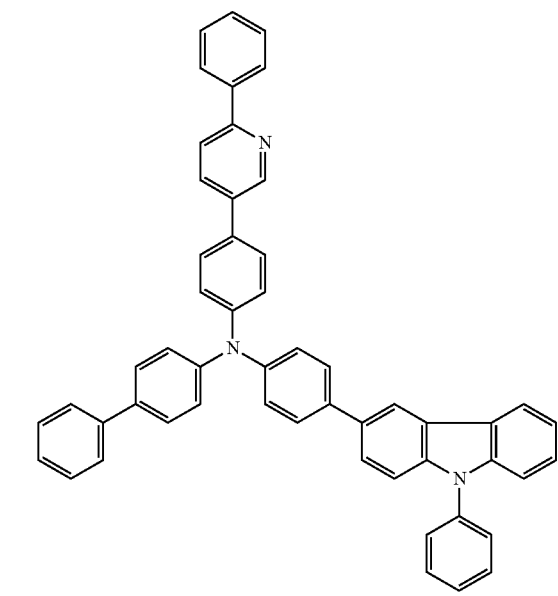
H-40
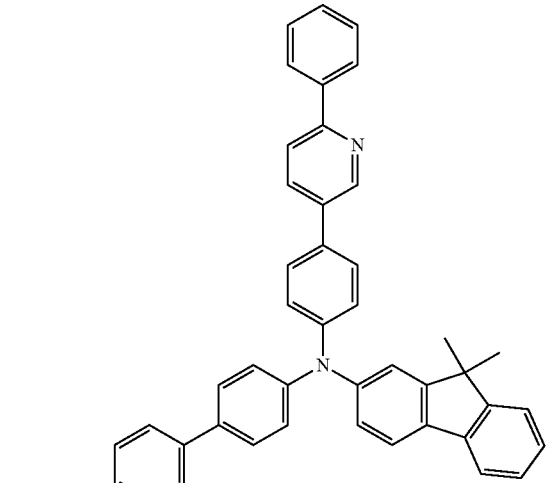
H-41
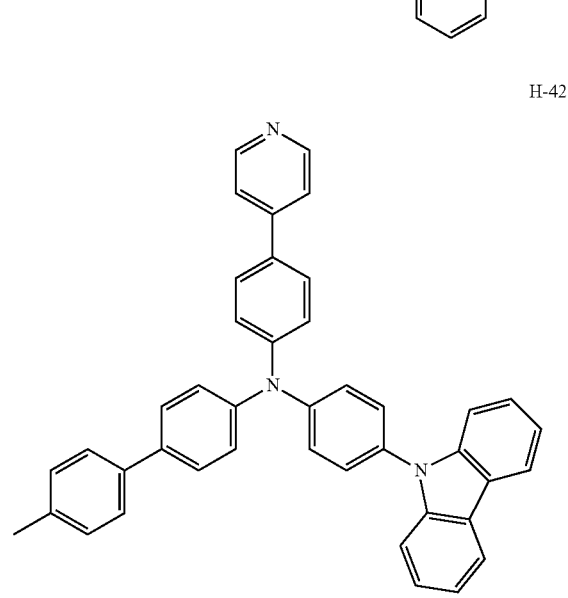
H-42

H-43
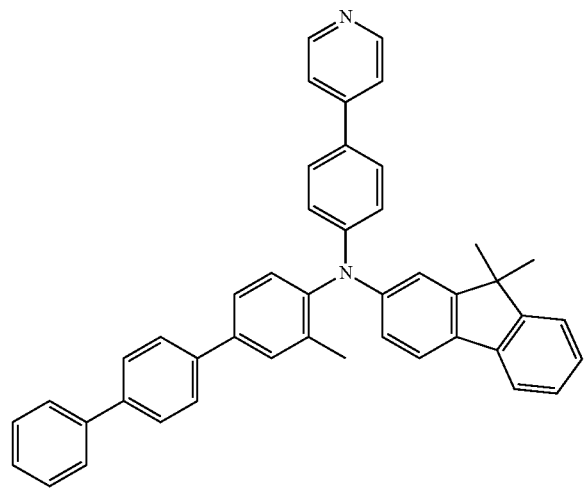
H-44
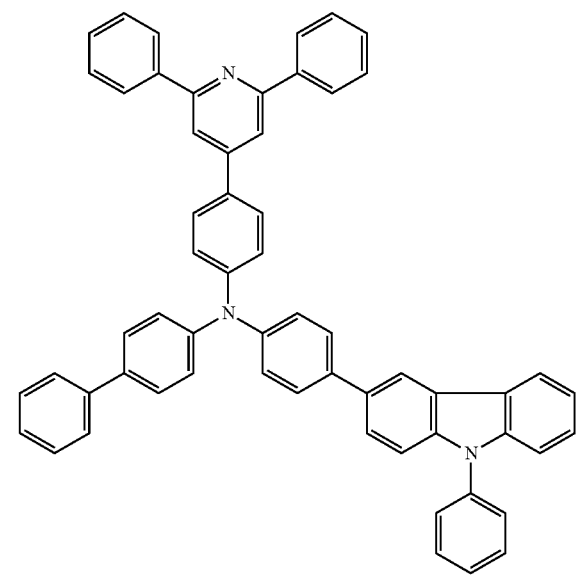
H-45
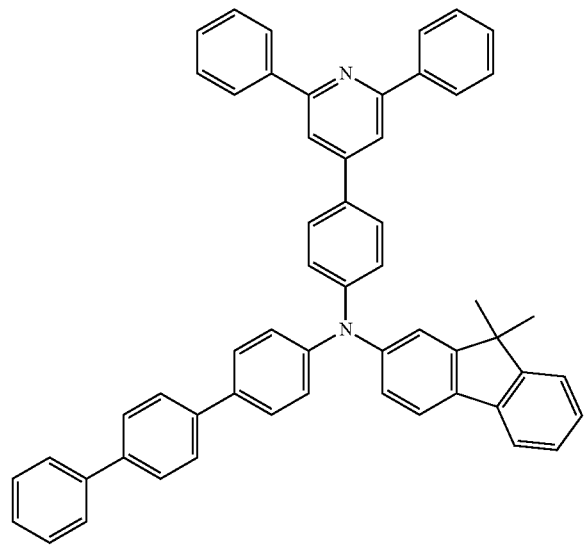
H-46
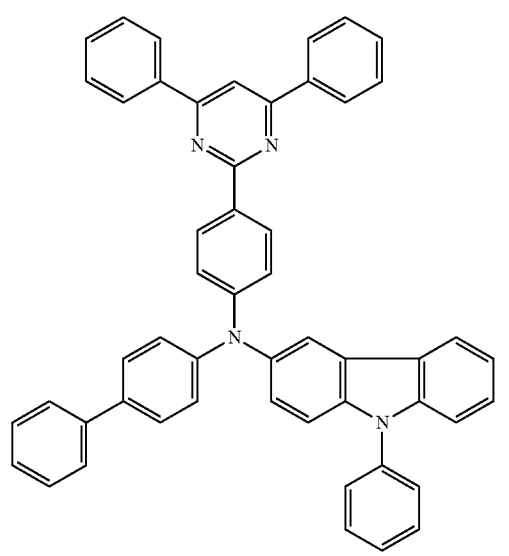
H-47
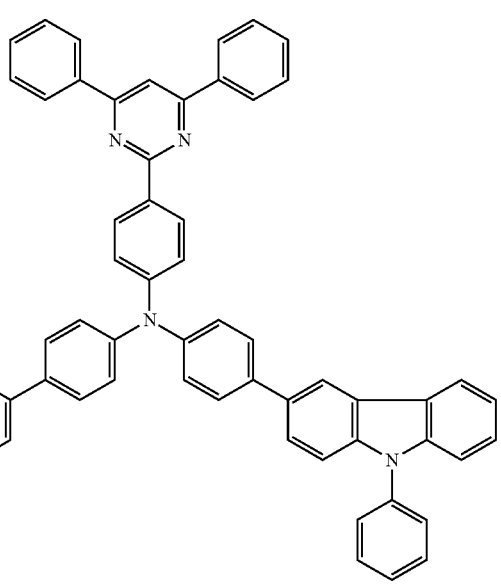

H-48
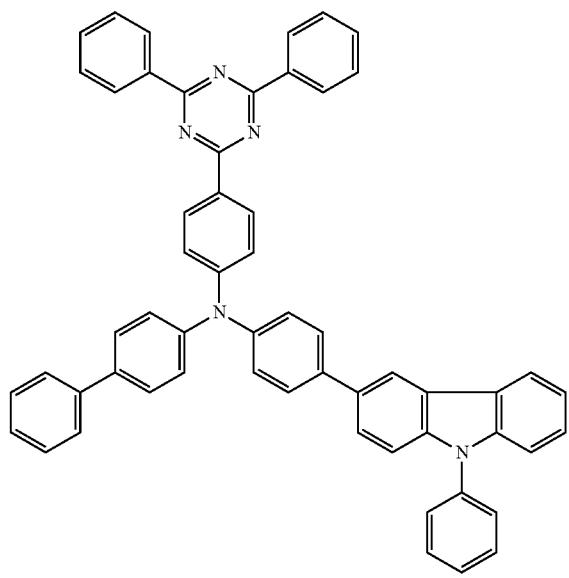
H-49
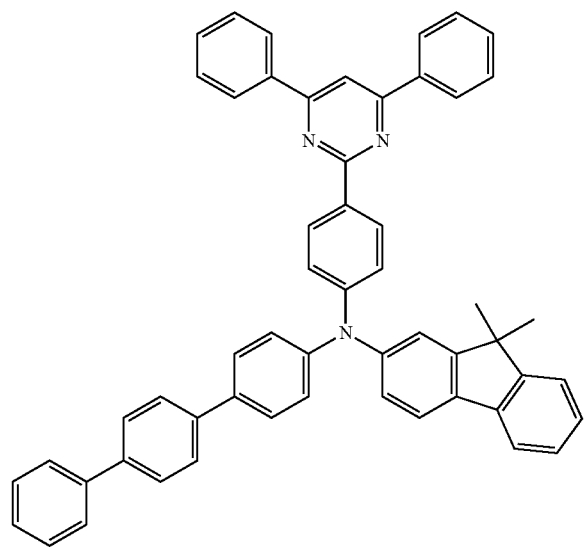
H-50
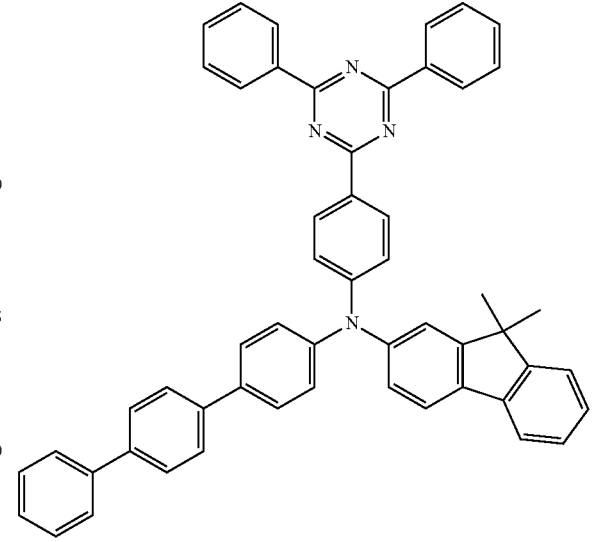
H-51
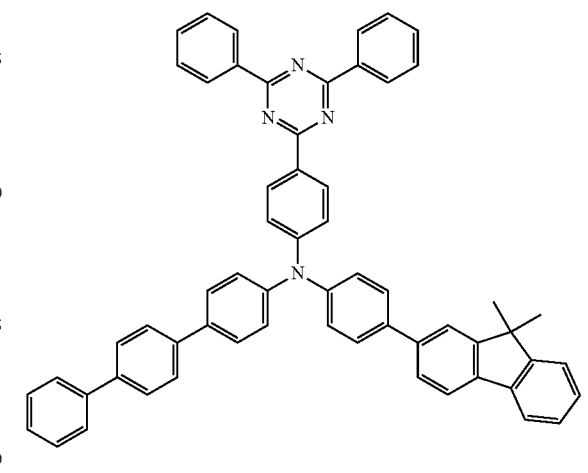
H-52
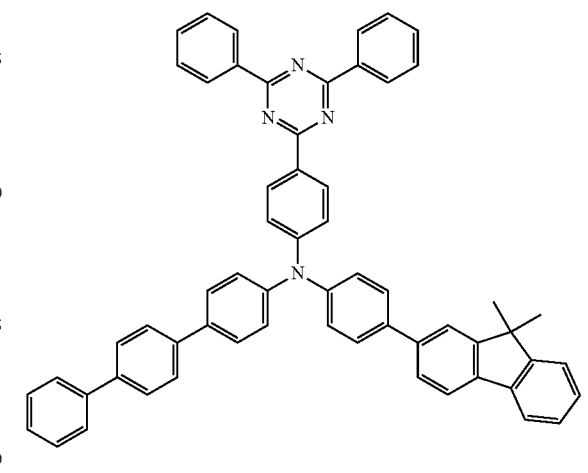
Since the organic compound of the present invention has an excellent hole transporting property, when the organic compound is included in the organic layer of an organic light emitting diode, the hole transporting efficiency in the organic light emitting diode is improved such that there is an advantage in the driving voltage. In addition, since the balance of the hole and the electron in the organic light emitting diode is improved, the emitting efficiency is increased. Moreover, since the stress on the organic materials by high driving voltage is decreased, the life time and the emitting efficiency are improved.

The organic compound singly or in combination with the dopant is used for an organic layer, e.g., a hole auxiliary layer such as a hole transporting layer or a hole injection layer, an electron blocking layer and a p-type charge transporting layer.

FIG. 1 is a schematic cross-sectional view of an organic light emitting diode according to a first embodiment of the present invention.

As shown in FIG. 1, the organic light emitting diode 100 includes a first electrode 110, a second electrode 120, an emitting part 130 between the first and second electrodes 110 and 120. The emitting part 130 includes a hole auxiliary layer 140, which may include a hole injection layer (HIL) 150 and a hole transporting layer (HTL) 160, an emitting material layer (EML) 170, an electron transporting layer (ETL) 180 and an electron injection layer (EIL) 190 sequentially stacked on the first electrode 110. The organic light emitting diode 100 may further include an electron blocking layer (EBL) 166 between the hole auxiliary layer 140 and the EML 170. The EBL 166 may be omitted.

The first electrode 110 as an anode includes a high work function conductive material, e.g., indium-tin-oxide (ITO) or indium-zinc-oxide (IZO).

The second electrode 120 as a cathode includes a low work function conductive material, e.g., aluminum (Al), magnesium (Mg), calcium (Ca), silver (Ag) or their alloy.

The EML 170 may include a host and a dopant.

For example, the EML 170 in a blue pixel may include an anthracene derivative compound, a pyrene derivative compound and a perylene derivative compound as the host and the dopant doped to the host.

For example, a fluorescent host material, such as 4,4'-bis(2,2'-diphenylyinyl)-1,1'-biphenyl (DPVBi), 9,10-di-(2-naphtyl)anthracene (AND), tetra-t-butylperylene (TBADN), 2-tert-butyl-9,10-di(2-naphthyl)anthracene, 2-methyl-9,10-di(2-naphthyl)anthracene (MADN), or 2,2',2"-(1,3,5-benzinetriyl)-tris(1-phenyl-1-H-benzimidazole (TBPi), may be used. A fluorescent dopant material, such as 4,4'-bis(9-ethyl-3-carbazovinylene)-1,1'-biphenyl (BCzVBi) or diphenyl-[4-(2-[1,1;4,1]terphenyl-4-yl-vinyl)-phenyl]-amine (BD-1) may be used.

The EML 170 in a green pixel may include a carbazole derivative compound as a phosphorescent host and a metal complex, e.g., dp2Ir(acac) or op2Ir(acac), as a phosphorescent dopant. The EML 170 in a red pixel may include a carbazole derivative compound as a phosphorescent host and a metal complex, e.g., Btp2Ir(acac), as a phosphorescent dopant. The dopant may have a weight % of about 1 to 30 with respect to the host.

The ETL 180 is positioned between the EML 170 and the second electrode 120, and the EIL 190 is positioned between the ETL 180 and the second electrode 120. The ETL 180 may be formed of a derivative compound of oxadiazole, triazole, phenanthroline, benzoxazole, benzothiazole, benzimidazole or triazine. For example, the ETL 180 may be formed of an electron transporting material selected from the group consisting of tris-(8-hydroxyquinoline aluminum (Alq3), 2-biphenyl-4-yl-5-(4-t-butylphenyl)-1,3,4-oxadiazole (PBD), spiro-PBD, Liq, 2-[4-(9,10-Di-2-naphthalenyl-2-anthracenyl)phenyl]-1-phenyl-1H-benzimidazol, 3-(biphenyl-4-yl)-5-(4-tertbutylphenyl)-4-phenyl-4H-1,2,4-triazole (TAZ), 4,7-diphenyl-1,10-phenanthroline (Bphen), tris(phenylquinoxaline (TPQ) and 1,3,5-tris(N-phenylbenzimiazole-2-yl)benzene (TPBI), but it is not limited thereto.

Alternatively, the ETL 180 may include the above electron transporting material and a metal, e.g., alkali metal or alkali earth metal, as a dopant. In this instance, the dopant may have a weight % of about 1 to 20 with respect to the electron transporting material, but it is not limited thereto. For example, the dopant may be one of Li, Na, K, Cs, Mg, Sr, Ba and Ra, but it is not limited thereto. The ETL 180 may have a single-layered structure or a multi-layered structure.

The EIL 190 may include an alkali halide compound, e.g., LiF, CsF, NaF or BaF2, or an organo-metallic compound, e.g., lithium quinolate (Liq), lithium benzoate or sodium stearate, but it is not limited thereto.

The hole auxiliary layer 140 and the EBL 166 are positioned between the first electrode 110 and the EML 170. The hole auxiliary layer 140 may include the HIL 150 between the first electrode 110 and the EML 170 and the HTL 160 between the HIL 150 and the EML 170.

The interface property between the first electrode 110 of an inorganic material and the HTL 160 of an organic material is improved by the HIL 150. For example, the HIL 150 may be formed of a hole injection material such as 4,4',4"-tris(3-methylphenylphenylamino)triphenylamine (MTDATA), copper phthalocyanine (CuPc), Tris(4-carbazoyl-9-yl-phenyl)amine (TCTA), N,N'-diphenyl-N,N'-bis(1-naphthyl)-1,1'-biphenyl-4,4 "-diamine (NPB or NPD), 1,4,5,8,9,11-hexaazatriphenylenehexacarbonitrile (HATCN), 1,3,5-tris[4-(diphenylamino)phenyl]benzene (TDAPB), poly(3,4-ethylenedioxythiophene)polystyrene sulfonate (PEDOT/PSS), 2,3,5, 6-tetrafluoro-7,7, 8, 8-tetracyanoquinodimethane (F4TCNQ) or N-(biphenyl-4-yl)-9,9-dimethyl-N-(4-(9-phenyl-9H-carbazol-3-yl)phenyl)-9H-fluoren-2-amine.

Alternatively, the organic compound of the present invention may be doped into the hole injection material to form the HIL 150. In this instance, the organic compound of the present invention may have a weight % of about 0.1 to 50, but it is not limited thereto.

The HIL 150 may have a double-layered structure. In this instance, a lower layer (first HIL) of the HIL 150, which is closer to the first electrode 110 than the an upper layer (second HIL) of the HIL 150, may include the hole injection material without the organic compound of the present invention, and the upper layer of the HIL 150, which is positioned between the lower layer and the HTL 160, may include the hole injection material with the organic compound of the present invention.

The HTL 160 is positioned between the HIL 150 and the EML 170 to be adjacent to the EML 170. The HTL 160 may include only the organic compound of the present invention or may include the organic compound and a hole transporting dopant. For example, the hole transporting dopant may be one of N,N'-diphenyl-N,N'-bis(3-methylphenyl)-1,1'-biphenyl-4,4'-diamine (TPD), NPD and 4,4'-bis(N-carbazolyl)-1,1'-biphenyl (CBP). The hole transporting dopant may have a weight % of about 0.1 to 50, but it is not limited thereto.

When the hole is migrated toward the second electrode 120 or the electron is migrated toward the first electrode 110 beyond the EML 170, the lifetime and the emitting efficiency of the organic light emitting diode may be decreased. To prevent this problem, the organic light emitting diode in an embodiment of the present invention may include an exciton blocking layer at an upper side or a lower side of the EML 170.

For example, the EBL 166 is formed between the hole auxiliary layer 140 and the EML 170 to block the migration of the electron. The EBL 166 may include the organic compound in an embodiment of the present invention.

Although not shown, a hole blocking layer may be formed between the EML 170 and the ETL 180 to block the migration of the hole. For example, the hole blocking layer may include a material of the ETL 180, such as a derivative of oxadiazole, triazole, phenanthroline, benzoxazole, benzothiazole, benzimidazole or triazine. The hole blocking layer may include a material having a relatively low highest occupied molecular orbital (HOMO), such as 2,9-dimethyl-4,7-diphenyl-1,10-phenanthroline (BCP) or bis(2-methyl-8-quinolinolato)(4-phenylphenolato)aluminum (III) (BAlq).

The organic light emitting diode 100 according to the first embodiment of the present invention includes the first electrode 110 and the second electrode 120, the emitting part 130 including the EML 170, the hole auxiliary layer 140, optionally the EBL 166, and at least one of the hole auxiliary layer 140 and the EBL 166 includes the organic compound of the present invention.

Since the organic compound of the present invention has an excellent hole transporting property, the organic compound singly or in combination with a dopant is used for the hole auxiliary layer 140 and/or the EBL 166 such that the driving voltage and the power consumption of the organic light emitting diode 100 is reduced and the lifetime and the emitting efficiency of the organic light emitting diode 100 is improved.

Figure 2:
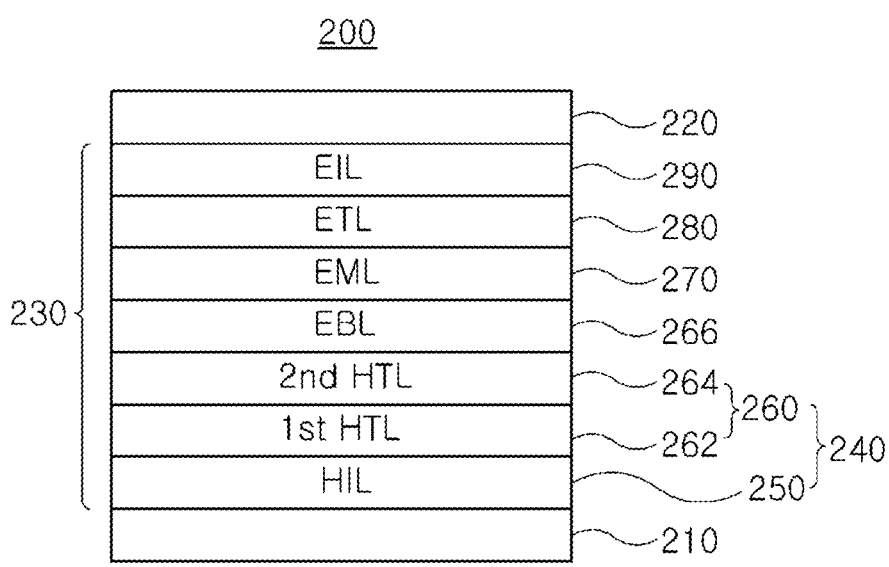
FIG. 2 is a schematic cross-sectional view of an organic light emitting diode according to a second embodiment of the present invention.

FIG. 2 is a schematic cross-sectional view of an organic light emitting diode according to a second embodiment of the present invention.

As shown in FIG. 2, the organic light emitting diode 200 includes a first electrode 210, a second electrode 220, an emitting part 230 between the first electrode 210 and the second electrode 220. The emitting part 230 includes a hole auxiliary layer 240, an EBL 266, an EML 270, an ETL 280 and an EIL 290. The hole auxiliary layer 240 and the EBL 266 are positioned between the first electrode 210 and the EML 270, and the ETL 280 and the EIL 290 are positioned between the EML 270 and the second electrode 220. The hole auxiliary layer 240 includes an HIL 250 and an HTL 260 including a first HTL 262 and a second HTL 264.

As mentioned above, the first electrode 210 as an anode includes a high work function conductive material, and the second electrode 220 as a cathode includes a low work function conductive material. The EML 270 may include a host and a dopant. The ETL 280 may include a derivative compound of oxadiazole, triazole, phenanthroline, benzoxazole, benzothiazole, benzimidazole or triazine. The ETL 280 may further include alkali metal or alkali earth metal as a dopant. The EIL 290 between the ETL 280 and the second electrode 220 may include an alkali halide compound, e.g., LiF, CsF, NaF or BaF2, or an organo-metallic compound, e.g., lithium quinolate (Liq), lithium benzoate or sodium stearate.

The interface property between the first electrode 210 of an inorganic material and the HTL 260 of an organic material is improved by the HIL 250. For example, the HIL 250 may be formed of a hole injection material such as MTDATA, CuPc, TCTA, NPB (NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine. Alternatively, the organic compound of the present invention may be doped into the hole injection material to form the HIL 250. In addition, the HIL 250 may include a lower layer (first HIL) of the HIL 250, which may include the hole injection material without the organic compound of the present invention, and the upper layer of the HIL 250, which may include the hole injection material with the organic compound of the present invention.

The HTL 260 includes the first HTL 262, which is closer to the HIL 250 than the second HTL 264, and the second HTL 262, which is closer to the EML 270 than the first HTL 262.

For example, the first HTL 262 may include the organic compound of the present invention and a hole transporting dopant, e.g., TPD, NPD or CBP. The hole transporting dopant may have a weight % of about 0.1 to 50, but it is not limited thereto. The second HTL 264 may include the organic compound of the present invention without the hole transporting dopant.

Alternatively, the first HTL 262 may include the organic compound of the present invention without the hole transporting dopant, and the second HTL 264 may include the organic compound of the present invention and the hole transporting dopant.

The EBL 266 is formed between the hole auxiliary layer 240 and the EML 270 to block the migration of the electron. The EBL 266 may include the organic compound of the present invention. Although not shown, a hole blocking layer may be formed between the EML 270 and the ETL 280 to block the migration of the hole.

In the organic light emitting diode 200, the HTL 260 has a double-layered structure. One of the HTL 260 only includes the organic compound of the present invention (i.e., without the hole transporting dopant), and the other one of the HTL 260 includes the organic compound of the present invention with the hole transporting dopant.

The organic light emitting diode 200 according to the second embodiment of the present invention includes the first electrode 210 and the second electrode 220, the emitting part 230 including the EML 270, the hole auxiliary layer 240, optionally the EBL 266, and at least one of the hole auxiliary layer 240 and the EBL 266 includes the organic compound of the present invention. In addition, the HTL 260 includes a first layer only including the organic compound of the present invention and a second layer including the organic compound of the present invention with the hole transporting dopant.

Since the organic compound of the present invention has an excellent hole transporting property, the organic compound singly or in combination with a dopant is used for the hole auxiliary layer 240 and/or the EBL 266 such that the driving voltage and the power consumption of the organic light emitting diode 200 is reduced and the lifetime and the emitting efficiency of the organic light emitting diode 200 is improved.

Figure 3:
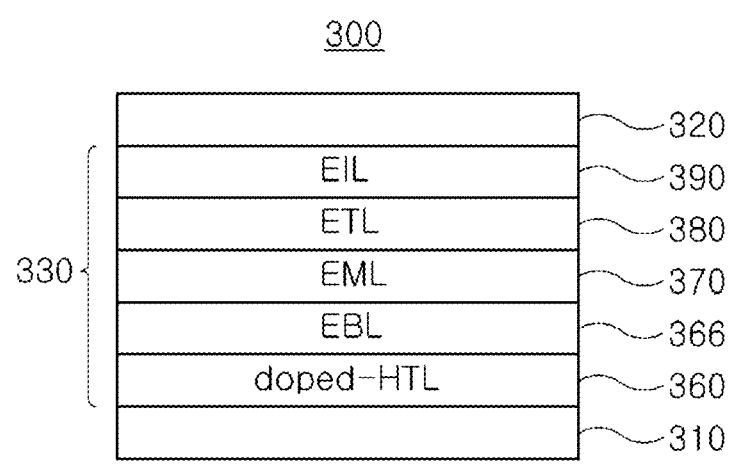
FIG. 3 is a schematic cross-sectional view of an organic light emitting diode according to a third embodiment of the present invention.

FIG. 3 is a schematic cross-sectional view of an organic light emitting diode according to a third embodiment of the present invention.

As shown in FIG. 3, the organic light emitting diode 300 includes a first electrode 310, a second electrode 320, an emitting part 330 between the first electrode 310 and the second electrode 320. The emitting part 330 includes a doped-HTL 360, an EBL 366, an EML 370, an ETL 380 and an EIL 390. The doped-HTL 360 and the EBL 366 are positioned between the first electrode 310 and the EML 370, and the ETL 380 and the EIL 390 are positioned between the EML 370 and the second electrode 320.

As mentioned above, the first electrode 310 as an anode includes a high work function conductive material, and the second electrode 320 as a cathode includes a low work function conductive material. The EML 370 may include a host and a dopant. The ETL 380 may include a derivative compound of oxadiazole, triazole, phenanthroline, benzoxazole, benzothiazole, benzimidazole or triazine. The ETL 380 may further include alkali metal or alkali earth metal as a dopant. The EIL 390 between the ETL 380 and the second electrode 320 may include an alkali halide compound, e.g., LiF, CsF, NaF or BaF2, or an organo-metallic compound, e.g., lithium quinolate (Liq), lithium benzoate or sodium stearate.

The doped-HTL 360 between the first electrode 310 and the EML 370 includes the organic compound of the present invention and a hole injection dopant such as MTDATA, CuPc, TCTA, NPB(NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine. The hole injection dopant may have a weight % of about 0.1 to 50, but it is not limited thereto.

The EBL 366 is formed between the doped-HTL 360 and the EML 370 to block the migration of the electron. The EBL 366 may include the organic compound of the present invention. Although not shown, a hole blocking layer may be formed between the EML 370 and the ETL 380 to block the migration of the hole.

In the organic light emitting diode 300, the doped-HTL 360 is formed by doping the hole injection dopant (hole injection material) into the organic compound of the present invention and contacts the first electrode 310 and the EBL 366 (or the EML 370 without the EBL 366).

The organic light emitting diode 300 according to the third embodiment of the present invention includes the first and second electrode 310 and 320 and the emitting part 330 including the EML 370, the doped-HTL 360, optionally the EBL 366, and at least one of the doped-HTL 360 and the EBL 366 includes the organic compound of the present invention.

Since the organic compound of the present invention has an excellent hole transporting property, the doped-HTL 360 has functions of the HIL as well as the HTL. Accordingly, even though the HTL 360 without the HIL is positioned between first electrode 310 and the EML 370, there are sufficient hole injection and transporting properties.

The organic compound singly or in combination with a dopant is used for the doped-HTL 360 and/or the EBL 366 such that the driving voltage and the power consumption of the organic light emitting diode 300 is reduced and the lifetime and the emitting efficiency of the organic light emitting diode 300 is improved.

Figure 4:
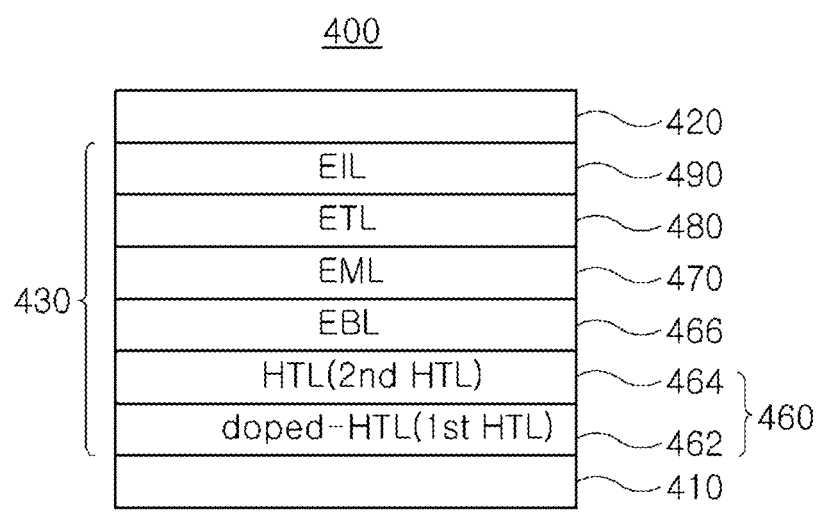
FIG. 4 is a schematic cross-sectional view of an organic light emitting diode according to a fourth embodiment of the present invention.

FIG. 4 is a schematic cross-sectional view of an organic light emitting diode according to a fourth embodiment of the present invention.

As shown in FIG. 4, the organic light emitting diode 400 includes a first electrode 410, a second electrode 420, an emitting part 430 between the first and second electrodes 410 and 420. The emitting part 430 includes an HTL 460, an EBL 466, an EML 470, an ETL 480 and an EIL 490. The HTL 460 and the EBL 466 are positioned between the first electrode 410 and the EML 470, and the ETL 480 and the EIL 490 are positioned between the EML 470 and the second electrode 420. The HTL 460 includes a first HTL 462 as a doped-HTL and a second HTL 464.

As mentioned above, the first electrode 410 as an anode includes a high work function conductive material, and the second electrode 420 as a cathode includes a low work function conductive material. The EML 470 may include a host and a dopant. The ETL 480 may include a derivative compound of oxadiazole, triazole, phenanthroline, benzoxazole, benzothiazole, benzimidazole or triazine. The ETL 480 may further include alkali metal or alkali earth metal as a dopant. The EIL 490 between the ETL 480 and the second electrode 420 may include an alkali halide compound, e.g., LiF, CsF, NaF or BaF2, or an organo-metallic compound, e.g., lithium quinolate (Liq), lithium benzoate or sodium stearate.

The HTL 460 includes the first HTL 462 and the second HTL 464 sequentially stacked on the first electrode 420. Namely, the first HTL 462 is positioned between the first electrode 420 and the second HTL 464.

The first HTL 462 includes the organic compound of the present invention and a hole injection dopant such as MTDATA, CuPc, TCTA, NPB(NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine. The hole injection dopant may have a weight % of about 0.1 to 50, but it is not limited thereto.

The second HTL 464, which is positioned between the first HTL 462 and the EML 470, includes only the organic compound of the present invention or includes the organic compound of the present invention and a hole transporting dopant, e.g., TPD, NPD or CBP. The hole transporting dopant may have a weight % of about 0.1 to 50, but it is not limited thereto.

Namely, in comparison to the organic light emitting diode according to the third embodiment (FIG. 3), the organic light emitting diode according to the fourth embodiment includes the second HTL 464, which includes the organic compound of the present invention with or without the hole transporting dopant, as well as the first HTL 462 as the doped-HTL.

The EBL 466 is formed between the HTL 460 and the EML 470 to block the migration of the electron. The EBL 466 may include the organic compound of the present invention. Although not shown, a hole blocking layer may be formed between the EML 470 and the ETL 480 to block the migration of the hole.

The organic light emitting diode 400 according to the fourth embodiment of the present invention includes the first 410 and the second electrode 420 and the emitting part 430 including the EML 470, the HTL 460, optionally the EBL 466, and at least one of the HTL 460 and the EBL 466 includes the organic compound of the present invention. In addition, the HTL 460 includes the first HTL 462 including the organic compound of the present invention with the hole injection dopant and the second HTL 464 including the organic compound of the present invention with or without the hole transporting dopant.

Since the organic compound of the present invention has an excellent hole transporting property, the first HTL 462, where the hole injection dopant is doped, has functions of the HIL as well as the HTL. In addition, since the second HTL, which includes the organic compound of the present invention with or without the hole transporting dopant, is further formed between the first HTL 462 and the EML 470, the hole is further efficiently provided into the EML 470.

The organic compound singly or in combination with a dopant is used for the HTL 460 and/or the EBL 466 such that the driving voltage and the power consumption of the organic light emitting diode 400 is reduced and the lifetime and the emitting efficiency of the organic light emitting diode 400 is improved.

Figure 5:
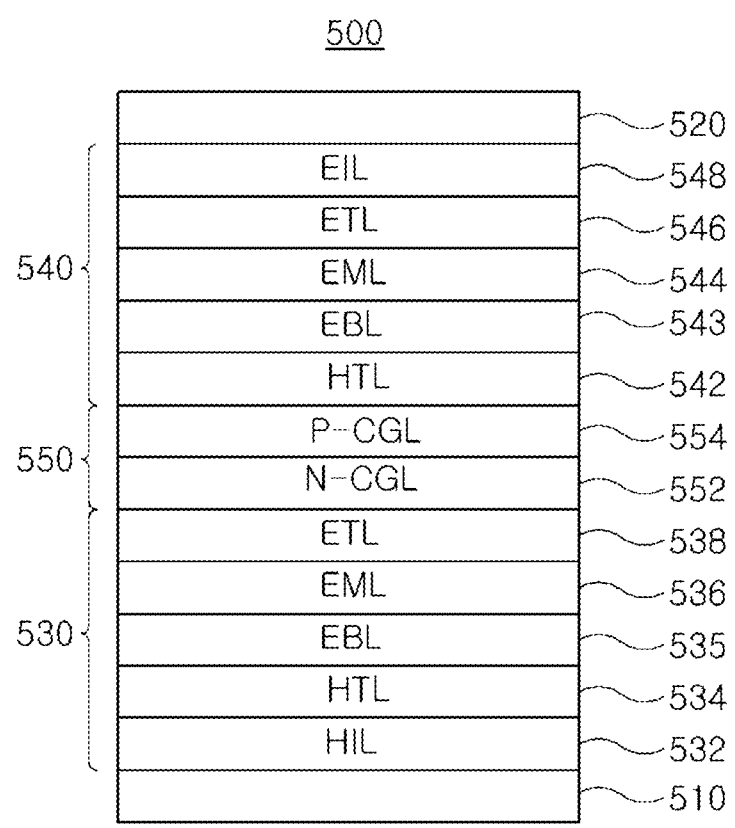
FIG. 5 is a schematic cross-sectional view of an organic light emitting diode according to a fifth embodiment of the present invention.

FIG. 5 is a schematic cross-sectional view of an organic light emitting diode according to a fifth embodiment of the present invention.

As shown in FIG. 5, the organic light emitting diode 500 includes a first electrode 510, a second electrode 520, a first emitting part 430 (a lower emitting part) between the first and second electrode 510 and 520, a second emitting part 540 (an upper emitting part) between the first emitting part 530 and the second electrode 520 and a charge generation layer (CGL) 550 between the first and second emitting parts 530 and 540.

As mentioned above, the first electrode 510 as an anode includes a high work function conductive material, and the second electrode 520 as a cathode includes a low work function conductive material.

The first emitting part 530 may include an HIL 532, a first HTL (a lower HTL) 534, a first EML (a lower EML) 536 and a first ETL (a lower ETL) 538, optionally a first EBL (a lower EBL) 535 between the first HTL 534 and the first EML 536.

The HIL 532 is positioned between the first electrode 510 and the first EML 536 and may be formed of a hole injection material such as MTDATA, CuPc, TCTA, NPB(NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine. Alternatively, the HIL 532 may further include the organic compound of the present invention doped into the hole injection material by a doping ratio of about 0.1 to 50 weight %. Alternatively, the HIL 532 may include a lower layer, which may include the hole injection material without the organic compound of the present invention, and the upper layer, which may include the hole injection material with the organic compound of the present invention.

The first HTL 534 is positioned between the HIL 532 and the first EML 536, and the first EML 536 is positioned between the first HTL 534 and the first ETL 538. The first ETL 538 is positioned between the first EML 536 and the CGL 550. The first EBL 535 is formed between the first HTL 534 and the first EML 536 to block the migration of the electron. The first EBL 535 may include the organic compound of the present invention. Although not shown, a hole blocking layer may be formed between the first EML 536 and the first ETL 538 to block the migration of the hole.

The second emitting part 540 includes a second HTL (an upper HTL) 542, a second EML (an upper EML) 544, a second ETL (an upper ETL) 546 and an EIL 548, and optionally a second EBL (an upper EBL) 543 between the second HTL 542 and the second EML 544.

The second EML 544 is positioned between the second HTL 542 and the second electrode 520, and the second ETL 546 is positioned between the second EML 544 and the second electrode 520. In addition, the EIL 548 is positioned between the second ETL 546 and the second electrode 520.

Each of the first EML 536 and the second EML 544 may include a host and a dopant. The first EML 536 and the second EML 544 emit the light having different colors. For example, the first EML 536 may emit the blue light, and the second EML 544 may emit the green light, the yellow-green light or the orange light, each of which has a longer wavelength than the blue light. In second EML 544 emitting the yellow-green light, CBP as a host and Ir(2-phq)3 as a dopant may be used.

Each of the first HTL 534 and the second HTL 542 may include a hole transporting material, such as TPD, NPD and CBP, or include the organic compound of the present invention. Alternatively, each of the first HTL 534 and the second HTL 542 may include the organic compound of the present invention with the above hole transporting material as a hole transporting dopant. The first HTL 534 and the second HTL 542 may be formed of the same material or different materials.

Each of the first ETL 538 and the second ETL 546 may include an electron transporting material such as a derivative compound of oxadiazole, triazole, phenanthroline, benzoxazole, benzothiazole or benzimidazole (e.g., 2-[4-(9,10-Di-2-naphthalenyl-2-anthracenyl)phenyl]-1-phenyl-1H-benzimidazole). The EIL 548 may include an alkali halide compound, e.g., LiF, CsF, NaF or BaF2, or an organometallic compound, e.g., lithium quinolate (Liq), lithium benzoate or sodium stearate. The first ETL ETL 538 and the second ETL 546 may be formed of the same material or different materials.

The CGL 550 is positioned between the first emitting part 530 and the second emitting part 540 and includes an N type CGL (N-CGL) 552 adjacent to the first emitting part 530 and a P type CGL (P-CGL) 554 adjacent to the second emitting part 540. The electron is provided into the first emitting part 530 by the N-CGL 552, and the hole is provided into the second emitting part 540 by the P-CGL 554.

The N-CGL 552 may be an organic layer doped by alkali metal, e.g., Li, Na, or K, or alkali earth metal, e.g., Mg, Ca, Sr, Ba or Ra. For example, the host organic material for the N-CGL 552 may be 4,7-diphenyl-1,10-phenanthroline (Bphen) or MTDATA. The alkali metal or alkali earth metal may be doped by a weight % of about 0.1 to 30.

The P-CGL 554 includes the organic compound of the present invention. In addition, the P-CGL 554 may further include a hole injection material, e.g., MTDATA, CuPc, TCTA, NPB (NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine, as a dopant. In this instance, the hole injection material may have a weight % of about 0.1 to 50, but it is not limited thereto.

The second EBL 543 is formed between the second HTL 542 and the second EML 544 to block the migration of the electron. The second EBL 543 may include the organic compound of the present invention. Although not shown, a hole blocking layer may be formed between the second EML 544 and the second ETL 546 to block the migration of the hole.

As mentioned above, the organic compound of the present invention has excellent hole transporting property. Accordingly, in the tandem structure organic light emitting diode 500 emitting the white light, the organic compound singly or in combination with the dopant is used for at least one of the second HTL 542, the P-CGL 554 and the second EBL 543 such that the driving voltage and the power consumption of the organic light emitting diode 500 is reduced and the lifetime and the emitting efficiency of the organic light emitting diode 500 is improved.

Figure 6:
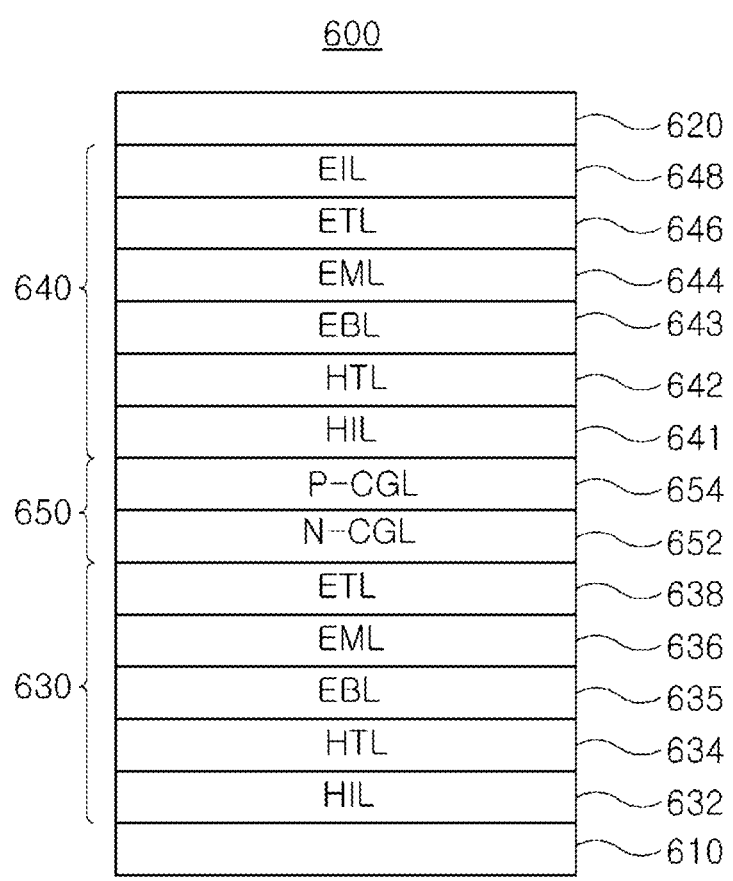
FIG. 6 is a schematic cross-sectional view of an organic light emitting diode according to a sixth embodiment of the present invention.

FIG. 6 is a schematic cross-sectional view of an organic light emitting diode according to a sixth embodiment of the present invention.

As shown in FIG. 6, the organic light emitting diode 600 includes a first electrode 610, a second electrode 620, a first emitting part 630 (a lower emitting part) between the first and second electrode 610 and 620, a second emitting part 640 (an upper emitting part) between the first emitting part 630 and the second electrode 620 and a CGL 650 between the first and second emitting parts 630 and 640.

As mentioned above, the first electrode 610 as an anode includes a high work function conductive material, and the second electrode 620 as a cathode includes a low work function conductive material.

The first emitting part 630 may include a first HIL (a lower HIL) 632, a first HTL (a lower HTL) 634, a first EML (a lower EML) 636 and a first ETL (a lower ETL) 638, and optionally a first EBL (a lower EBL) 635 between the first HTL 634 and the first EML 636.

The first HIL 632 is positioned between the first electrode 610 and the first EML 636, and the first HTL 634 is positioned between the first HIL 632 and the first EML 636. The first EML 636 is positioned between the first HTL 634 and the first ETL 638, and the first ETL 638 is positioned between the first EML 636 and the CGL 650. The first EBL 635 is formed between the first HTL 634 and the first EML 636 to block the migration of the electron. The first EBL 635 may include the organic compound of the present invention. Although not shown, a hole blocking layer may be formed between the first EML 636 and the first ETL 638 to block the migration of the hole.

The second emitting part 640 includes a second HIL (an upper HIL) 641, a second HTL (an upper HTL) 642, a second EML (an upper EML) 644, a second ETL (an upper ETL) 646 and an EIL 648, and optionally a second EBL (an upper EBL) 643 between the second HTL 642 and the second EML 644.

The second HIL 641 is positioned between the CGL 650 and the second HTL 642, and the second HTL 642 is positioned between the second HIL 641 and the second electrode 620. The second EML 644 is positioned between the second HTL 642 and the second electrode 620, and the second ETL 646 is positioned between the second EML 644 and the second electrode 620. In addition, the EIL 648 is positioned between the second ETL 646 and the second electrode 620.

Each of the first EML 636 and the second EML 644 may include a host and a dopant. The first EML 636 and the second EML 644 emit the light having different colors. For example, the first EML 636 may emit the blue light, and the second EML 644 may emit the green light, the yellow-green light or the orange light, each of which has a longer wavelength than the blue light.

Each of the first HIL 632 and the second HIL 641 may be formed of a hole injection material such as MTDATA, CuPc, TCTA, NPB(NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine. Alternatively, each of the first HIL 632 and the second HIL 641 may further include the organic compound of the present invention doped into the hole injection material by a doping ratio of about 0.1 to 50 weight %. The first HIL 632 and the second HIL 641 may be formed of the same material or different materials.

Each of the first HTL 634 and the second HTL 642 may include a hole transporting material, such as TPD, NPD and CBP, or include the organic compound of the present invention. Alternatively, each of the first HTL 634 and the second HTL 642 may include the organic compound of the present invention with the above hole transporting material as a hole transporting dopant. The first HTL 634 and the second HTL 642 may be formed of the same material or different materials.

Each of the first ETL 638 and the second ETL 646 may include an electron transporting material such as a derivative compound of oxadiazole, triazole, phenanthroline, benzoxazole, benzothiazole or benzimidazole (e.g., 2-[4-(9,10-Di-2-naphthalenyl-2-anthracenyl)phenyl]-1-phenyl-1H-benzimidazole). The EIL 648 may include an alkali halide compound, e.g., LiF, CsF, NaF or BaF2, or an organometallic compound, e.g., lithium quinolate (Liq), lithium benzoate or sodium stearate. The first ETL 638 and the second ETL 646 may be formed of the same material or different materials.

The CGL 650 is positioned between the first emitting part 630 and the second emitting part 640 and includes an N-CGL 652 adjacent to the first emitting part 630 and a P-CGL 654 adjacent to the second emitting part 640. The electron is provided into the first emitting part 630 by the N-CGL 652, and the hole is provided into the second emitting part 640 by the P-CGL 654.

The N-CGL 652 may be an organic layer doped by alkali metal, e.g., Li, Na, or K, or alkali earth metal, e.g., Mg, Ca, Sr, Ba or Ra. For example, the host organic material for the N-CGL 652 may be 4,7-diphenyl-1,10-phenanthroline (Bphen) or MTDATA. The alkali metal or alkali earth metal may be doped by a weight % of about 0.1 to 30.

The P-CGL 654 includes the organic compound of the present invention. In addition, the P-CGL 654 may further include a hole injection material, e.g., MTDATA, CuPc, TCTA, NPB (NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine, as a dopant. In this instance, the hole injection material may have a weight % of about 0.1 to 50, but it is not limited thereto.

The second EBL 643 is formed between the second HTL 642 and the second EML 644 to block the migration of the electron. The second EBL 643 may include the organic compound of the present invention. Although not shown, a hole blocking layer may be formed between the second EML 644 and the second ETL 646 to block the migration of the hole.

As mentioned above, the organic compound of the present invention has excellent hole transporting property. Accordingly, in the tandem structure organic light emitting diode 600 emitting the white light, the organic compound singly or in combination with the dopant is used for at least one of the second HIL 641, the second HTL 642, the P-CGL 654 and the second EBL 643 such that the driving voltage and the power consumption of the organic light emitting diode 600 is reduced and the lifetime and the emitting efficiency of the organic light emitting diode 600 is improved.

Figure 7:
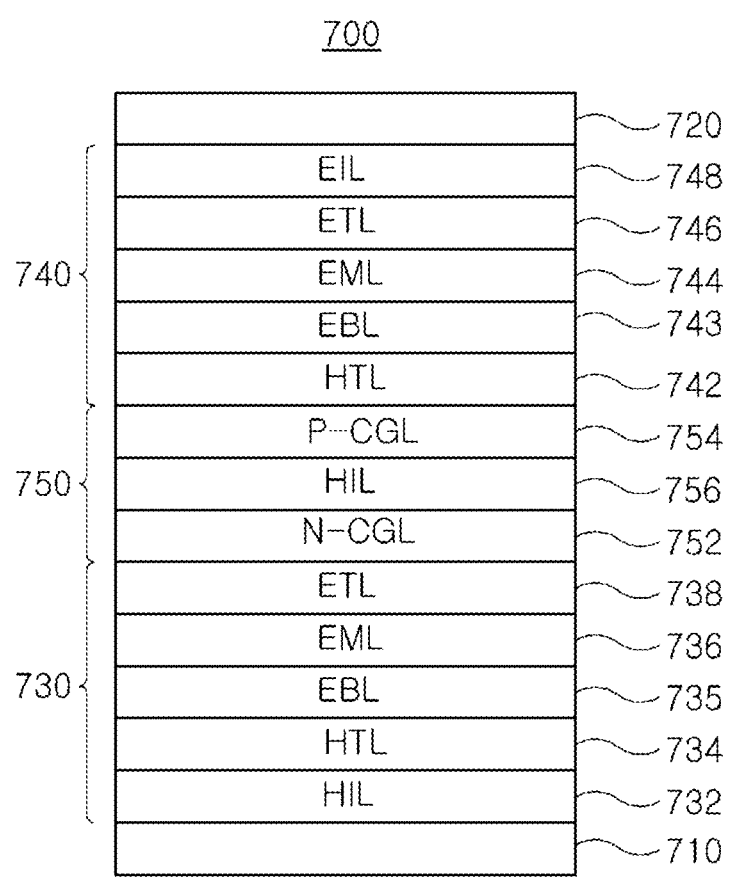
FIG. 7 is a schematic cross-sectional view of an organic light emitting diode according to a seventh embodiment of the present invention.

FIG. 7 is a schematic cross-sectional view of an organic light emitting diode according to a seventh embodiment of the present invention.

As shown in FIG. 7, the organic light emitting diode 700 includes a first electrode 710, a second electrode 720, a first emitting part 730 (a lower emitting part) between the first and second electrode 710 and 720, a second emitting part 740 (an upper emitting part) between the first emitting part 730 and the second electrode 720 and a CGL 750 between the first and second emitting parts 730 and 740.

As mentioned above, the first electrode 710 as an anode includes a high work function conductive material, and the second electrode 720 as a cathode includes a low work function conductive material.

The first emitting part 730 may include a first HIL (a lower HIL) 732, a first HTL (a lower HTL) 734, a first EML (a lower EML) 736 and a first ETL (a lower ETL) 738, and optionally a first EBL (a lower EBL) 735 between the first HTL 734 and the first EML 736.

The first HIL 732 is positioned between the first electrode 710 and the first EML 736, and the first HTL 734 is positioned between the first HIL 732 and the first EML 736. The first EML 736 is positioned between the first HTL 734 and the first ETL 738, and the first ETL 738 is positioned between the first EML 736 and the CGL 750.

The first EBL 735 is formed between the first HTL 734 and the first EML 736 to block the migration of the electron. The first EBL 735 may include the organic compound of the present invention. Although not shown, a hole blocking layer may be formed between the first EML 736 and the first ETL 738 to block the migration of the hole.

The second emitting part 740 includes a second HTL (an upper HTL) 742, a second EML (an upper EML) 744, a second ETL (an upper ETL) 746 and an EIL 748, and optionally a second EBL (an upper EBL) 743 between the second HTL 742 and the second EML 744.

The second HTL 742 is positioned between the CGL 750 and the second electrode 720, and the second EML 744 is positioned between the second HTL 742 and the second electrode 720. The second ETL 746 is positioned between the second EML 744 and the second electrode 720, and the EIL 748 is positioned between the second ETL 746 and the second electrode 720.

Each of the first EML 736 and the second EML 744 may include a host and a dopant. The first EML 736 and the second EML 744 emit the light having different colors. For example, the first EML 736 may emit the blue light, and the second EML 744 may emit the green light, the yellow-green light or the orange light, each of which has a longer wavelength than the blue light.

The first HIL 732 may be formed of a hole injection material such as MTDATA, CuPc, TCTA, NPB(NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine. Alternatively, the first HIL 732 may further include the organic compound of the present invention doped into the hole injection material by a doping ratio of about 0.1 to 50 weight %.

Each of the first HTL 734 and the second HTL 742 may include a hole transporting material, such as TPD, NPD and CBP, or include the organic compound of the present invention. Alternatively, each of the first and second HTLs 734 and 742 may include the organic compound of the present invention with the above hole transporting material as a hole transporting dopant. The first HTL 734 and the second HTL 742 may be formed of the same material or different materials.

Each of the first ETL 738 and the second ETL 746 may include an electron transporting material such as a derivative compound of oxadiazole, triazole, phenanthroline, benzoxazole, benzothiazole or benzimidazole (e.g., 2-[4-(9,10-Di-2-naphthalenyl-2-anthracenyl)phenyl]-1-phenyl-1H-benzimidazole). The EIL 748 may include an alkali halide compound, e.g., LiF, CsF, NaF or BaF2, or an organometallic compound, e.g., lithium quinolate (Liq), lithium benzoate or sodium stearate. The first and second ETLs 738 and 746 may be formed of the same material or different materials.

The CGL 750 is positioned between the first emitting part 730 and the second emitting part 740 and includes an N-CGL 752 adjacent to the first emitting part 730, a P-CGL 754 adjacent to the second emitting part 740 and a second HIL (intermediate charge generation layer) 756 between the N-CGL 752 and the P-CGL 754. The electron is provided into the first emitting part 730 by the N-CGL 752, and the hole is provided into the second emitting part 740 by the P-CGL 754.

The N-CGL 752 may be an organic layer doped by alkali metal, e.g., Li, Na, or K, or alkali earth metal, e.g., Mg, Ca, Sr, Ba or Ra. For example, the host organic material for the N-CGL 752 may be 4,7-diphenyl-1,10-phenanthroline (Bphen) or MTDATA. The alkali metal or alkali earth metal may be doped by a weight % of about 0.1 to 30.

The P-CGL 754 includes the organic compound of the present invention. In addition, the P-CGL 754 may further include a hole injection material, e.g., MTDATA, CuPc, TCTA, NPB (NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine, as a dopant. In this instance, the hole injection material may have a weight % of about 0.1 to 50, but it is not limited thereto.

The second HIL 756 may be formed of a hole injection material such as MTDATA, CuPc, TCTA, NPB (NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine. Alternatively, the second HIL 756 may further include the organic compound of the present invention doped into the hole injection material by a doping ratio of about 0.1 to 50 weight %. The first HIL 732 and the second HIL 756 may be formed of the same material or different materials.

The second EBL 743 is formed between the second HTL 742 and the second EML 744 to block the migration of the electron. The second EBL 743 may include the organic compound of the present invention. Although not shown, a hole blocking layer may be formed between the second EML 744 and the second ETL 746 to block the migration of the hole.

As mentioned above, the organic compound of the present invention has excellent hole transporting property. Accordingly, in the tandem structure organic light emitting diode 700 emitting the white light, the organic compound singly or in combination with the dopant is used for at least one of the second HTL 742, the P-CGL 754, the second HIL 756 and the second EBL 743 such that the driving voltage and the power consumption of the organic light emitting diode 700 is reduced and the lifetime and the emitting efficiency of the organic light emitting diode 700 is improved.

Figure 8:
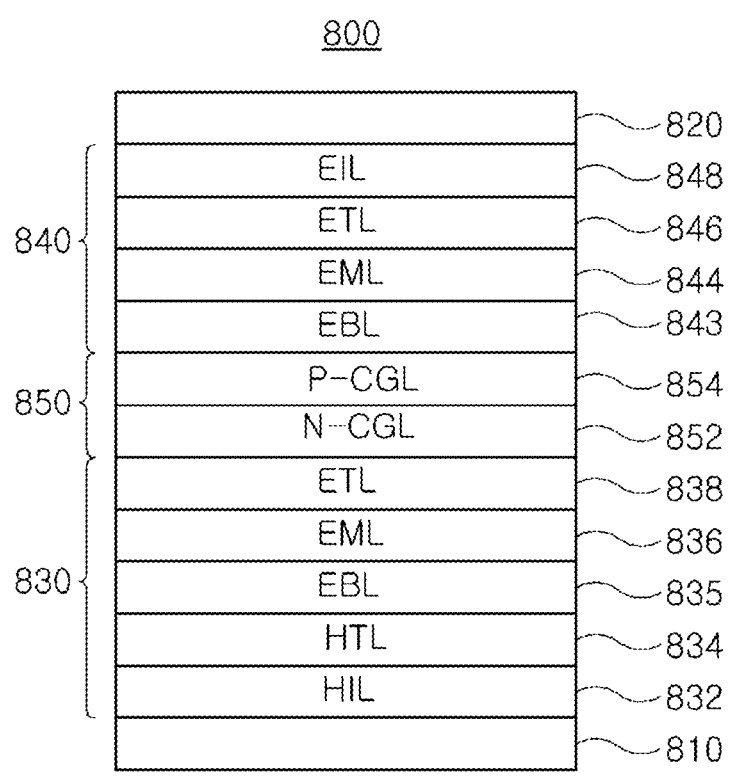
FIG. 8 is a schematic cross-sectional view of an organic light emitting diode according to an eighth embodiment of the present invention.

FIG. 8 is a schematic cross-sectional view of an organic light emitting diode according to an eighth embodiment of the present invention.

As shown in FIG. 8, the organic light emitting diode 800 includes a first electrode 810, a second electrode 820, a first emitting part 830 (a lower emitting part) between the first electrode 810 and the second electrode 820, a second emitting part 840 (an upper emitting part) between the first electrode 810 and the second electrode 820 and a CGL 850 between the first emitting part 830 and the second emitting part 840.

As mentioned above, the first electrode 810 as an anode includes a high work function conductive material, and the second electrode 820 as a cathode includes a low work function conductive material.

The first emitting part 830 may include an HIL 832, an HTL 834, a first EML (a lower EML) 836 and a first ETL (a lower ETL) 838, and optionally a first EBL (a lower EBL) 835 between the HTL 834 and the first EML 836.

The HIL 832 is positioned between the first electrode 810 and the first EML 836, and the HTL 834 is positioned between the HIL 832 and the first EML 836. The first EML 836 is positioned between the HTL 834 and the first ETL 838, and the first ETL 838 is positioned between the first EML 836 and the CGL 850.

The first EBL 835 is formed between the HTL 834 and the first EML 836 to block the migration of the electron. The first EBL 835 may include the organic compound of the present invention. Although not shown, a hole blocking layer may be formed between the first EML 836 and the first ETL 838 to block the migration of the hole.

The second emitting part 840 includes a second EML (an upper EML) 844, a second ETL (an upper ETL) 846 and an EIL 848, and optionally a second EBL (an upper EBL) 843 between the CGL 850 and the second EML 844.

The second EML 844 is positioned between the CGL 850 and the second electrode 820. The second ETL 846 is positioned between the second EML 844 and the second electrode 820, and the EIL 848 is positioned between the second ETL 846 and the second electrode 820.

Each of the first EML 836 and the second EML 844 may include a host and a dopant. The first EML 836 and the second EML 844 emit the light having different colors. For example, the first EML 836 may emit the blue light, and the second EML 844 may emit the green light, the yellow-green light or the orange light, each of which has a longer wavelength than the blue light.

The HIL 832 may be formed of a hole injection material such as MTDATA, CuPc, TCTA, NPB(NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine. Alternatively, the HIL 832 may further include the organic compound of the present invention doped into the hole injection material by a doping ratio of about 0.1 to 50 weight %.

The HTL 834 may include a hole transporting material, such as TPD, NPD and CBP, or include the organic compound of the present invention. Alternatively, the HTL 834 may include the organic compound of the present invention with the above hole transporting material as a hole transporting dopant.

Each of the first ETL 838 and the second ETL 846 may include an electron transporting material such as a derivative compound of oxadiazole, triazole, phenanthroline, benzoxazole, benzothiazole or benzimidazole (e.g., 2-[4-(9,10-Di-2-naphthalenyl-2-anthracenyl)phenyl]-1-phenyl-1H-benzimidazole). The EIL 848 may include an alkali halide compound, e.g., LiF, CsF, NaF or BaF2, or an organometallic compound, e.g., lithium quinolate (Liq), lithium benzoate or sodium stearate. The first ETL 838 and the second ETL 846 may be formed of the same material or different materials.

The CGL 850 is positioned between the first emitting part 830 and the second emitting part 840 and includes an N-CGL 852 adjacent to the first emitting part 830, a P-CGL 854 adjacent to the second emitting part 840 and a second HIL 856 between the N-CGL 852 and the P-CGL 854. The electron is provided into the first emitting part 830 by the N-CGL 852, and the hole is provided into the second emitting part 840 by the P-CGL 854.

The N-CGL 852 may be an organic layer doped by alkali metal, e.g., Li, Na, or K, or alkali earth metal, e.g., Mg, Ca, Sr, Ba or Ra. For example, the host organic material for the N-CGL 852 may be 4,7-diphenyl-1,10-phenanthroline (Bphen) or MTDATA. The alkali metal or alkali earth metal may be doped by a weight % of about 0.1 to 30.

The P-CGL 854 includes the organic compound of the present invention. In addition, the P-CGL 854 may further include a hole injection material, e.g., MTDATA, CuPc, TCTA, NPB (NPD), HATCN, TDAPB, PEDOT/PSS, F4TCNQ or N-(biphenyl-4-yl)-9,9-dimethyl-N-(4-(9-phenyl-9H-carbazol-3-yl)phenyl)-9H-fluoren-2-amine, as a dopant. In this instance, the hole injection material may have a weight % of about 0.1 to 50, but it is not limited thereto.

The second EBL 843 is formed between the CGL 850 and the second EML 844 to block the migration of the electron. The second EBL 843 may contact a surface of the CGL 850 and a surface of the second EML 844. The second EBL 843 may include the organic compound of the present invention. Although not shown, a hole blocking layer may be formed between the second EML 844 and the second ETL 846 to block the migration of the hole.

As mentioned above, the organic compound of the present invention has excellent hole transporting property. Accordingly, in the tandem structure organic light emitting diode 800 emitting the white light, the organic compound singly or in combination with the dopant is used for at least one of the P-CGL 854 and the second EBL 843 such that the driving voltage and the power consumption of the organic light emitting diode 800 is reduced and the lifetime and the emitting efficiency of the organic light emitting diode 800 is improved.

In the organic light emitting diodes in FIGS. 5 to 8, at least one of the HIL, the HTL, the EBL and the P-CGL includes the organic compound of the present invention with or without a dopant. In addition, the organic light emitting diodes may further include additional emitting part and additional CGL between adjacent emitting parts.

Figure 9:
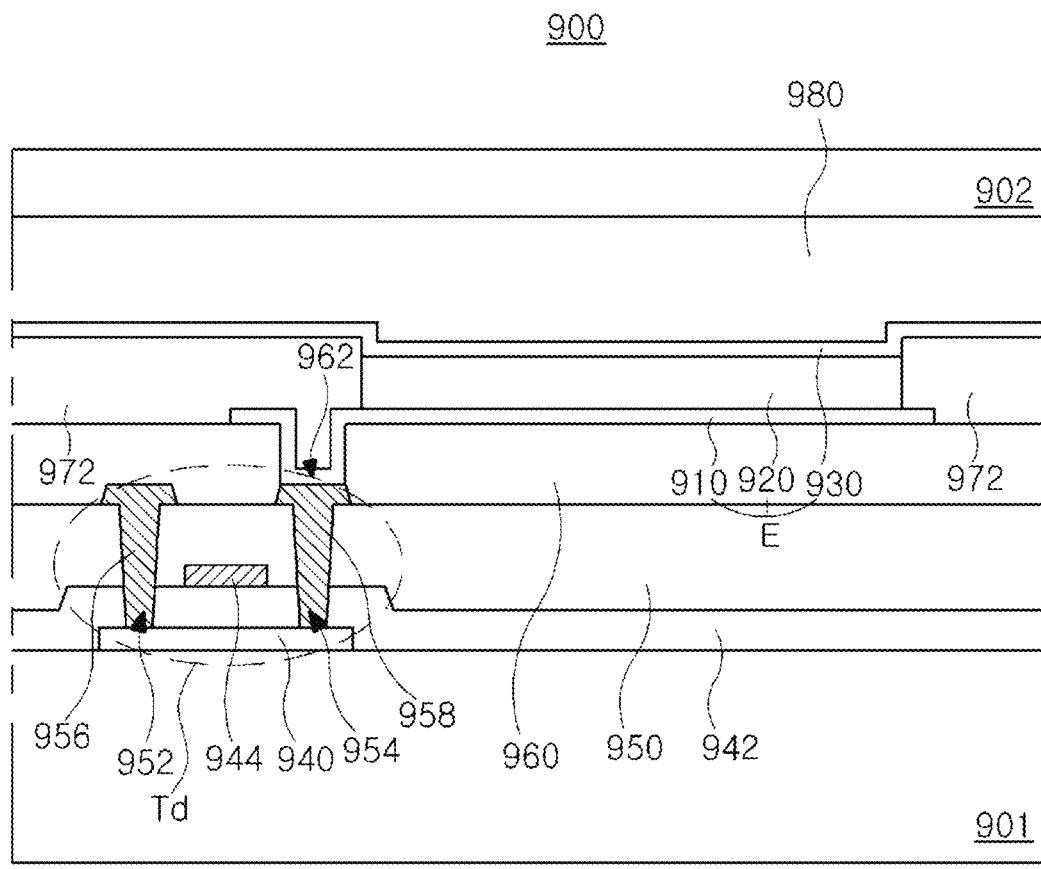
FIG. 9 is a schematic cross-sectional view of an OLED device according to an embodiment of the present invention.
Figure 10A:
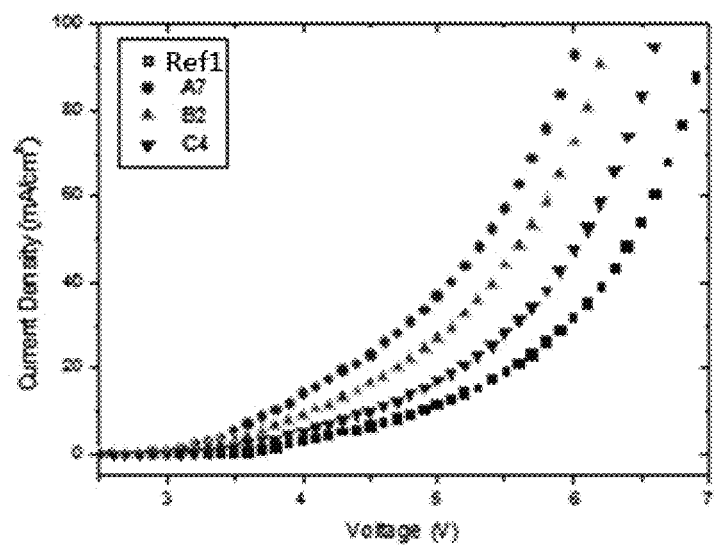
FIG. 10A, FIG. 10B and FIG. 10C are graphs showing the current density of the organic light emitting diode including an organic compound in an exciton blocking layer.
Figure 10B:
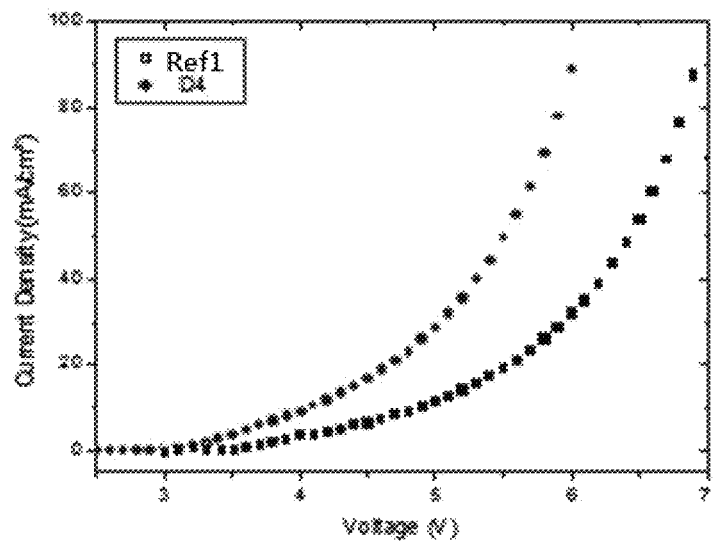
Figure 10C:
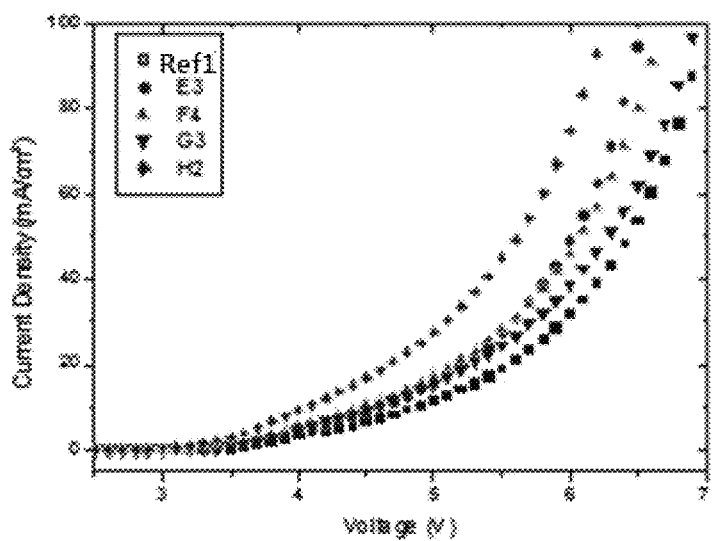
Figure 11A:
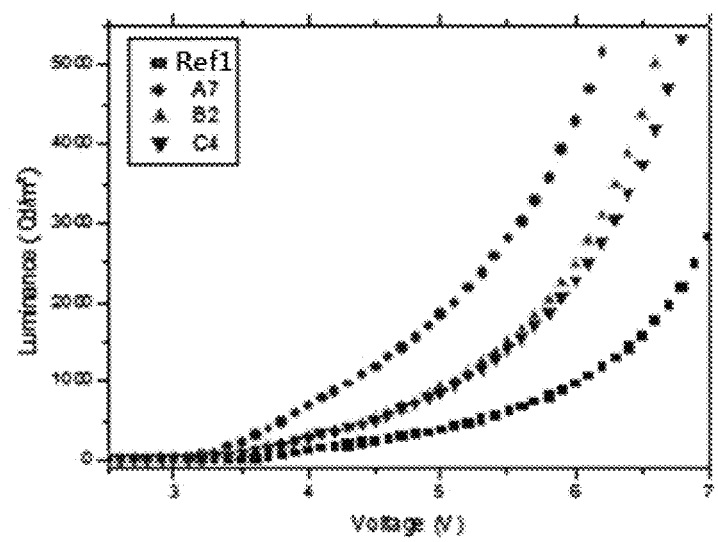
FIG. 11A, FIG. 11B and FIG. 11C are graphs showing the luminance of the organic light emitting diode including an organic compound in an exciton blocking layer.
Figure 11B:
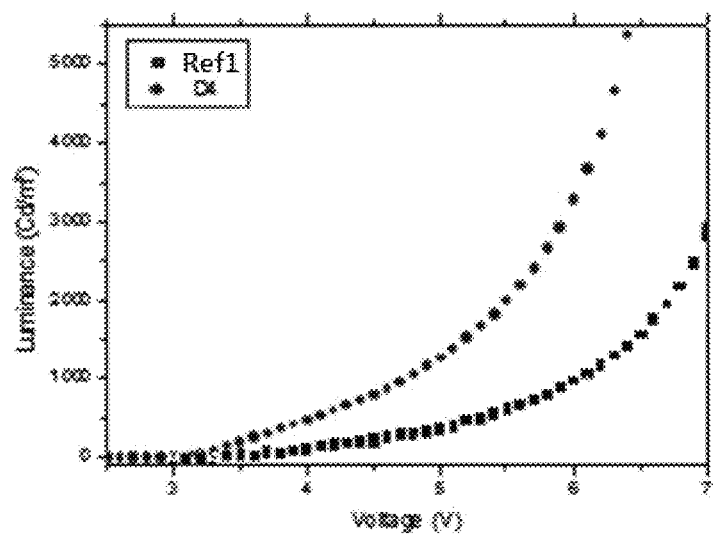
Figure 11C:
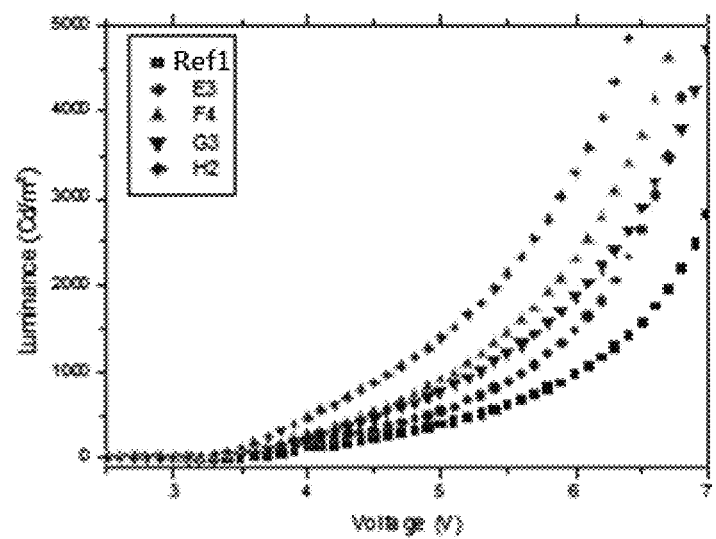
Figure 12A:
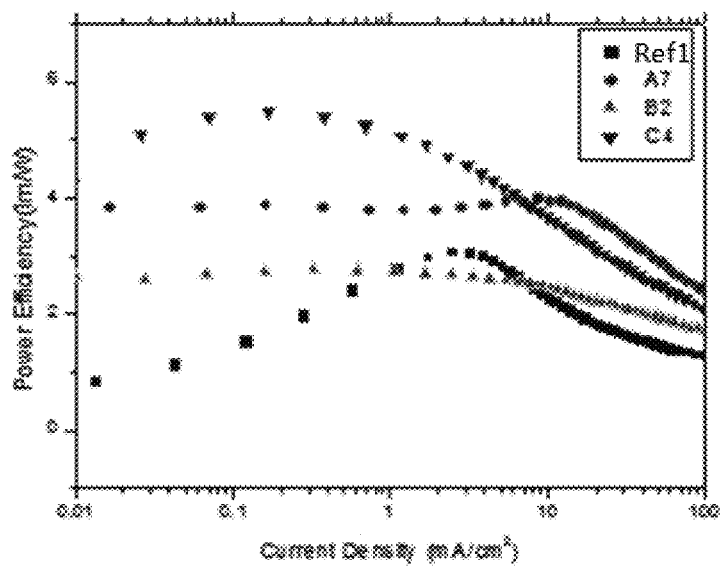
FIG. 12A, FIG. 12B and FIG. 12C are graphs showing the power efficiency (or emitting efficiency) of the organic light emitting diode including an organic compound in an exciton blocking layer.
Figure 12B:
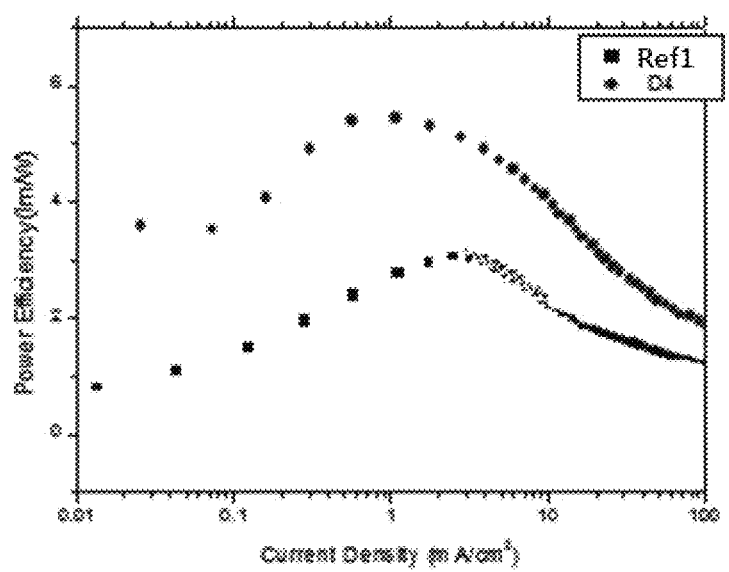
Figure 12C:
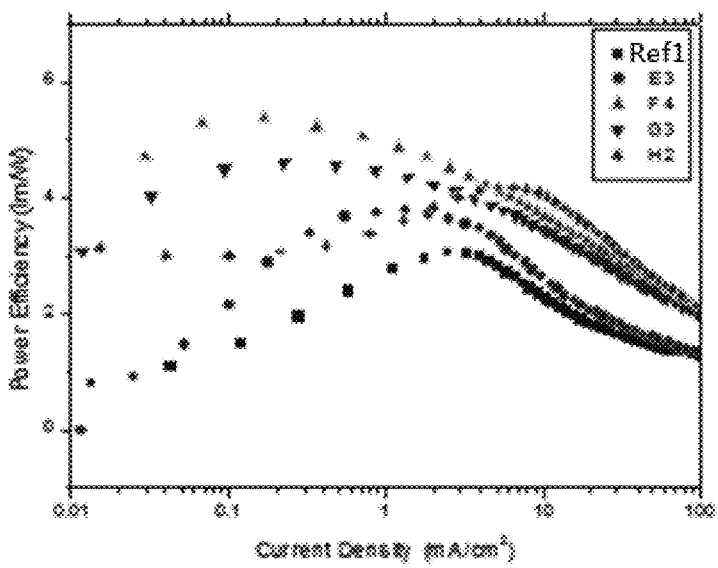
Figure 13A:
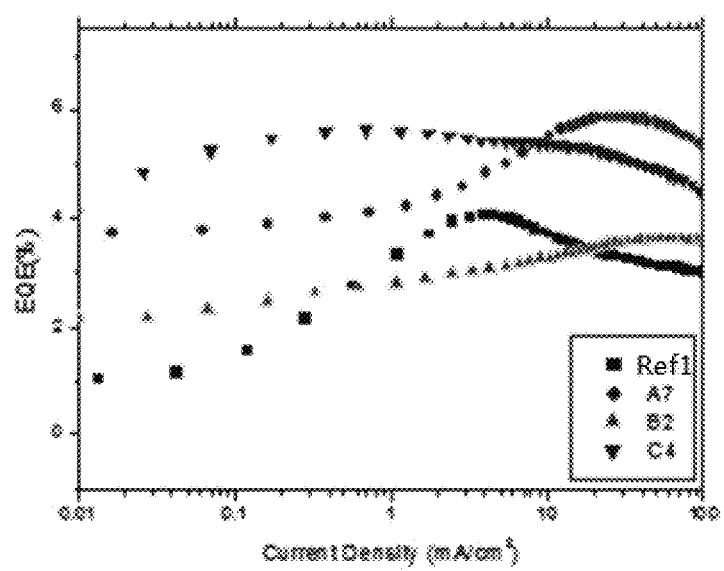
FIG. 13A, FIG. 13B and FIG. 13C are graphs showing the external quantum efficiency (EQE) of the organic light emitting diode including an organic compound in an exciton blocking layer.
Figure 13B:
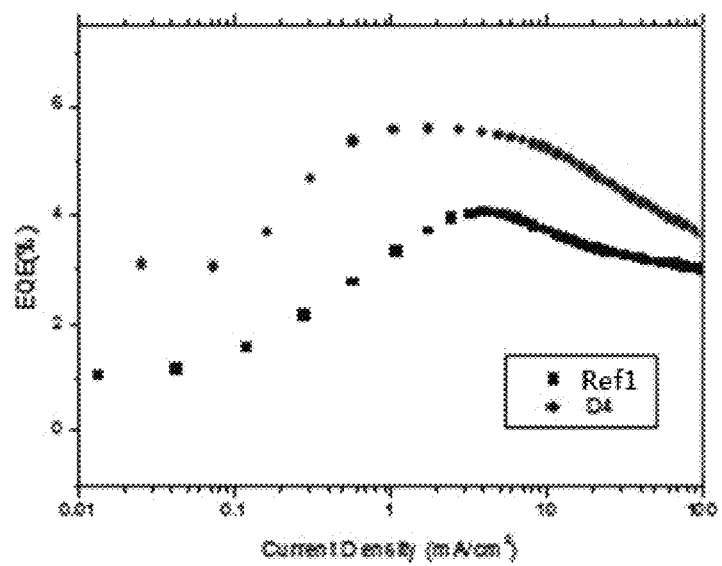
Figure 13C:
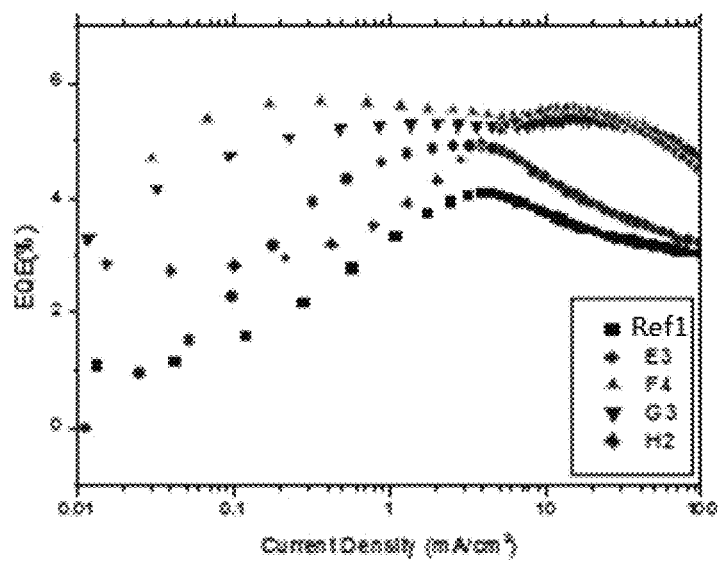
Figure 14A:
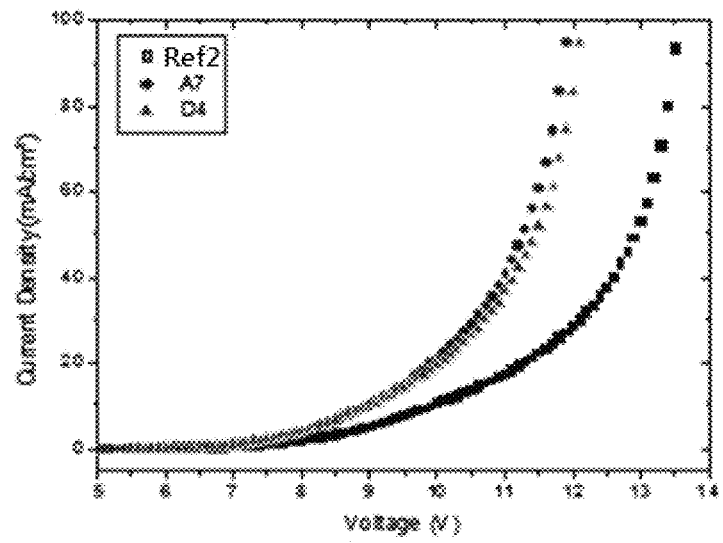
FIG. 14A, FIG. 14B, FIG. 14C and FIG. 14D are graphs showing emitting properties of a tandem structure organic light emitting diode including an organic compound in an upper exciton blocking layer.
Figure 14B:
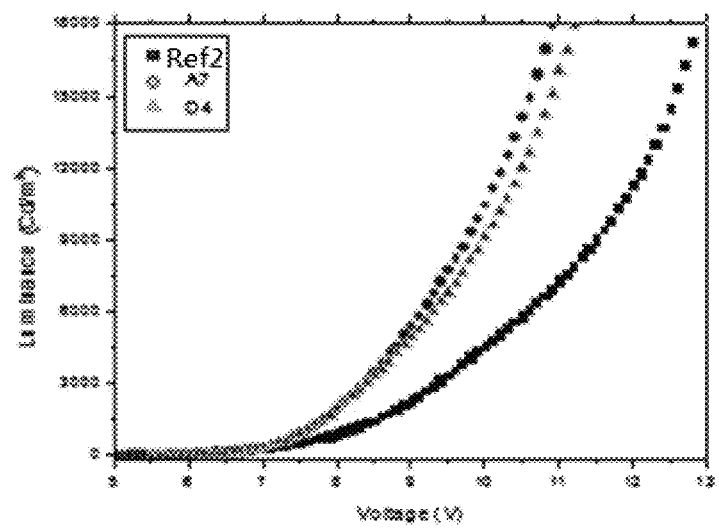
Figure 14C:
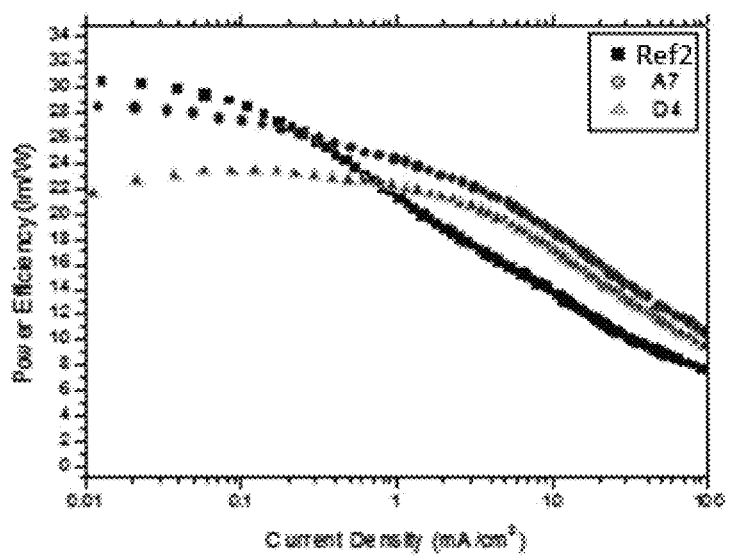
Figure 14D:
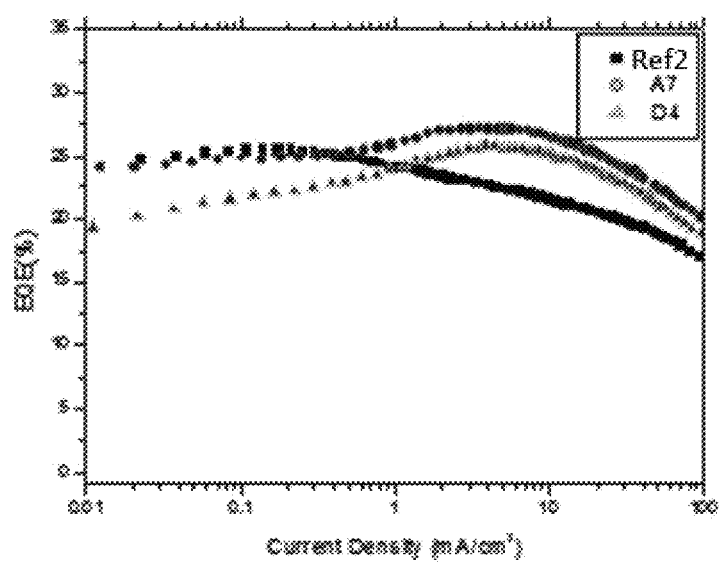
Figure 15A:
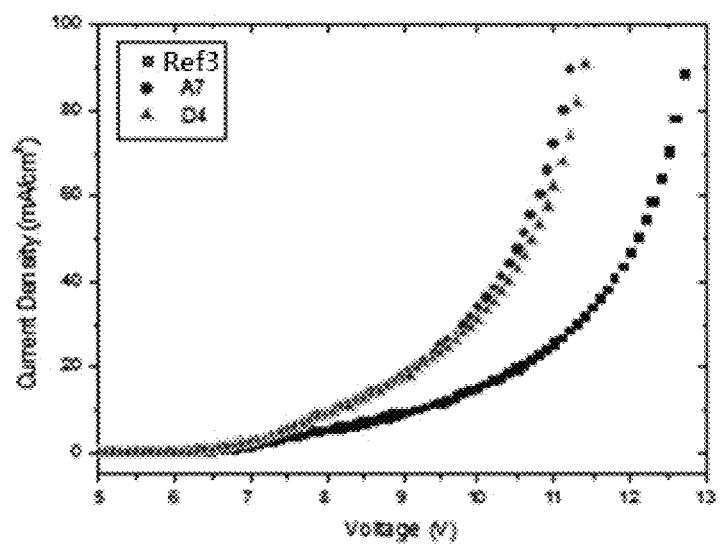
FIG. 15A, FIG. 15B, FIG. 15C and FIG. 15D are graphs showing emitting properties of a tandem structure organic light emitting diode including an organic compound in a charge generation layer and a hole transporting layer.
Figure 15B:
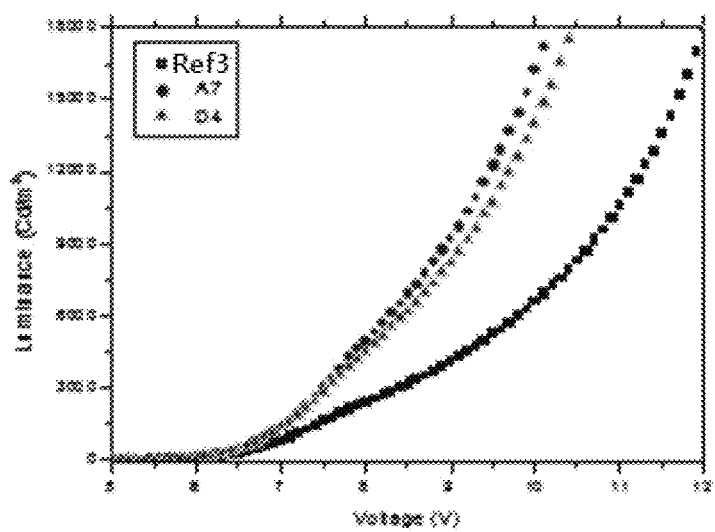
Figure 15C:
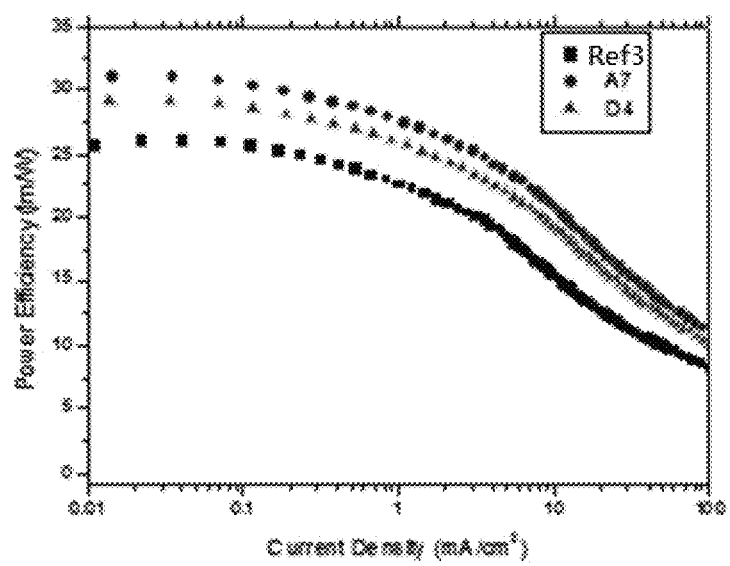
Figure 15D:
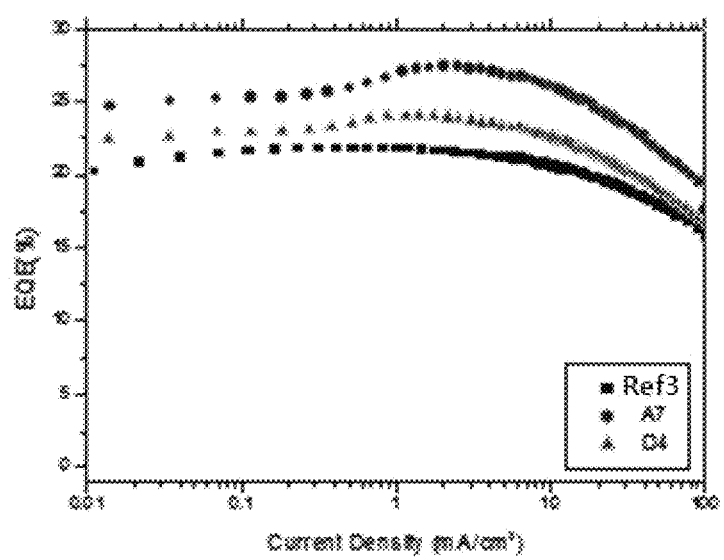

FIG. 9 is a schematic cross-sectional view of an OLED device according to the present invention.

As shown in FIG. 9, the OLED device 900 includes a driving thin film transistor (TFT) Td, a planarization layer 960 covering the driving TFT Td, an organic light emitting diode E on the planarization layer 960 and connected to the driving TFT Td.

The driving TFT Td includes a semiconductor layer 940, a gate electrode 944, a source electrode 956 and a drain electrode 958. The driving TFT Td in FIG. 9 has a coplanar structure.

A first substrate 901 and a second substrate 902 facing the first substrate 901 are attached to form a display panel. Each of the first substrate 901 and the second substrate 902 may be a glass substrate, a thin flexible substrate or a polymer plastic substrate. The first substrate 901, on which the driving TFT Td and the organic light emitting diode E are formed, may be referred to as an array substrate. The organic light emitting diode E is encapsuled by the second substrate 902 which may be referred to as an encapsulation substrate. For example, the first substrate 901 and the second substrate 902 may be attached to each other by an adhesive layer 980.

The semiconductor layer 940 is formed on the first substrate 901. The semiconductor layer 940 may be formed of an oxide semiconductor material. When the semiconductor layer 940 includes the oxide semiconductor material, a light-shielding pattern (not shown) may be formed under the semiconductor layer 940. The light to the semiconductor layer 940 is shielded or blocked by the light-shielding pattern such that thermal degradation of the semiconductor layer 940 can be prevented. On the other hand, when the semiconductor layer 940 includes polycrystalline silicon, impurities may be doped into both sides of the semiconductor layer 940.

A gate insulating layer 942 is formed on the semiconductor layer 940 and over an entire surface of the first substrate 901. The gate insulating layer 942 may be formed of an inorganic insulating material such as silicon oxide or silicon nitride.

The gate electrode 944, which is formed of a conductive material, e.g., metal, is formed on the gate insulating layer 942 to correspond to a center of the semiconductor layer 940. In addition, a gate line (not shown) and a first capacitor electrode (not shown) may be formed on the gate insulating layer 942. The gate line may extends along a first direction, and the first capacitor electrode may be connected to the gate electrode 944. The gate insulating layer 942 in FIG. 9 covers an entire surface of the first substrate 901. Alternatively, the gate insulating layer 942 may be patterned to have the same shape as the gate electrode 944.

An interlayer insulating layer 950, which is formed of an insulating material, is formed on an entire surface of the first substrate 901 including the gate electrode 944. The interlayer insulating layer 950 may be formed of an inorganic insulating material, e.g., silicon oxide or silicon nitride, or an organic insulating material, e.g., benzocyclobutene or photo-acryl.

The interlayer insulating layer 950 includes first and second semiconductor contact holes 952 and 954 exposing both sides of the semiconductor layer 940. The first and second semiconductor contact holes 952 and 954 are positioned at both sides of the gate electrode 944 to be spaced apart from the gate electrode 944. In FIG. 9, the first semiconductor contact hole 952 and the second semiconductor 954 are formed through the gate insulating layer 942 as well as the interlayer insulating layer 950. Alternatively, when the gate insulating layer 942 has the same shape as the gate electrode 944, the first semiconductor contact hole 952 and the second semiconductor contact hole 954 may be formed in the interlayer insulating layer 950 except the gate insulating layer 942.

The source electrode 956 and the drain electrode 958, which are formed of a conductive material, e.g., metal, are formed on the interlayer insulating layer 950. In addition, a data line (not shown) extending along a second direction, a power line (not shown) and a second capacitor electrode (not shown) may be formed on the interlayer insulating layer 950. The data line crosses the gate line to define a pixel region, and the power line is spaced apart from and parallel to the data line. The second capacitor electrode is connected to the drain electrode 958 and overlaps the first capacitor electrode to form a storage capacitor with the interlayer insulating layer 950.

The source electrode 956 and the drain electrode 958 are spaced apart from each other with respect to the gate electrode 944 and respectively contact both sides of the semiconductor layer 940 through the first and second semiconductor contact holes 952 and 954.

In the driving TFT Td, the gate electrode 944, the source electrode 956 and the drain electrode 958 are positioned over the semiconductor layer 940. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

A switching TFT (not shown) is formed on the first substrate 901. The switching TFT may have substantially the same structure as the driving TFT Td. The gate electrode 944 is connected to a drain electrode of the switching TFT, and the source electrode 956 is connected to the power line. A gate electrode and a source electrode of the switching TFT are connected to the gate line and the data line, respectively.

A planarization layer 960, which provides a flat top surface and includes a drain contact hole 962 exposing the drain electrode 958 of the driving TFT Td, is formed to cover the driving TFT Td. The drain contact hole 962 may be spaced apart from the second semiconductor contact hole 954 in a plane.

The organic light emitting diode E is disposed on the planarization layer 960 and includes a first electrode 910, an organic emitting layer 920 and a second electrode 930. The first electrode 910 is connected to the drain electrode 958 of the driving TFT Td, and the organic emitting layer 920 and the second electrode 930 are sequentially stacked on the first electrode 910. A bank 972 as a pixel definition layer is formed to cover an edge of the first electrode 910.

As mentioned above, the first electrode 910 as an anode includes a high work function conductive material, and the second electrode 930 as a cathode includes a low work function conductive material.

The second substrate 902 is attached to the first substrate 901 using the adhesive layer 980. Although not shown, a barrier layer for preventing the moisture and/or oxygen penetration into the organic light emitting diode E may be formed between the second substrate 902 and the organic light emitting diode E to cover the organic light emitting diode E.

As explained through FIGS. 1 to 8, the organic emitting layer 920 may include an HIL, an HTL, an EBL and a CGL with an EML, and at least of the HIL, the HTL, the EBL and the CGL includes the organic compound of the present invention. When the organic light emitting diode E has the tandem structure as those in FIGS. 5 to 8 as a white OLED, a color filter (not shown) may be formed under or over the organic light emitting diode E to provide a full-color image.

As mentioned above, the organic compound of the present invention has excellent hole transporting property. Accordingly, the organic compound of the present invention is used for the hole auxiliary layer (e.g., the HIL and/or the HTL) and the EBL. In this instance, the hole injection material or the hole transporting material may be doped into the organic compound such that the hole transporting property is further improved. In addition, in the tandem structure organic light emitting diode emitting the white light, the organic compound singly or in combination with the dopant is used for the P-CGL to provide the charge into adjacent emitting part. As a result, the driving voltage and the power consumption of the organic light emitting diode is reduced and the lifetime and the emitting efficiency of the organic light emitting diode is improved.

Synthesis

1. Synthesis of the Compound A7

(1) the Compound A3

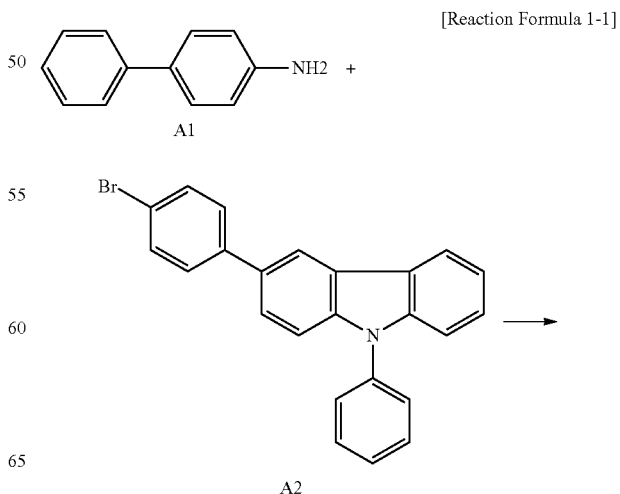

[Reaction Formula 1-1]

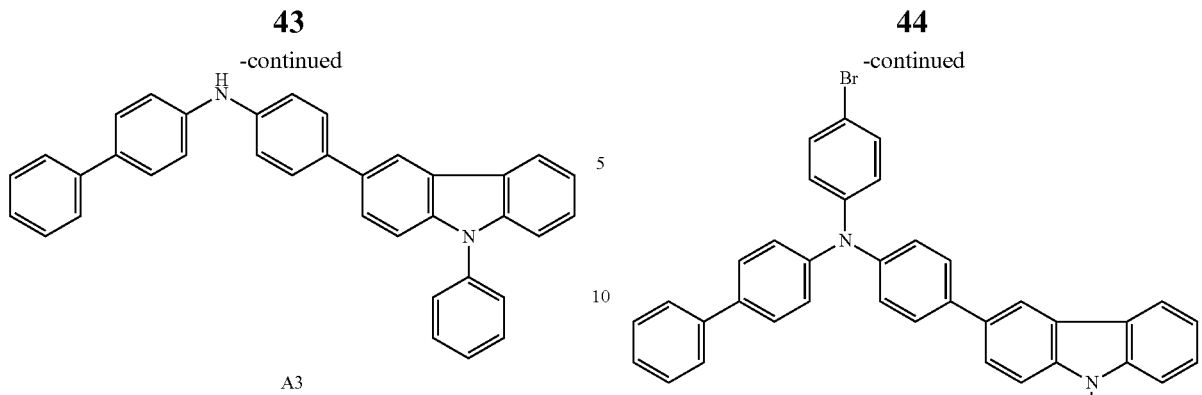

A3

In the 250 mL rounded-bottom flask, the compound A1 (3.00 g, 17.73 mmol), the compound A2 (7.77 g, 19.50 mmol), tris(dibenzylideneacetone) dipalladium(0) (0.24 g, 0.27 mmol), (±)-2,2'-bis(diphenylphosphino)-1,1'-binaphthalene(BINAP) (0.33 g, 0.53 mmol) and sodium tert-butoxide (2.39 g, 24.82 mmol) were dissolved in toluene (120 mL) and stirred in the bath of the temperature of 100° C. for 24 hrs. After the completion of the reaction, toluene was removed, and the resultant was extracted and distilled under the reduced pressure using dichloromethane and water. After the silica gel column, the solvent was distilled under the reduced pressure such that the compound A3 was obtained. (6.05 g, 12.43 mmol)

(2) the Compound A5

[Reaction Formula 1-2]

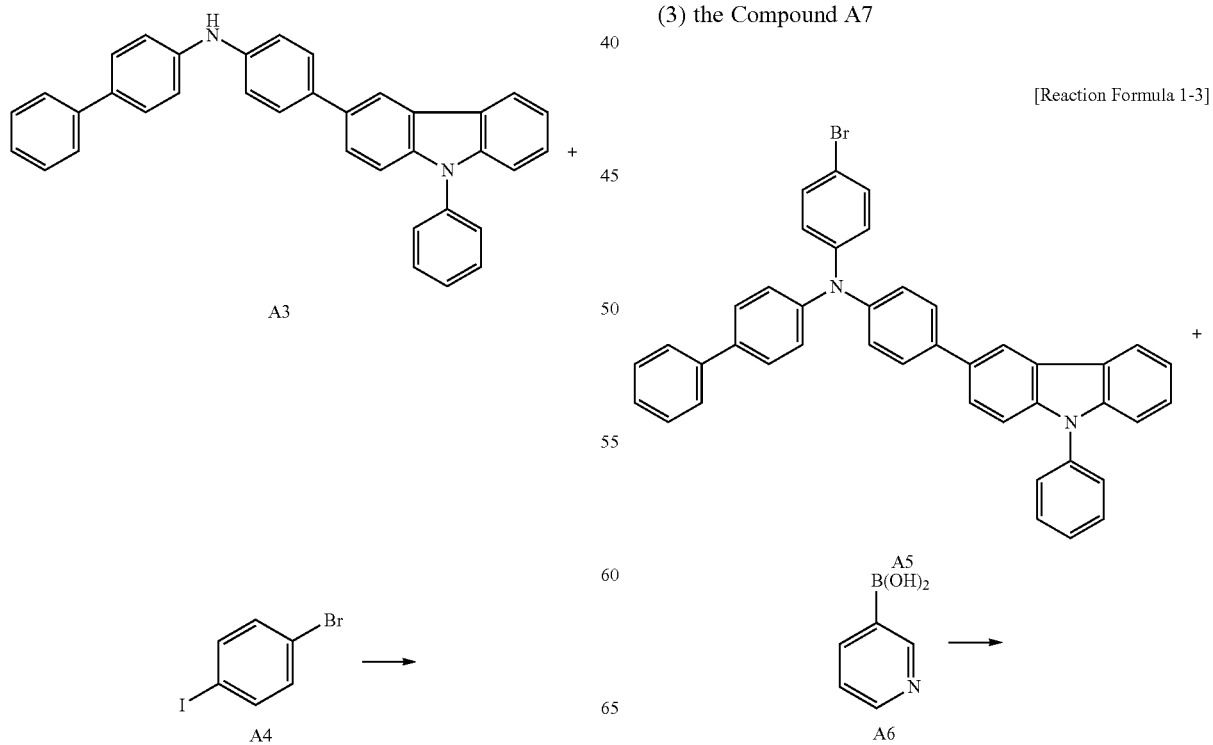

In the 250 mL rounded-bottom flask, the compound A3 (6.05 g, 12.43 mmol), the compound A4 (5.28 g, 18.65 mmol), 4,5-bis(diphenylphosphino)-9,9-dimethylxanthene (0.07 g, 0.12 mmol), palladium(II) acetate (0.03 g, 0.12 mmol) and sodium tert-butoxide(1.80 g, 18.77 mmol) were dissolved in toluene (120 mL) and stirred in the bath of the temperature of 100° C. for 24 hrs. After the completion of the reaction, toluene was removed, and the resultant was extracted and distilled under the reduced pressure using dichloromethane and water. After the silica gel column, the solvent was distilled under the reduced pressure such that the compound A5 was obtained. (7.21 g, 11.24 mmol)

(3) the Compound A7

[Reaction Formula 1-3]

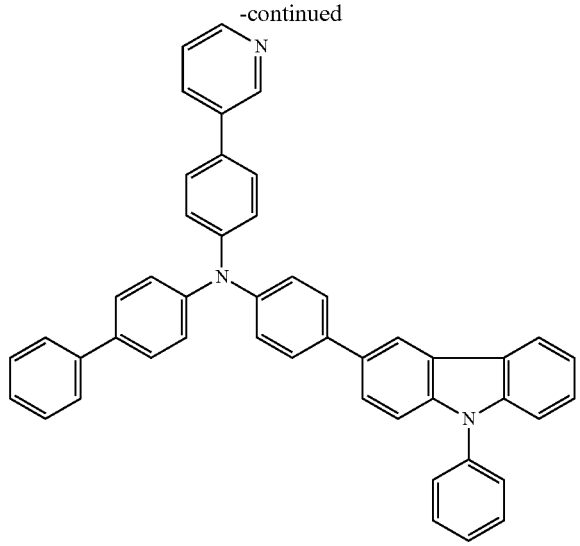

A7

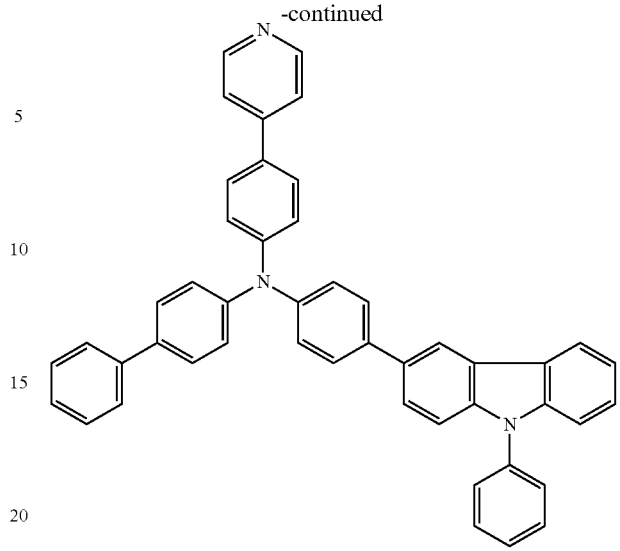

B2

In the 100 mL rounded-bottom flask, the compound A5 (2.00 g, 3.12 mmol), the compound A6 (0.42 g, 3.43 mmol), tetrakis(triphenylphosphine)palladium(0) (0.18 g, 0.16 mmol) and potassium carbonate (2.76 g, 20.00 mmol) were put into a mixture of toluene (40 mL), ethanol (20 mL) and water (10 mL) and stirred under the temperature of 100° C. for 24 hrs. After the completion of the reaction, the mixture was extracted and condensed using water and ethyl acetate. The mixture was separated by a column using ethyl acetate and n-hexane and precipitated using dichloromethane and petroleum ether. The precipitate was filtered such that the compound A7 was obtained. (1.36 g, 2.13 mmol)

1HNMR (500 MHz, CD2Cl2) 8.86 (s, 1H), 8.53~8.299 (m, 3H), 8.19 (d, 1H), 7.70~7.29 (m, 28H)

2. Synthesis of the Compound B2

In the 100 mL rounded-bottom flask, the compound A5 (2.00 g, 3.12 mmol), the compound B1 (0.42 g, 3.43 mmol), tetrakis(triphenylphosphine)palladium(0) (0.18 g, 0.16 mmol) and potassium carbonate (2.76 g, 20.00 mmol) were put into a mixture of toluene (40 mL), ethanol (20 mL) and water (10 mL) and stirred under the temperature of 100° C. for 24 hrs. After the completion of the reaction, the mixture was extracted and condensed using water and ethyl acetate. The mixture was separated by a column using ethyl acetate and n-hexane and precipitated using dichloromethane and petroleum ether. The precipitate was filtered such that the compound B2 was obtained. (1.28 g, 2.00 mmol)

1HNMR (500 MHz, CD2Cl2) 8.58 (d, 2H), 8.37 (s, 1H), 8.19 (d, 1H), 7.70~7.29 (m, 29H)

3. Synthesis of the Compound C4

(1) The Compound C3

[Reaction Formula 2]

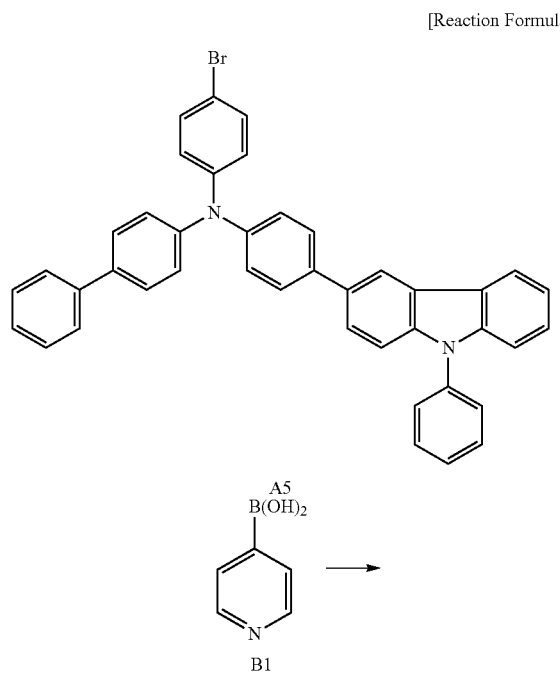

[Reaction Formula 3-1]

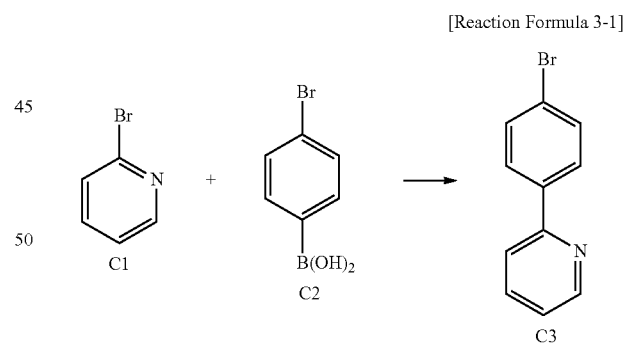

In the 250 mL rounded-bottom flask, the compound C1 (5.00 g, 31.65 mmol), the compound C2 (6.99 g, 34.81 mmol), tetrakis(triphenylphosphine)palladium(0) (1.83 g, 1.58 mmol) and potassium carbonate (8.29 g, 60.00 mmol) were put into a mixture of toluene (120 mL), ethanol (60 mL) and water (30 mL) and stirred under the temperature of 100° C. for 24 hrs. After the completion of the reaction, the mixture was extracted and condensed using water and ethyl acetate. The mixture was separated by a column using ethyl acetate and n-hexane and precipitated using dichloromethane and petroleum ether. The precipitate was filtered such that the compound C3 was obtained. (5.92 g, 25.29mmol)

(2) The Compound C4

4. Synthesis of the Compound D4
(1) The Compound D3

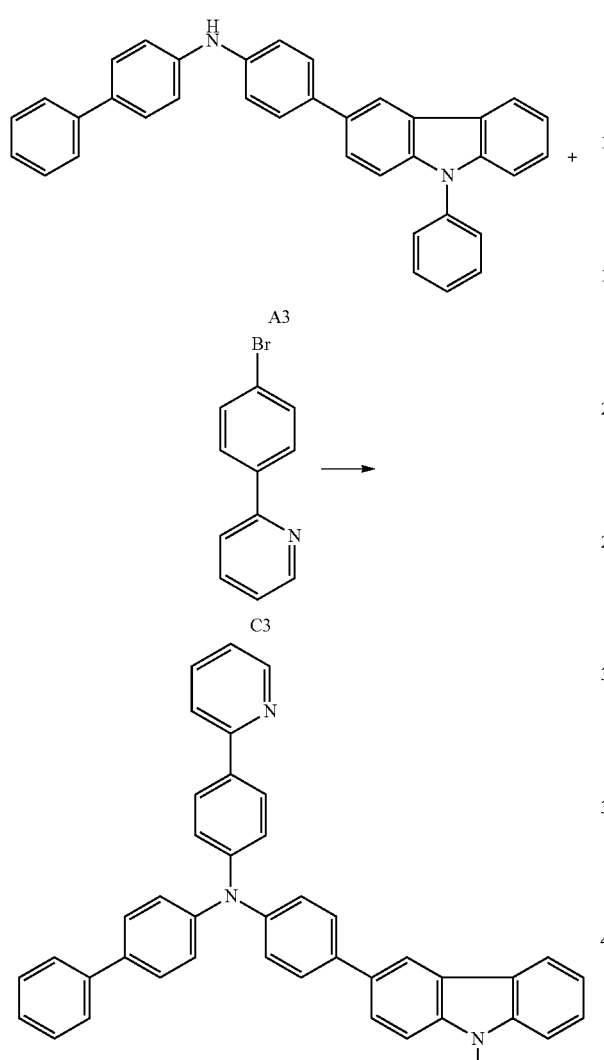

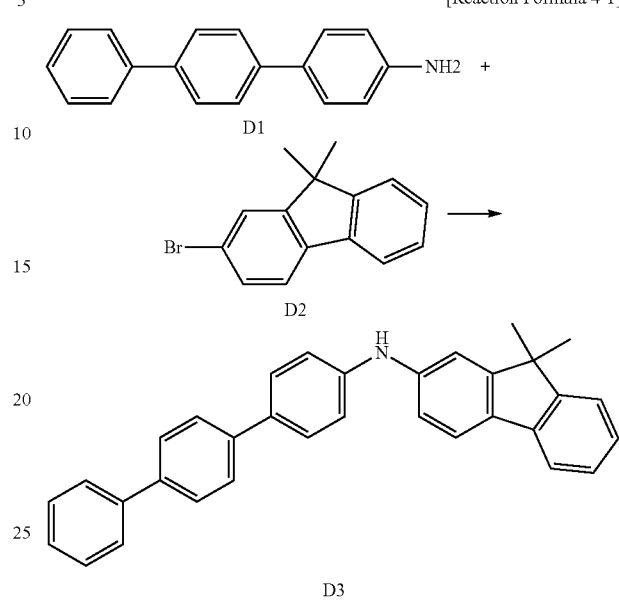

In the 250 mL rounded-bottom flask, the compound D1(3.00 g, 12.23 mmol), the compound D2 (3.22 g, 11.80 mmol), tris(dibenzylideneacetone) dipalladium(0) (0.17 g, 0.18 mmol), (±)-2,2'-bis(diphenylphosphino)-1,1'-binaphthalene(BINAP) (0.23 g, 0.37 mmol) and sodium tert-butoxide(1.65 g, 17.12 mmol) were dissolved in toluene (120 mL) and stirred in the bath of the temperature of 100° C. for 24 hrs. After the completion of the reaction, toluene was removed, and the resultant was extracted and distilled under the reduced pressure using dichloromethane and water. After the silica gel column, the solvent was distilled under the reduced pressure such that the compound D3 was obtained. (3.80 g, 8.68 mmol)

(2) The Compound D4

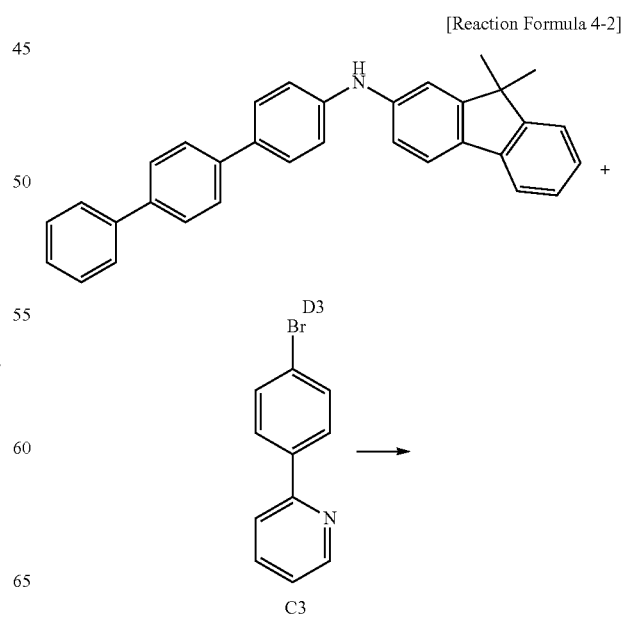

In the 100 mL rounded-bottom flask, the compound A3(2.00 g, 4.11 mmol), the compound C3 (1.06 g, 4.52 mmol), tris(dibenzylideneacetone) dipalladium(0) (0.06 g, 0.06 mmol), tri-tert-butylphosphine (0.02 g, 0.12 mmol) and sodium tert-butoxide (0.55 g, 5.75 mmol) were dissolved in toluene (40 mL) and stirred in the bath of the temperature of 100° C. for 24 hrs. After the completion of the reaction, toluene was removed, and the resultant was extracted and condensed using dichloromethane and water. The mixture was separated by a column using ethyl acetate and n-hexane and precipitated using dichloromethane and petroleum ether. The precipitate was filtered such that the compound C4 was obtained. (1.40 g, 2.18 mmol)

1HNMR (500 MHz, CD2Cl2) 8.63 (d, 1H), 8.37 (s, 1H), 8.19 (d, 1H), 7.97 (d, 2H), 7.73~7.23 (m, 28H)

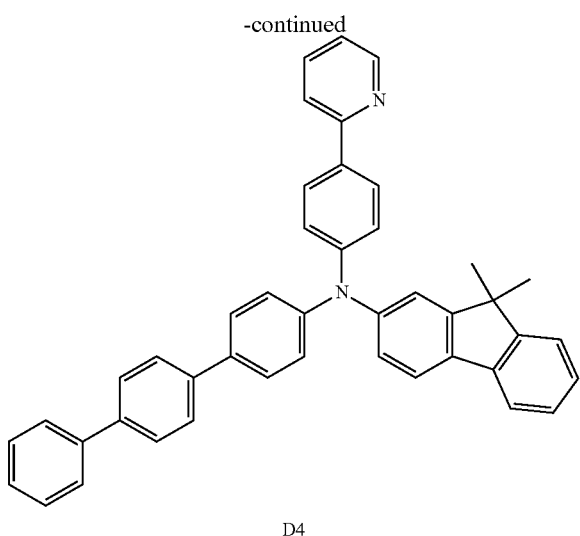

D4

In the 100 mL rounded-bottom flask, the compound D3(1.50 g, 3.43 mmol), the compound C3 (0.88 g, 3.77 mmol), tris(dibenzylideneacetone) dipalladium(0) (0.05 g, 0.05 mmol), tri-tert-butylphosphine (0.02 g, 0.10 mmol) and sodium tert-butoxide(0.46 g, 4.80 mmol) were dissolved in toluene (50 mL) and stirred in the bath of the temperature of 100° C. for 24 hrs. After the completion of the reaction, toluene was removed, and the resultant was extracted and condensed using dichloromethane and water. The mixture was separated by a column using ethyl acetate and n-hexane and precipitated using dichloromethane and petroleum ether. The precipitate was filtered such that the compound D4 was obtained. (1.15 g, 1.95mmol)

1HNMR (500 MHz, CD2Cl2) 8.62 (d, 1H), 7.95 (d, 2H), 7.73~7.58 (m, 12H), 7.46~7.11 (m, 13H), 1.42 (s, 6H)

5. Synthesis of the Compound E3
(1) The Compound E2

[Reaction Formula 5-1]

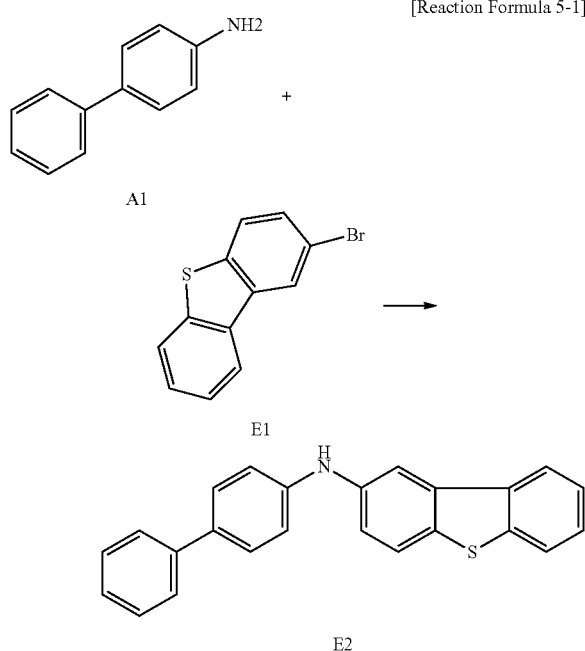

In the 250 mL rounded-bottom flask, the compound A1(2.00 g, 11.82 mmol), the compound E1 (3.42 g, 13.00 mmol), tris(dibenzylideneacetone) dipalladium(0) (0.16 g, 0.18 mmol), (±)-2,2'-bis(diphenylphosphino)-1,1'-binaphthalene(BINAP) (0.22 g, 0.35 mmol) and sodium tert-butoxide(1.59 g, 16.55 mmol) were dissolved in toluene (110 mL) and stirred in the bath of the temperature of 100° C. for 24 hrs. After the completion of the reaction, toluene was removed, and the resultant was extracted and distilled under the reduced pressure using dichloromethane and water. After the silica gel column, the solvent was distilled under the reduced pressure such that the compound E2 was obtained. (3.05 g, 8.68 mmol)

(2) The Compound E3

[Reaction Formula 5-2]

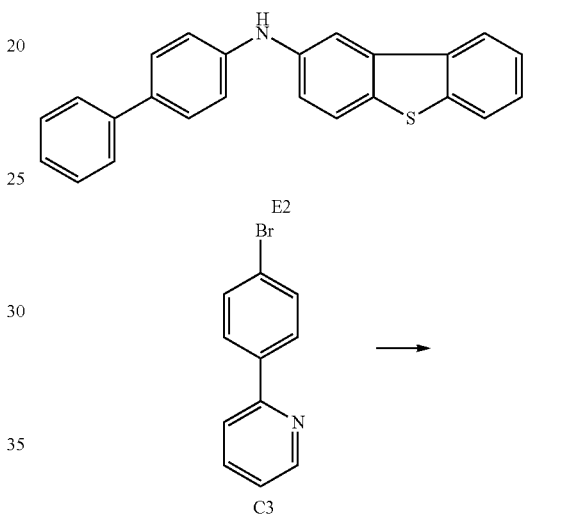

In the 100 mL rounded-bottom flask, the compound E3(1.50 g, 4.27 mmol), the compound C3 (1.10 g, 4.69 mmol), tris(dibenzylideneacetone) dipalladium(0) (0.06 g, 0.06 mmol), tri-tert-butylphosphine (0.03 g, 0.13 mmol) and sodium tert-butoxide(0.57 g, 5.98 mmol) were dissolved in toluene (50 mL) and stirred in the bath of the temperature of 100° C. for 24 hrs. After the completion of the reaction, toluene was removed, and the resultant was extracted and condensed using dichloromethane and water. The mixture was separated by a column using ethyl acetate and n-hexane and precipitated using dichloromethane and petroleum ether.

The precipitate was filtered such that the compound E3 was obtained. (1.21 g, 2.40 mmol)

1HNMR (500 MHz, CD2Cl2) 8.62 (d, 1H), 8.01~7.94 (m, 4H), 7.85~7.73 (m, 4H), 7.60~7.20 (m, 15H)

6. Synthesis of the Compound F4

(1) The Compound F2

[Reaction Formula 6-1]

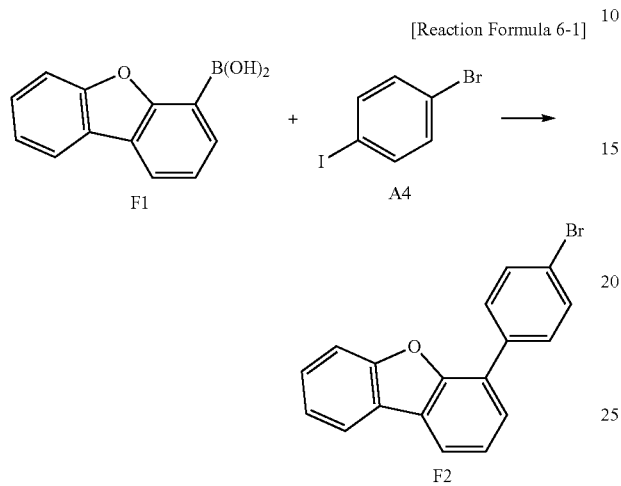

In the 250 mL rounded-bottom flask, the compound F 1 (3.00 g, 14.15 mmol), the compound A4 (4.00 g, 14.15 mmol), tetrakis(triphenylphosphine)palladium(0) (0.82 g, 0.71 mmol) and potassium carbonate (4.84 g, 35.00 mmol) were put into a mixture of toluene (70 mL), ethanol (35 mL) and water (17.5 mL) and stirred under the temperature of 100° C. for 24 hrs. After the completion of the reaction, the mixture was extracted and condensed using water and dichloromethane. The mixture was separated by a column using dichloromethane and n-hexane and precipitated using dichloromethane and petroleum ether. The precipitate was filtered such that the compound F2 was obtained. (5.92 g, 25.29 mmol)

(2) The Compound F3

[Reaction Formula 6-2]

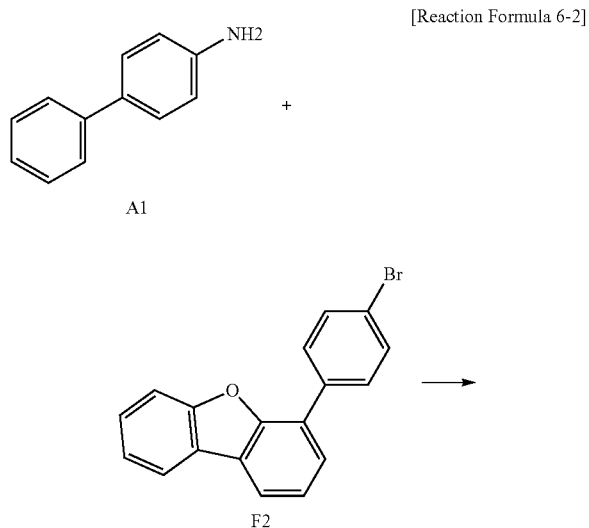

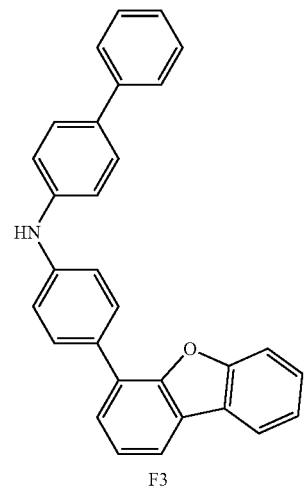

In the 250 mL rounded-bottom flask, the compound A1 (1.80 g, 10.64 mmol), the compound F2 (3.78 g, 11.70 mmol), tris(dibenzylideneacetone) dipalladium(0) (0.15 g, 0.16 mmol), (±)-2,2'-bis(diphenylphosphino)-1,1'-binaphthalene(BINAP) (0.20 g, 0.32 mmol) and sodium tert-butoxide(1.43 g, 14.89 mmol) were dissolved in toluene (100 mL) and stirred in the bath of the temperature of 100° C. for 24 hrs. After the completion of the reaction, toluene was removed, and the resultant was extracted and distilled under the reduced pressure using dichloromethane and water. After the silica gel column, the solvent was distilled under the reduced pressure such that the compound F3 was obtained. (3.05 g, 7.41 mmol)

(3) The Compound F4

[Reaction Formula 6-3]

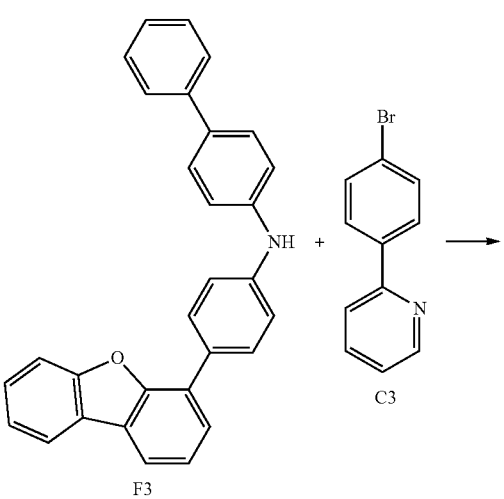

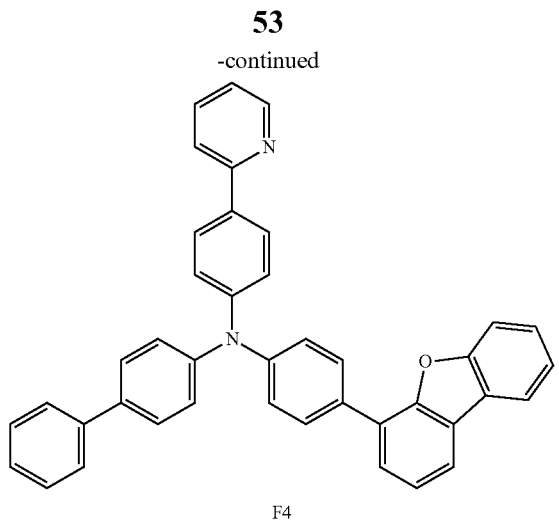

F4

In the 100 mL rounded-bottom flask, the compound F3(1.50 g, 3.65 mmol), the compound C3(0.94 g, 4.01 mmol), tris(dibenzylideneacetone) dipalladium(0) (0.05 g, 0.05 mmol), tri-tert-butylphosphine (0.02 g, 0.11 mmol) and sodium tert-butoxide(0.49 g, 5.10 mmol) were dissolved into toluene (100 mL) and stirred in the bath of the temperature of 100° C. for 24 hrs. After the completion of the reaction, toluene was removed, and the resultant was extracted and condensed using dichloromethane and water. The mixture was separated by a column using ethyl acetate and n-hexane and precipitated using dichloromethane and petroleum ether. The precipitate was filtered such that the compound F4 was obtained. (1.32 g, 2.34 mmol)

1HNMR (500 MHz, CD2Cl2) 8.64 (d, 1H), 8.01~7.88 (m, 6H), 7.75 (m, 2H), 7.63~7.57 (m, 6H), 7.49~7.21 (m, 13H)

7. Synthesis of the Compound G3
(1) The Compound G2

[Reaction Formula 7-1]

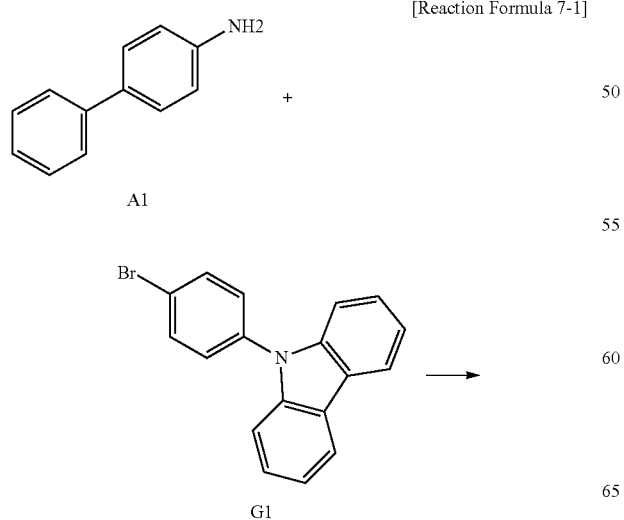

A1

+

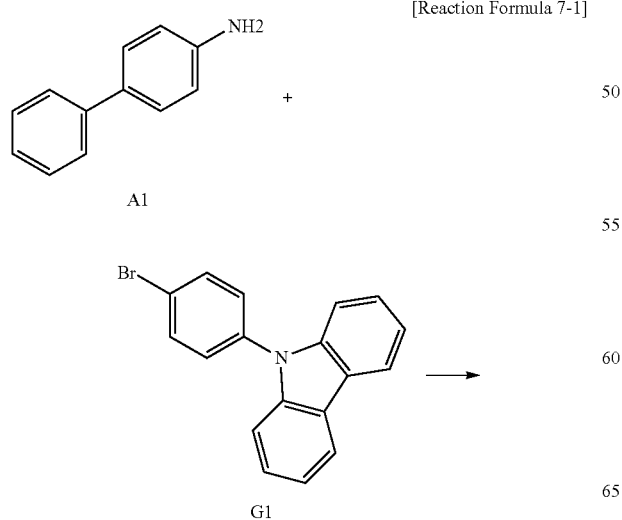

G1

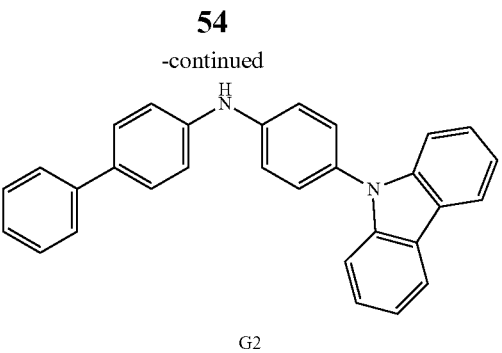

G2

In the 500 mL rounded-bottom flask, the compound A1(5.00 g, 29.55 mmol), the compound G1 (10.47 g, 32.50 mmol), tris(dibenzylideneacetone) dipalladium(0) (0.41 g, 0.44 mmol), (±)-2,2'-bis(diphenylphosphino)-1,1'-binaphthalene(BINAP) (0.55 g, 0.89 mmol) and sodium tert-butoxide(3.98 g, 41.37 mmol) were dissolved in toluene (250 mL) and stirred in the bath of the temperature of 100° C. for 24 hrs. After the completion of the reaction, toluene was removed, and the resultant was extracted and distilled under the reduced pressure using dichloromethane and water. After the silica gel column, the solvent was distilled under the reduced pressure such that the compound G2 was obtained. (7.53 g, 18.34 mmol)

(2) The Compound G3

[Reaction Formula 7-2]

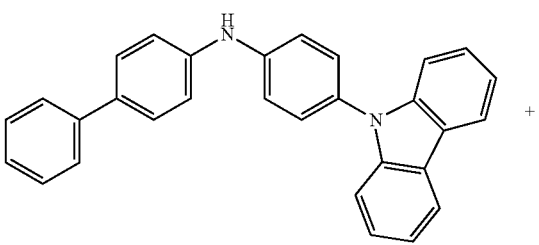

G2

+

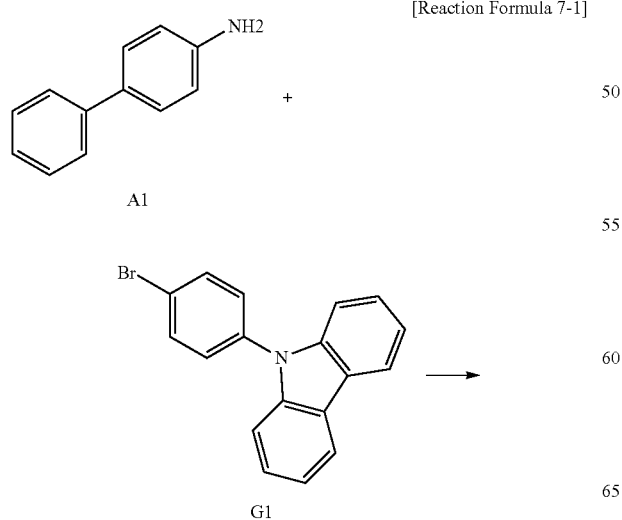

C3

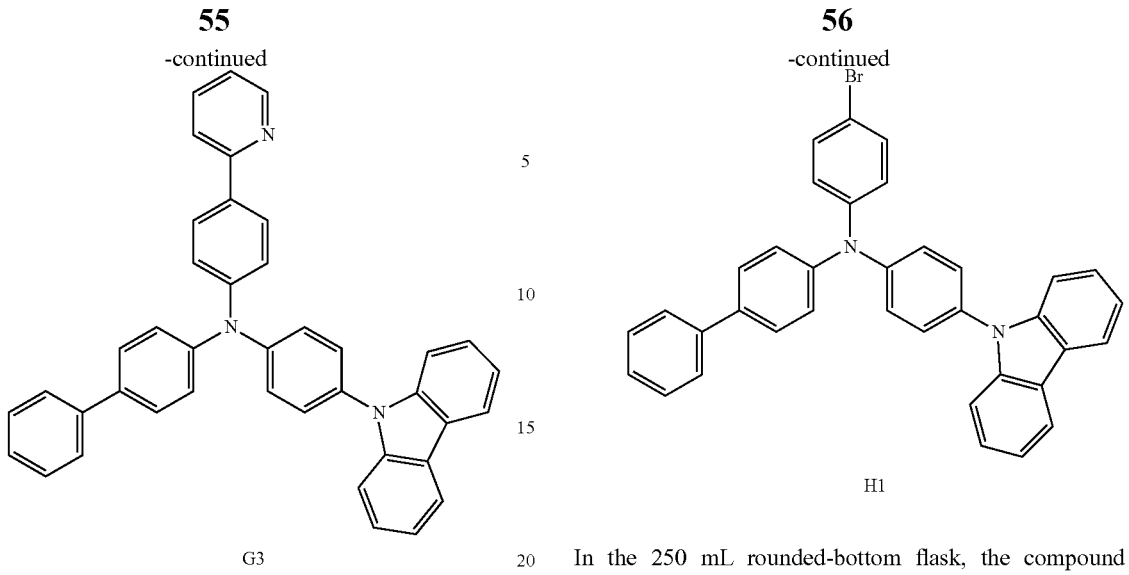

G3

In the 100 mL rounded-bottom flask, the compound G2(1.50 g, 3.65 mmol), the compound C3 (0.94 g, 4.02 mmol), tris(dibenzylideneacetone) dipalladium(0) (0.05 g, 0.05 mmol), tri-tert-butylphosphine (0.02 g, 0.11 mmol) and sodium tert-butoxide(0.49 g, 5.12 mmol) were dissolved into toluene (40 mL) and stirred in the bath of the temperature of 100° C. for 24 hrs. After the completion of the reaction, toluene was removed, and the resultant was extracted and condensed using dichloromethane and water. The mixture was separated by a column using ethyl acetate and n-hexane and precipitated using dichloromethane and petroleum ether. The precipitate was filtered such that the compound G3 was obtained. (0.98 g, 1.74 mmol)

1HNMR (500 MHz, CD2Cl2) 8.65 (d, 1H), 8.14 (d, 2H), 8.0 (d, 2H), 7.77~7.76 (m, 2H), 7.62~7.58 (m, 4H), 7.49~7.33 (m, 18H)

8. Synthesis of the Compound H2

(1) The Compound H1

In the 250 mL rounded-bottom flask, the compound G2(2.00 g, 4.87 mmol), the compound A4 (2.07 g, 7.31 mmol), 4,5-bis(diphenylphosphino)-9,9-dimethylxanthene (0.03 g, 0.05 mmol), palladium(II) acetate (0.01 g, 0.05 mmol) and sodium tert-butoxide(0.71 g, 7.36 mmol) were dissolved in toluene (50 mL) and stirred in the bath of the temperature of 100° C. for 24 hrs. After the completion of the reaction, toluene was removed, and the resultant was extracted and distilled under the reduced pressure using dichloromethane and water. After the silica gel column, the solvent was distilled under the reduced pressure such that the compound H1 was obtained. (2.24 g, 3.96 mmol)

(2) The Compound H2

[Reaction Formula 8-1]

[Reaction Formula 8-2]

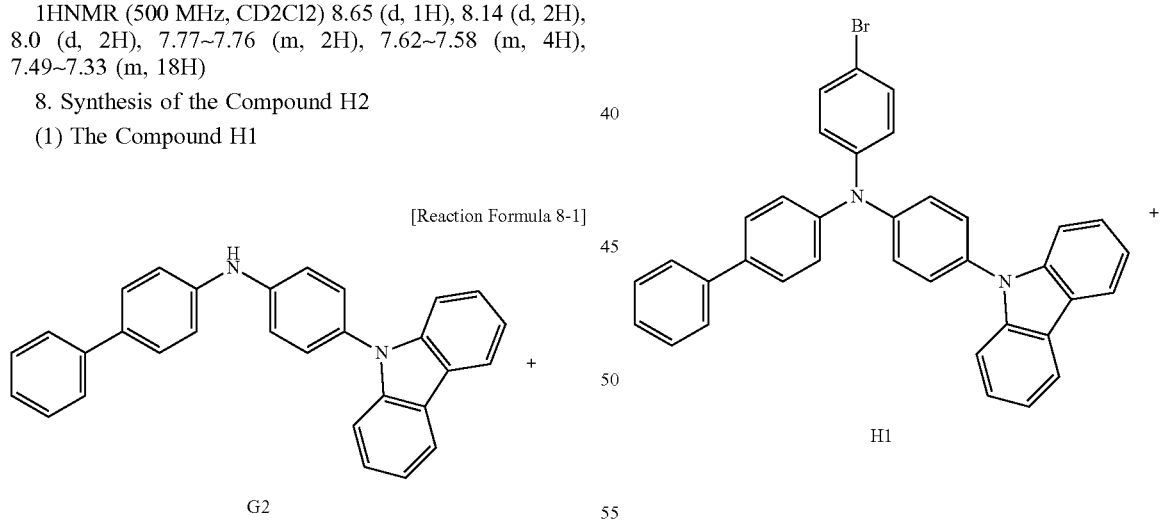

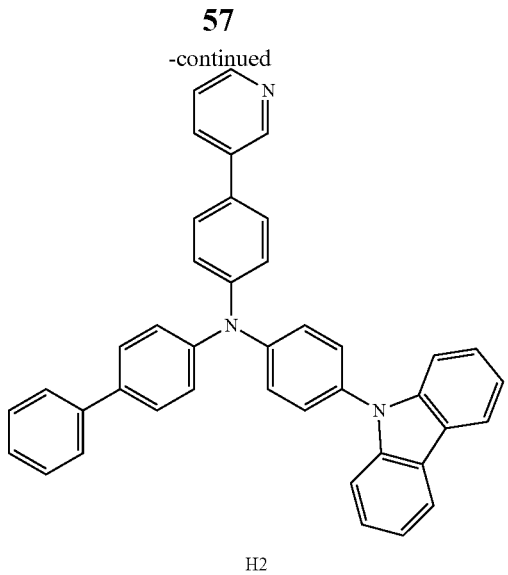

H2

In the 100 mL rounded-bottom flask, the compound H1 (2.00 g, 3.54 mmol), the compound A6 (0.48 g, 3.89 mmol), tetrakis(triphenylphosphine)palladium(0) (0.20 g, 0.18 mmol) and potassium carbonate (2.76 g, 20.00 mmol) were dissolved into a mixture of toluene (40 mL), ethanol (20 mL) and water (10 mL) and stirred under the temperature of 100° C. for 24 hrs. After the completion of the reaction, the resultant was extracted and condensed using water and ethyl acetate. The mixture was separated by a column using ethyl acetate and n-hexane and precipitated using dichloromethane and petroleum ether. The precipitate was filtered such that the compound H2 was obtained. (1.54 g, 2.41 mmol)

1HNMR (500 MHz, CD2Cl2) 8.65 (d, 1H), 8.14 (d, 2H), 8.03 (d, 2H), 7.77~7.76 (m, 2H), 7.62~7.58 (m, 4H), 7.49~7.33 (m, 18H).

Organic Light Emitting Diode

1. EXAMPLE 1 (EX1)

An ITO layer is patterned to form the anode (3 mm*3 mm), and the anode is washed. The anode is loaded in a vacuum chamber having a base pressure of 1*10−6, and layers are sequentially deposited as below.

(1) HIL: (HAT-CN, 50 Å),
(2) HTL: (α-NPB, 1000 Å),
(3) EBL: (compound A7, 150 Å),
(4) blue EML: (host (MADN) doped by dopant (BD-1, 4 wt %), 250 Å),
(5) first ETL: (2-[4-(9,10-Di-2-naphthalenyl-2-anthracenyl)phenyl]-1-phenyl-1H-benzimidazole, 100~300 Å),
(6) second ETL (Bphen doped by Li (2 wt %), 100 Å),
(7) EIL (LiF, 5~10 Å) and
(8) cathode (Al, 800~1000 Å).

The deposited structure is loaded in the drying box and encapsuled by an UV-cured expoxy and a getter. The organic light emitting diode has an emitting area of 9 mm2.

2. EXAMPLE 2 (EX2)
Instead of the compound A7, the compound B2 is used.
3. EXAMPLE 3 (EX3)
Instead of the compound A7, the compound C4 is used.
4. EXAMPLE 4 (EX4)
Instead of the compound A7, the compound D4 is used.
5. EXAMPLE 5 (EX5)
Instead of the compound A7, the compound E3 is used.
6. EXAMPLE 6 (EX6)
Instead of the compound A7, the compound F4 is used.
7. EXAMPLE 7 (EX7)
Instead of the compound A7, the compound G3 is used.
8. EXAMPLE 8 (EX8)
Instead of the compound A7, the compound H2 is used.
9. COMPARATIVE EXAMPLE 1 (REF1)
Instead of the compound A7, the compound TCTA is used.

The EL property of the organic light emitting diode in "Example 1" to "Example 8" and "Comparative Example 1" is measured using the current supply "KEITHLEY" and the photometer "PR 650" under the room temperature. The driving voltage, the luminance, the power efficiency, the external quantum efficiency (EQE) and the color coordinate index of the organic light emitting diodes of are measured and listed in Table 1. The current density, the luminance, the power efficiency and the EQE are shown in FIGS. 10A to 13C.

TABLE 1

|  |  | V | Cd/A | lm/W | EQE (%) | CIE_x | CIE_y |
|---|---|---|---|---|---|---|---|
| Ex1 | A7 | 3.78 | 4.88 | 4.05 | 5.64 | 0.142 | 0.112 |
| Ex2 | B2 | 4.07 | 3.18 | 2.46 | 3.32 | 0.142 | 0.115 |
| Ex3 | C4 | 4.50 | 5.20 | 3.63 | 5.34 | 0.140 | 0.117 |
| Ex4 | D4 | 4.03 | 5.29 | 4.12 | 5.40 | 0.140 | 0.119 |
| Ex5 | E3 | 4.22 | 4.28 | 3.18 | 4.87 | 0.141 | 0.104 |
| Ex6 | F4 | 4.54 | 5.23 | 3.62 | 5.45 | 0.140 | 0.115 |
| Ex7 | G3 | 4.55 | 4.92 | 3.40 | 5.30 | 0.140 | 0.110 |
| Ex8 | H2 | 4.04 | 5.27 | 4.10 | 5.62 | 0.141 | 0.112 |
| Ref1 | TCTA | 4.90 | 3.28 | 2.10 | 3.43 | 0.145 | 0.115 |

As shown in Table 1 and FIGS. 10A to 13C, in comparison to "Comparative Example 1", the driving voltage of the organic light emitting diode of the present invention (Ex 1 to Ex 8) is reduced (about 23%), the power efficiency of the organic light emitting diode of the present invention (Ex 1 to Ex 8) is improved (about 96%). In addition, the EQE of the organic light emitting diode of the present invention (Ex 1 to Ex 8) is improved (about 94%).

Namely, by using the organic compound of the present invention in the EBL, there are advantages in the driving voltage, the luminance, the power efficiency and/or the EQE.

Tandem Structure Organic Light Emitting Diode

1. EXAMPLE 9 (EX9)

An ITO layer is patterned to form the anode (3 mm*3 mm), and the anode is washed. The anode is loaded in a vacuum chamber having a base pressure of 1*10−6, and layers are sequentially deposited as below.

(1) HIL: (HAT-CN, 50 Å),
(2) first HTL: (α-NPB, 1000 Å),
(3) first EBL: (TCTA, 150 Å),
(4) first EML (blue): (host (MADN) doped by dopant (BD-1, 4 wt %), 250 Å),
(5) first ETL: (2-[4-(9,10-Di-2-naphthalenyl-2-anthracenyl)phenyl]-1-phenyl-1H-benzimidazole, 100~300 Å),
(6) N-CGL: (Bphene doped by Li (2 wt %), 100 Å),
(7) P-CGL: (HAT-CN, 100 Å),
(8) second HTL: (α-NPB, 100 Å),
(9) second EBL: (compound A7, 100 Å),
(10) second EML (YG): (CBP doped by Ir(2-phq)$_3$, 300 Å),
(11) second ETL: (2-[4-(9,10-Di-2-naphthalenyl-2-anthracenyl)phenyl]-1-phenyl-1H-benzimidazole, 350~400 Å),
(12) EIL (LiF, 5~10 Å) and
(13) cathode (Al, 800~1000 Å).

The deposited structure is loaded in the drying box and encapsuled by an UV-cured expoxy and a getter. The organic light emitting diode has an emitting area of 9 mm2.

2. EXAMPLE 10 (EX10)

Instead of the compound A7, the compound D4 is used.

3. COMPARATIVE EXAMPLE 2 (REF2)

Instead of the compound A7, the compound TCTA is used.

The EL property of the organic light emitting diode in "Example 9", "Example 10" and "Comparative Example 2" is measured using the current supply "KEITHLEY" and the photometer "PR 650" under the room temperature. The driving voltage, the luminance, the power efficiency, the external quantum efficiency (EQE) and the color coordinate index of the organic light emitting diodes of are measured and listed in Table 2. The current density, the luminance, the power efficiency and the EQE are shown in FIGS. 14A to 14D.

TABLE 2

|  |  | V | Cd/A | lm/W | EQE (%) | CIE_x | CIE_y |
|---|---|---|---|---|---|---|---|
| Ex9 | A7 | 9.07 | 52.67 | 18.24 | 26.09 | 0.316 | 0.335 |
| Ex10 | D4 | 9.09 | 48.99 | 16.93 | 24.78 | 0.312 | 0.327 |
| Ref2 | TCTA | 9.87 | 43.38 | 13.80 | 21.11 | 0.341 | 0.342 |

As shown in Table 2 and FIGS. 14A to 14D, in comparison to "Comparative Example 2", the driving voltage of the organic light emitting diode of the present invention (Ex 9 and Ex 10) is reduced (about 8%), the power efficiency of the organic light emitting diode of the present invention (Ex 9 and Ex 10) is improved (about 32%). In addition, the EQE of the organic light emitting diode of the present invention (Ex 9 and Ex 10) is improved (about 24%).

Namely, by using the organic compound of the present invention in the second EBL, there are advantages in the driving voltage, the luminance, the power efficiency and/or the EQE.

4. EXAMPLE 11 (EX11)

An ITO layer is patterned to form the anode (3 mm*3 mm), and the anode is washed. The anode is loaded in a vacuum chamber having a base pressure of $1*10-6$, and layers are sequentially deposited as below.

(1) HIL : (HAT-CN, 50 Å), (2) first HTL: (α-NPB, 1000 Å), (3) first EBL: (TCTA, 150 Å), (4) first EML (blue): (host (MADN) doped by dopant (BD-1, 4 wt %), 250 Å), (5) first ETL: (2-[4-(9,10-Di-2-naphthalenyl-2-anthracenyl)phenyl]-1-phenyl-1H-benzimidazole, 100~300 Å), (6) N-CGL: (Bphene doped by Li (2 wt %), 100 Å), (7) P-CGL: (the compound A7 doped by F4TCNQ (10 wt %), 100 Å), (8) second HTL: (the compound A7, 100 Å), (9) second EML (YG): (CBP doped by $Ir(2-phq)_3$, 300 Å),

(10) second ETL: (2-[4-(9,10-Di-2-naphthalenyl-2-anthracenyl)phenyl]-1-phenyl-1H-benzimidazole, 350~400 Å),

(11) EIL (LiF, 5~10 Å) and

(12) cathode (Al, 800Å1000 Å).

The deposited structure is loaded in the drying box and encapsuled by an UV-cured expoxy and a getter. The organic light emitting diode has an emitting area of 9 mm2.

5. EXAMPLE 12 (EX12)

Instead of the compound A7 in the P-CGL and the second HTL, the compound D4 is used.

6. COMPARATIVE EXAMPLE 3 (REF3)

Instead of the compound A7 in the P-CGL and the second HTL, the compound α-NPB is used.

The EL property of the organic light emitting diode in "Example 11", "Example 12" and "Comparative Example 3" is measured using the current supply "KEITHLEY" and the photometer "PR 650" under the room temperature. The driving voltage, the luminance, the power efficiency, the external quantum efficiency (EQE) and the color coordinate index of the organic light emitting diodes of are measured and listed in Table 3. The current density, the luminance, the power efficiency and the EQE are shown in FIGS. 15A to 15D.

TABLE 3

|  |  | V | Cd/A | lm/W | EQE (%) | CIE_x | CIE_y |
|---|---|---|---|---|---|---|---|
| Ex11 | A7 | 8.14 | 53.19 | 20.54 | 25.58 | 0.318 | 0.333 |
| Ex12 | D4 | 8.18 | 49.44 | 18.99 | 22.38 | 0.343 | 0.364 |
| Ref3 | α-NPB | 9.25 | 44.8 | 15.20 | 20.82 | 0.351 | 0.362 |

As shown in Table 3 and FIGS. 15A to 15D, in comparison to "Comparative Example 3", the driving voltage of the organic light emitting diode of the present invention (Ex 11 and Ex 12) is reduced (about 12%), the power efficiency of the organic light emitting diode of the present invention (Ex 11 and Ex 12) is improved (about 35%). In addition, the EQE of the organic light emitting diode of the present invention (Ex 11 and Ex 12) is improved (about 23%).

Namely, by using the organic compound of the present invention in the P-CGL and the second HTL, there are advantages in the driving voltage, the luminance, the power efficiency and/or the EQE.

As shown in "Example 1" to "Example 12" and "Comparative Example 1" to "Comparative Example 3", the organic light emitting diode including the organic compound of the present invention in at least one of the HTL and the EBL in the single stack structure and in at least one of HTL, the EML and the P-CGL in the tandem structure has advantages in the driving voltage, the power consumption, the power efficiency and the EQE and provide the full color image. In addition, the lifetime of the organic light emitting diode is also improved.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:
1. An organic compound, selected from the group consisting of:
H-01
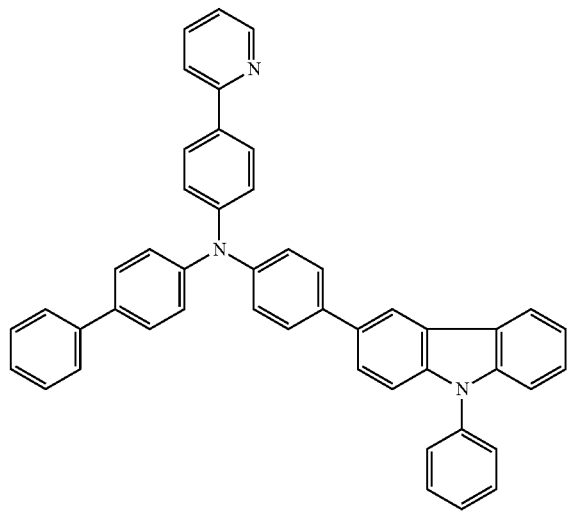
H-02
H-03
H-04
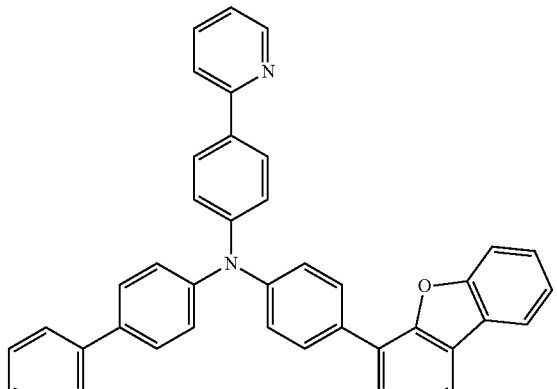
H-05
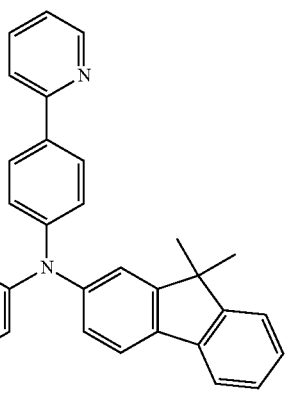
H-06
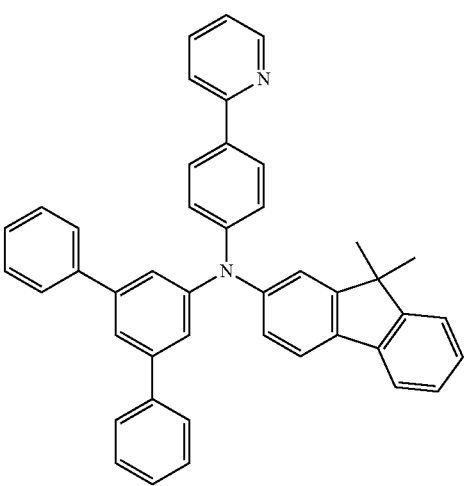

H-07
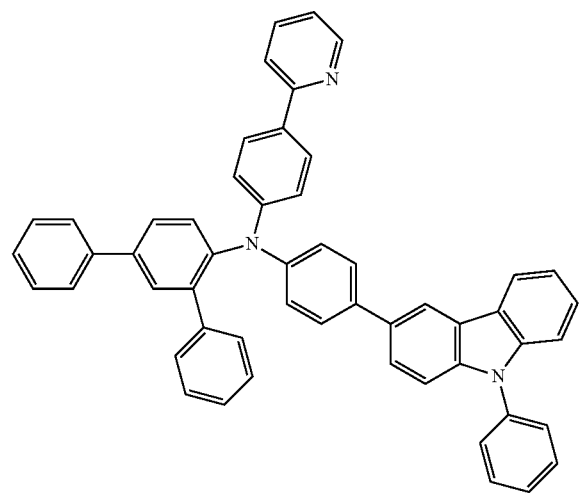
H-08
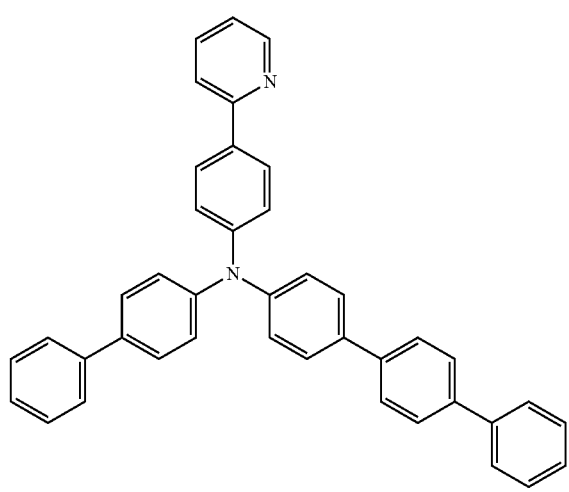
H-09
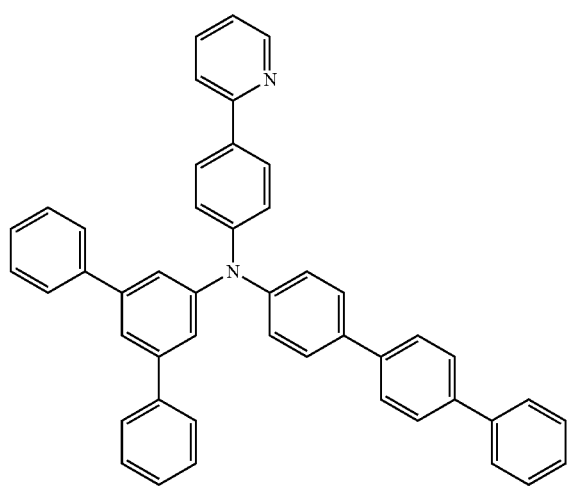
H-10
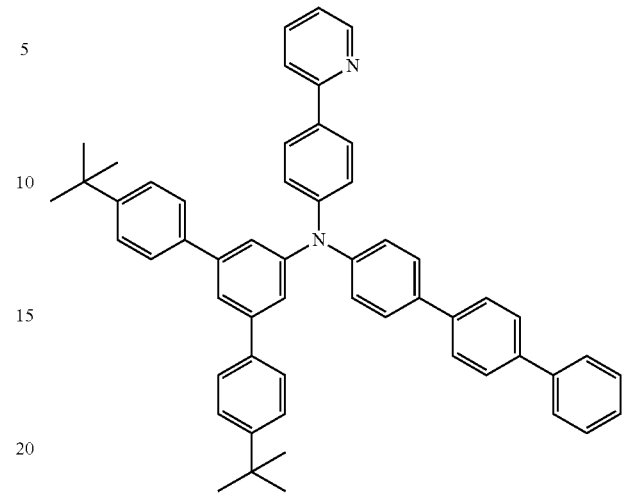
H-11
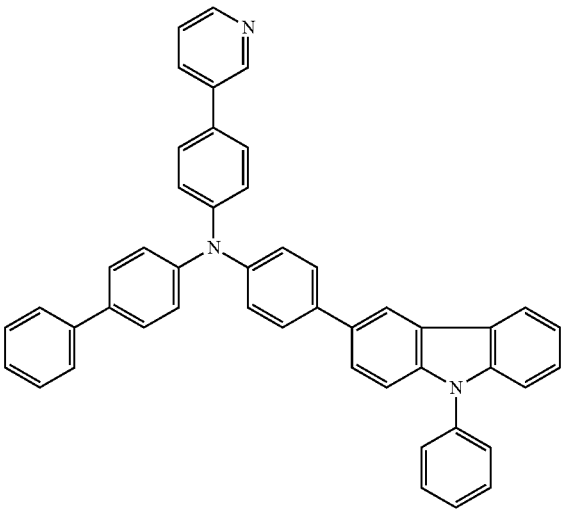
H-12
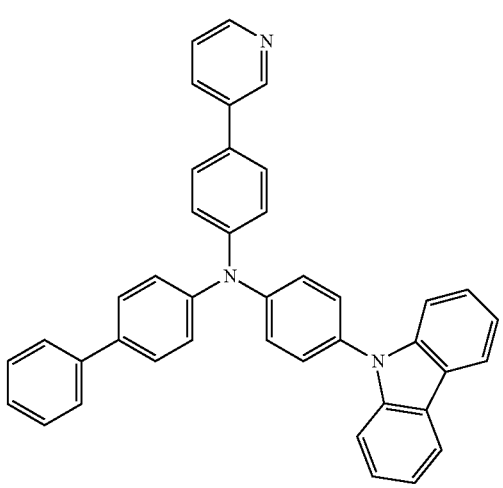

H-13
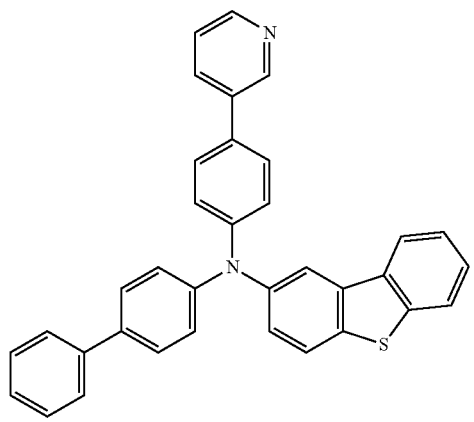
H-16
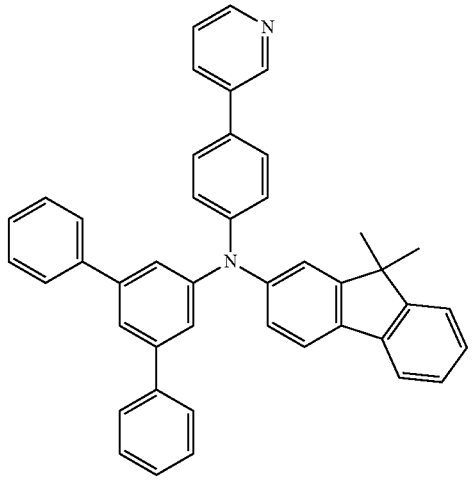
H-14
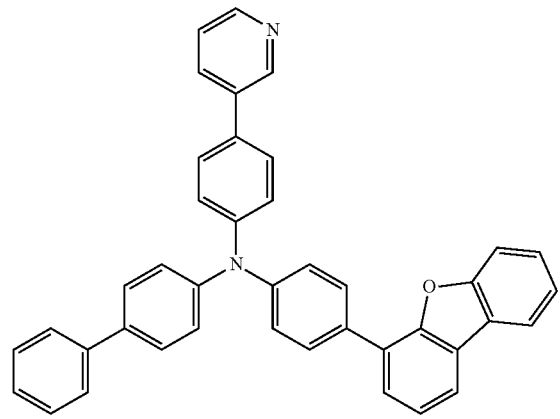
H-17
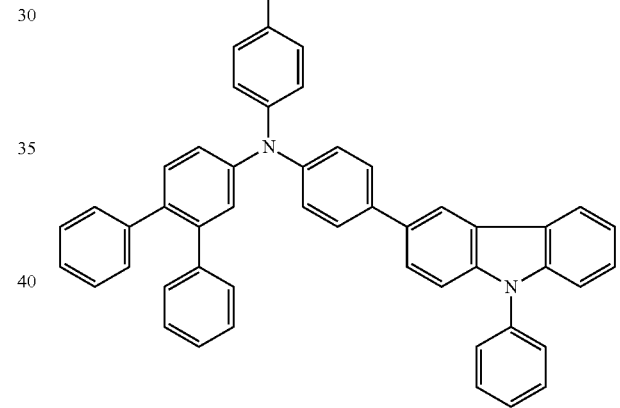
H-15
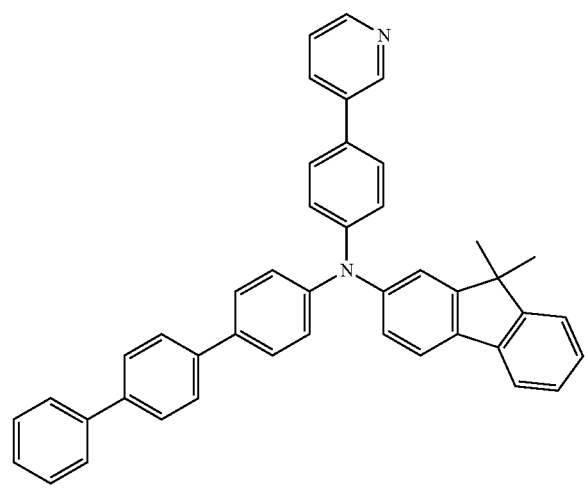
H-18
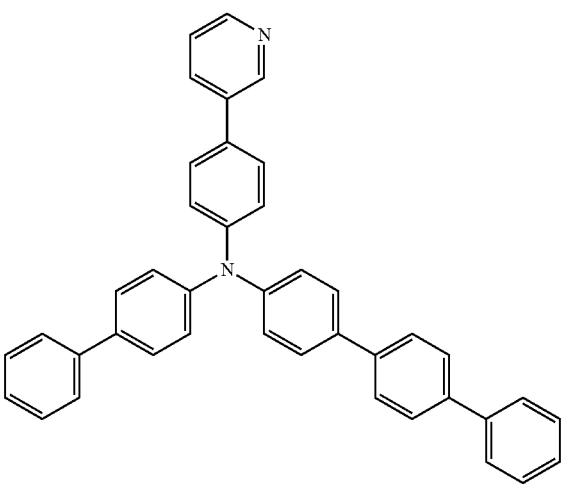

H-19
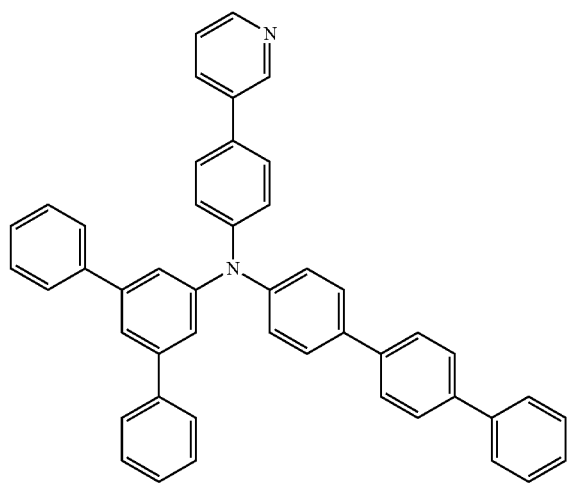
H-20
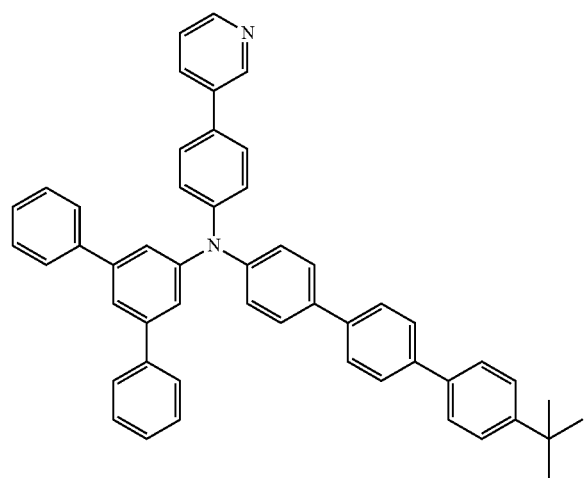
H-21
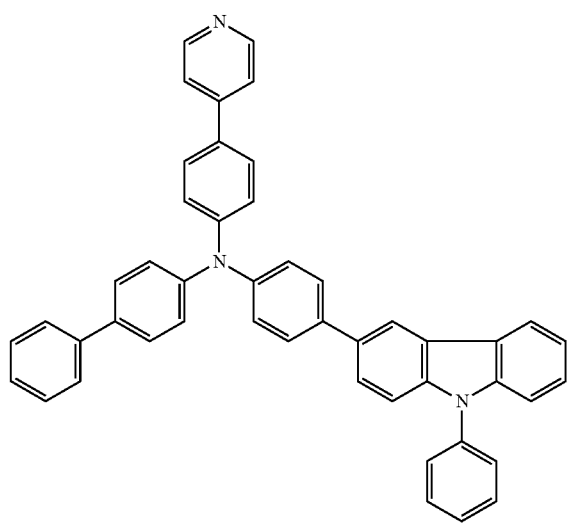
H-22
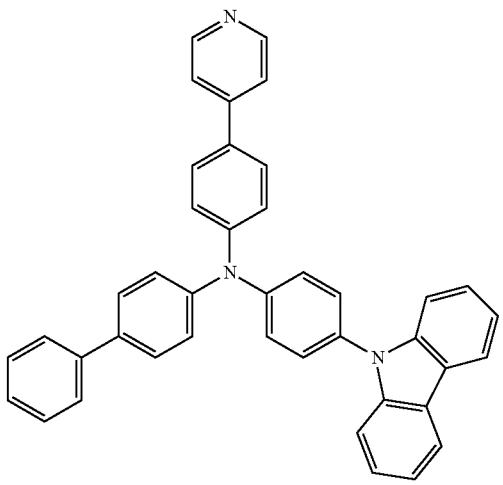
H-23
H-24
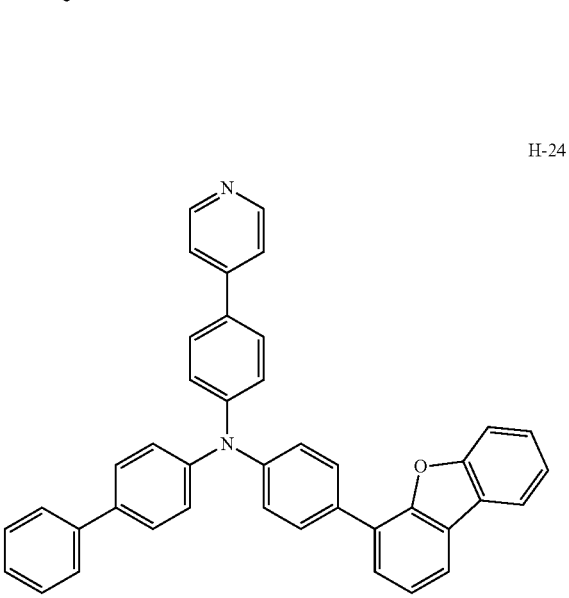

-continued
H-25
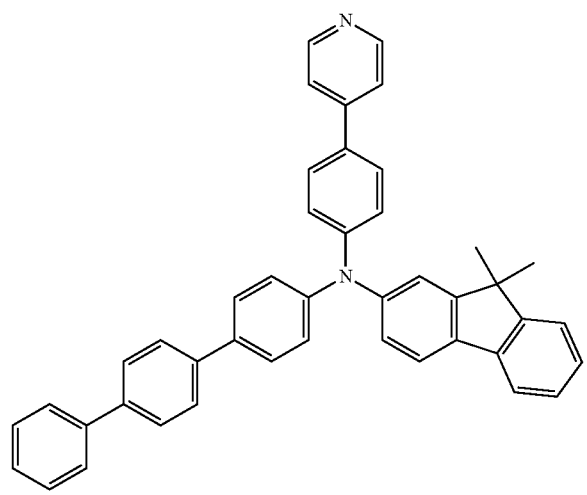
H-26
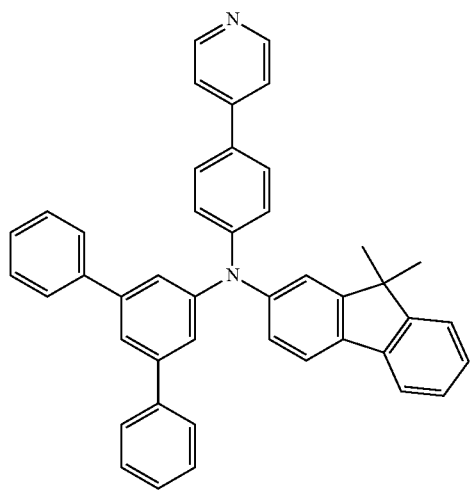
H-27
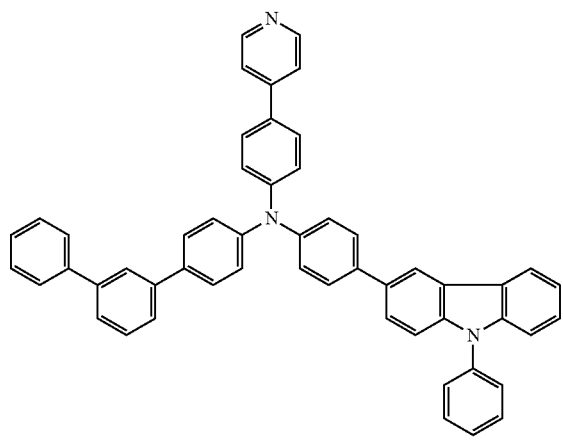
-continued
H-28
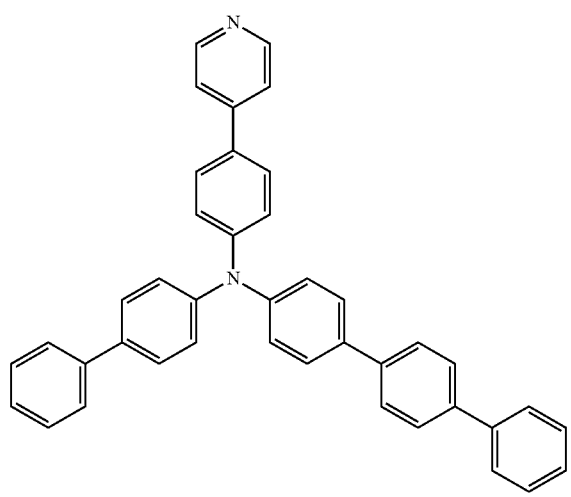
H-29
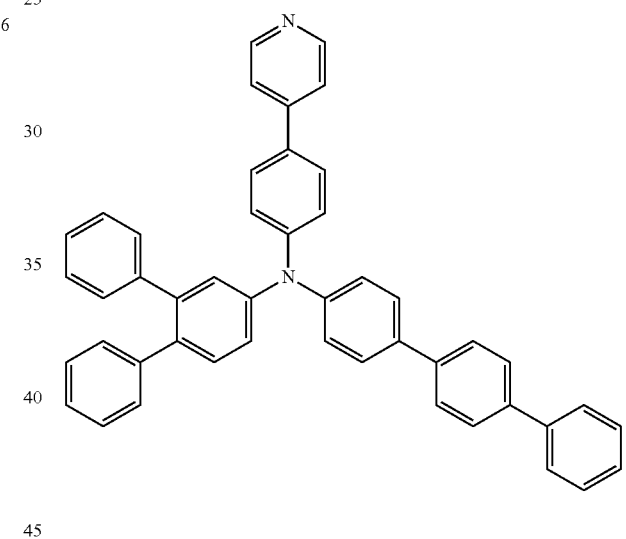
H-30
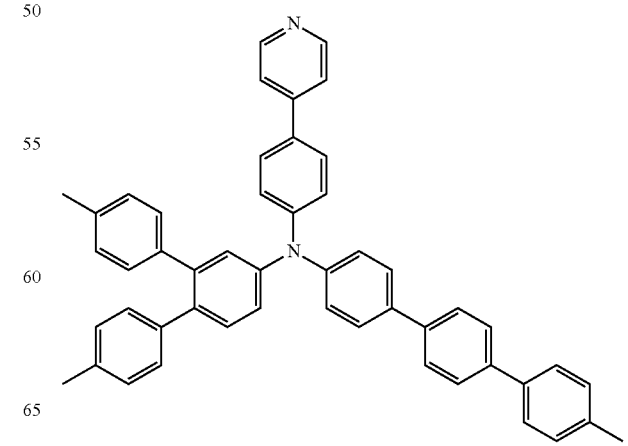

-continued
H-31
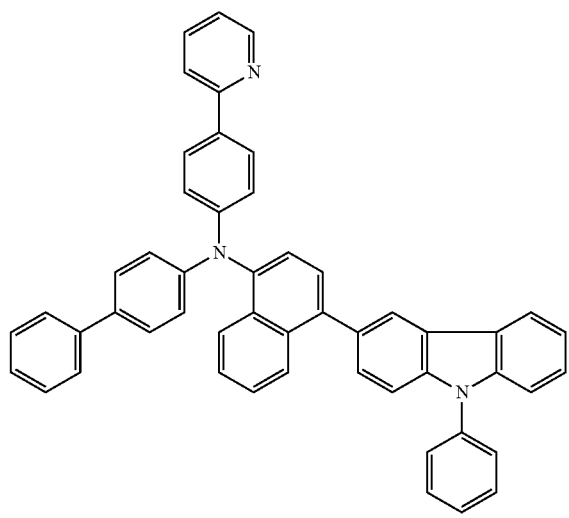
H-32
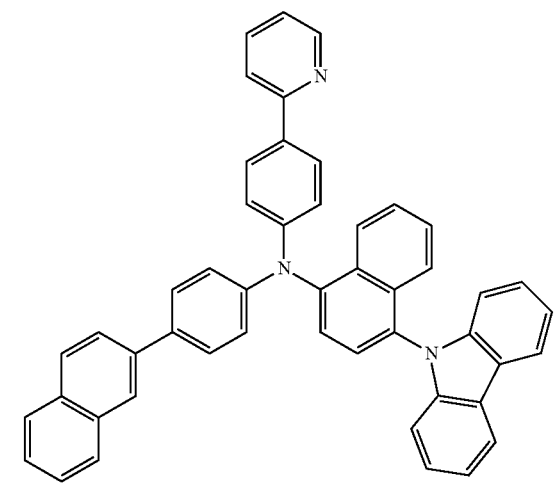
H-33
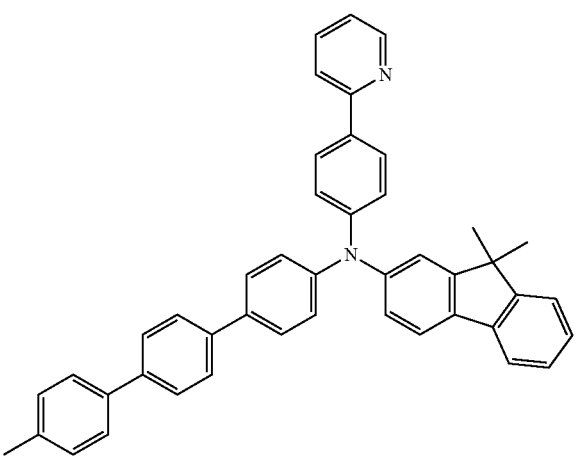
-continued
H-34
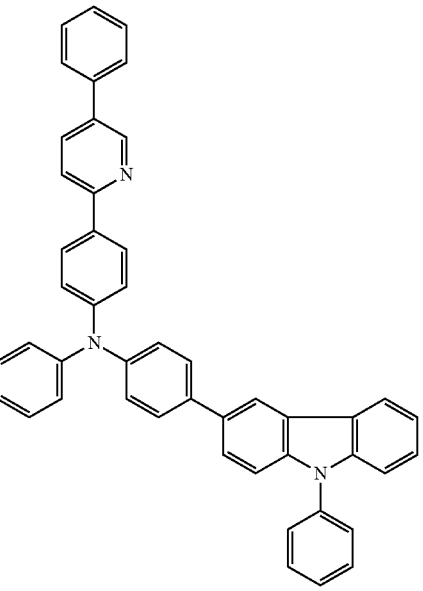
H-35
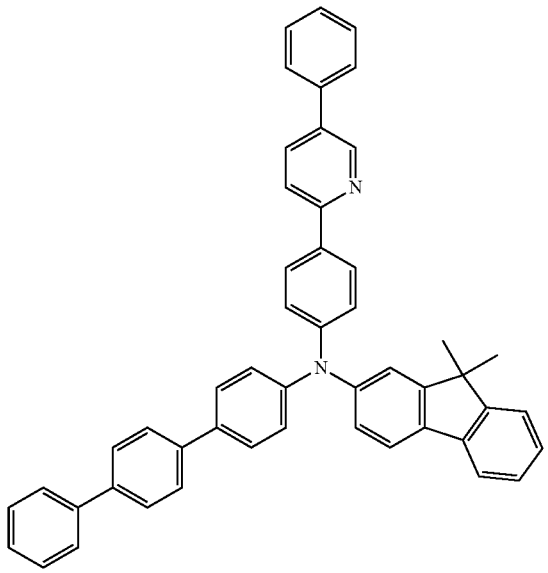

H-36
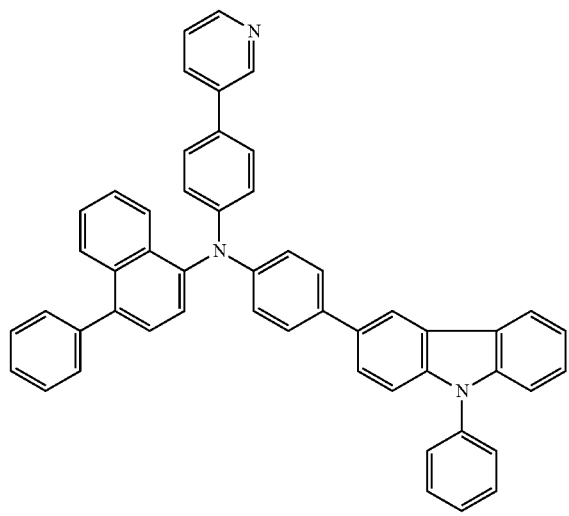
H-37
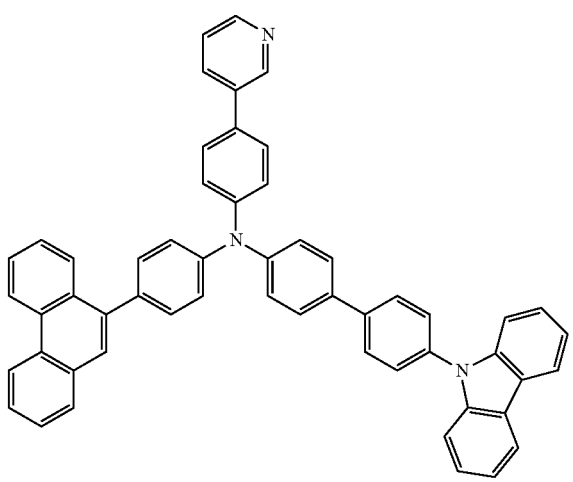
H-38
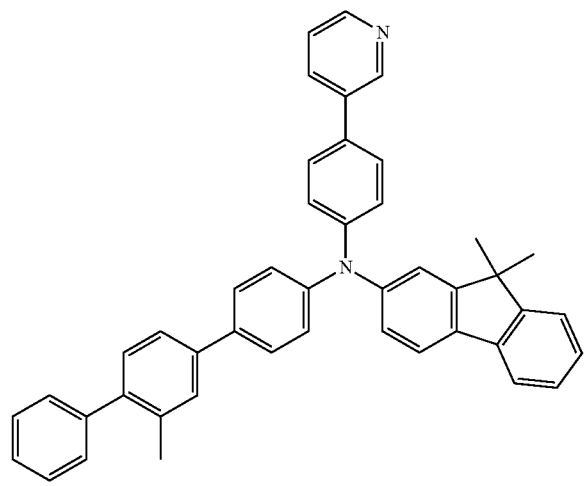
H-39
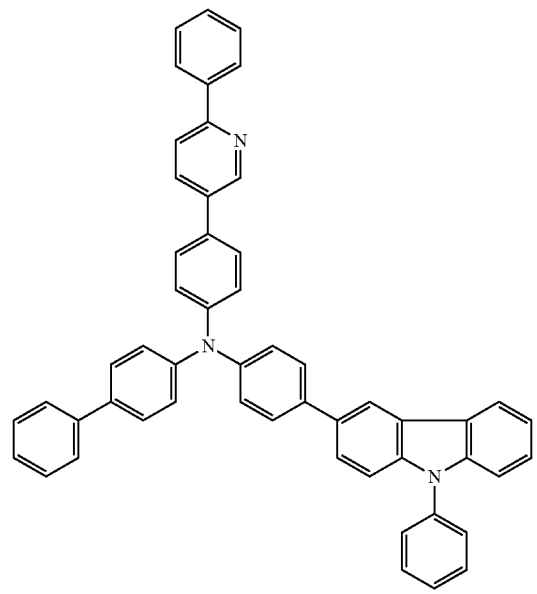
H-40
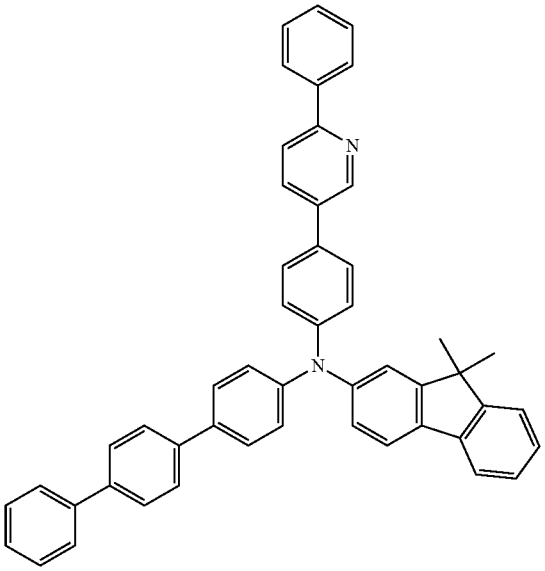

H-41
H-42
H-44
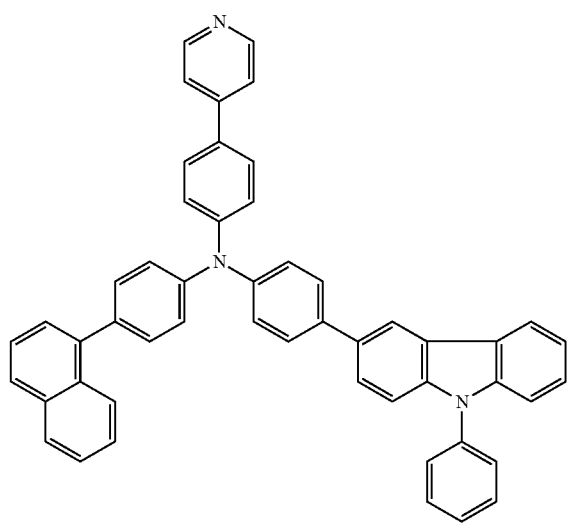
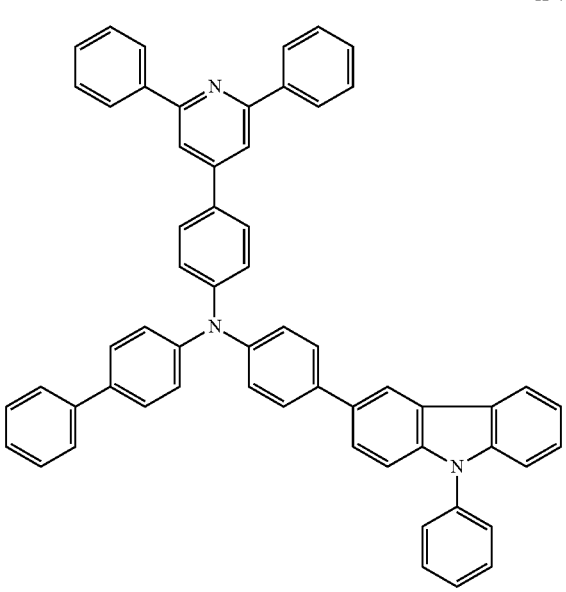
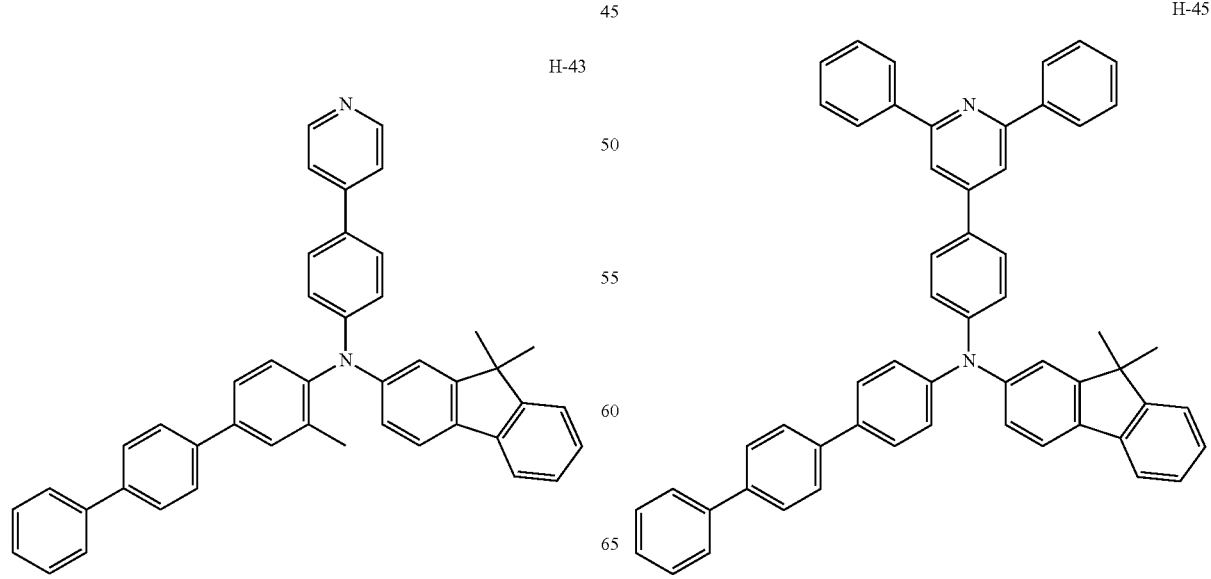
H-43
H-45

H-46
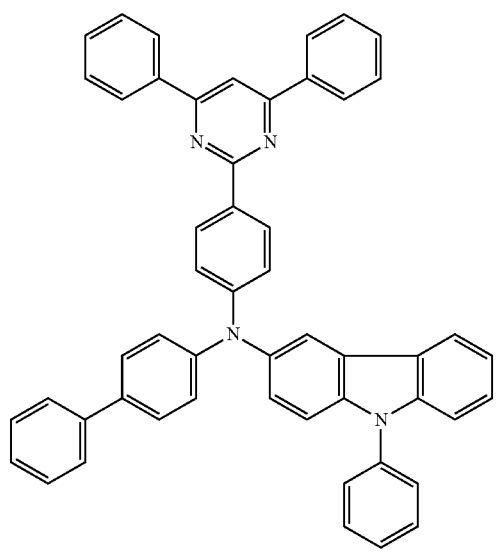
H-48
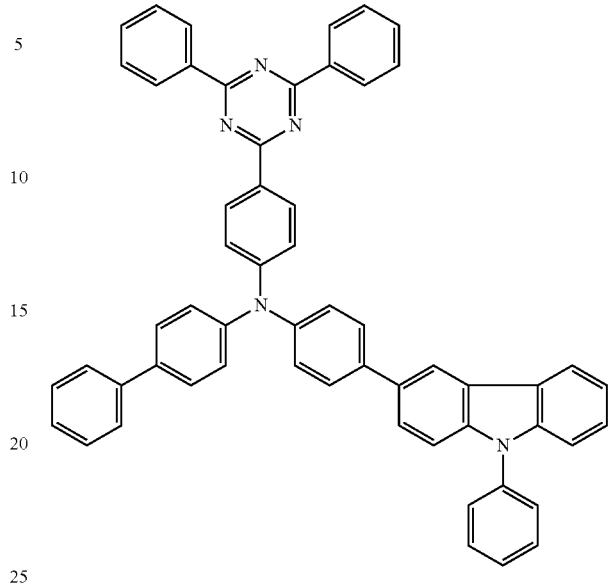
H-47
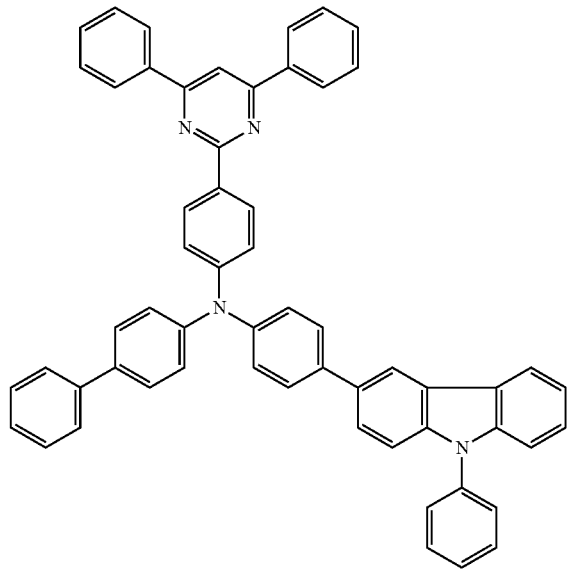
H-49

-continued

H-50

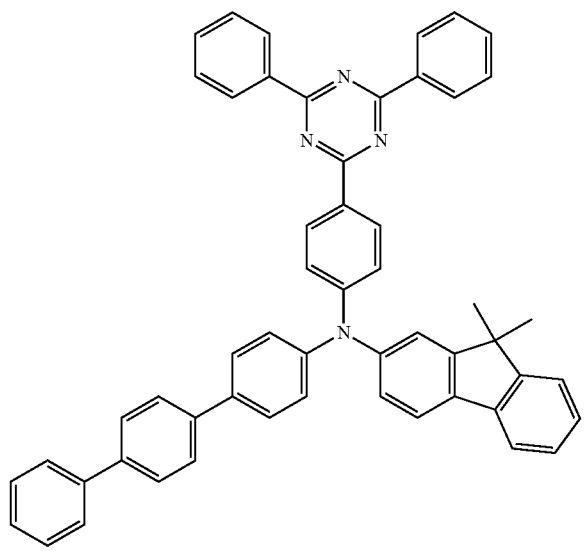

H-51

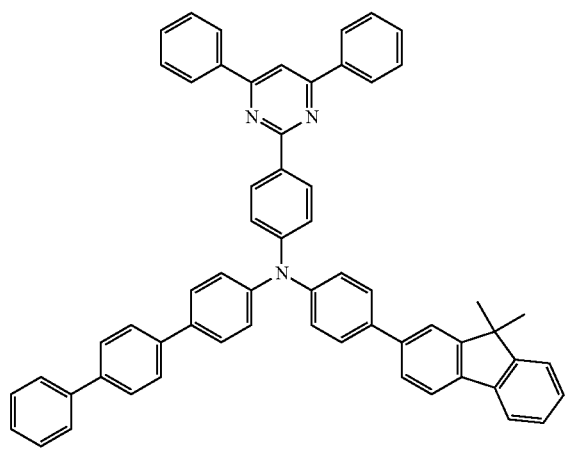

and

H-52

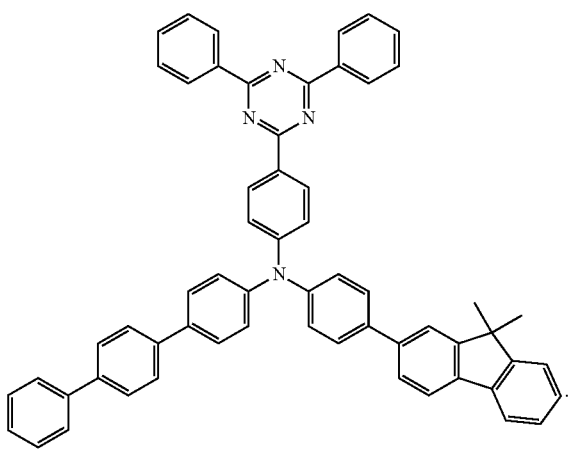

2. An organic light emitting diode, comprising:
a first electrode;
a second electrode facing the first electrode; and
an emitting part between the first electrode and the second electrode and including an emitting material layer and an organic layer, and
wherein the organic layer includes the organic compound of claim 1.

3. The organic light emitting diode according to claim 2, wherein the organic layer is a hole auxiliary layer including a hole injection layer and a hole transporting layer, and
wherein the hole transporting layer includes the organic compound with or without a hole transporting dopant.

4. The organic light emitting diode according to claim 2, wherein the organic layer is a hole auxiliary layer including a hole injection layer and a hole transporting layer, and the hole transporting layer includes a first layer between the hole injection layer and the emitting material layer and a second layer between the first layer and the emitting material layer, and
wherein the first layer includes the organic compound and the second layer includes the organic compound with a hole transporting dopant, or the second layer includes the organic compound and the first layer includes the organic compound with a hole transporting dopant.

5. The organic light emitting diode according to claim 2, wherein the organic layer includes a first hole transporting layer including the organic compound with a hole injection dopant, and the first hole transporting layer contacts the first electrode.

6. The organic light emitting diode according to claim 5, wherein the organic layer further includes a second hole transporting layer between the first hole transporting layer and the emitting material layer and including the organic compound with or without a hole transporting dopant.

7. The organic light emitting diode according to claim 5, wherein the organic layer includes a hole transporting layer and an electron blocking layer between the hole transporting layer and the emitting material layer, and the electron blocking layer includes the organic compound.

8. An organic light emitting display device, comprising:
a substrate;
the organic light emitting diode of claim 2: and
a thin film transistor between the substrate and the organic light emitting diode,
wherein the thin film transistor is connected to the organic light emitting diode.

9. An organic light emitting diode, comprising:
a first electrode and a second electrode facing each other;
a first emitting part between the first electrode and the second electrode and including a first emitting material layer;
a second emitting part between the first emitting part and the second electrode and including a second emitting material layer; and
a P-type charge generation layer between the first emitting part and the second emitting part,
wherein the P-type charge generation layer includes the organic compound of claim 1.

10. The organic light emitting diode according to claim 9, wherein the P-type charge generation layer further includes a hole injection dopant.

11. The organic light emitting diode according to claim 10, wherein the first emitting part includes a hole injection layer and a first hole transporting layer between the first electrode and the first emitting material layer and a first electron transporting layer between the first emitting material layer and the P-type charge generation layer, and the second emitting part further includes a second hole transporting layer between the P-type charge generation layer and the second electrode, a second electron transporting layer between the second emitting material layer and the second electrode and an electron injection layer between the second electron transporting layer and the second electrode.

12. The organic light emitting diode according to claim 11, wherein the second hole transporting layer includes the organic compound with or without a hole transporting dopant.

13. The organic light emitting diode according to claim 9, wherein the first emitting part includes a hole injection layer and a hole transporting layer between the first electrode and the first emitting material layer and a first electron transporting layer between the first emitting material layer and the P-type charge generation layer, and the second emitting part further includes a second electron transporting layer between the second emitting material layer and the second electrode and an electron injection layer between the second electron transporting layer and the second electrode, and wherein the P-type charge generation layer further includes a hole injection dopant.

14. An organic light emitting display device, comprising:
a substrate;
the organic light emitting diode of claim 9: and
a thin film transistor between the substrate and the organic light emitting diode,
wherein the thin film transistor is connected to the organic light emitting diode.

15. An organic light emitting diode, comprising:
a first electrode and a second electrode facing each other;
a first emitting part between the first electrode and the second electrode and including a first emitting material layer;
a second emitting part between the first emitting part and the second electrode and including a second emitting material layer; and
a charge generation layer between the first emitting part and the second emitting part,
wherein the second emitting part further includes an electron blocking layer between the charge generation layer and the second emitting material layer and including the organic compound of claim 1.

16. An organic light emitting display device, comprising:
a substrate;
the organic light emitting diode of claim 15: and
a thin film transistor between the substrate and the organic light emitting diode,
wherein the thin film transistor is connected to the organic light emitting diode.

17. An organic light emitting diode, comprising:
a first electrode and a second electrode facing each other;
a first emitting part between the first electrode and the second electrode and including a first emitting material layer, the first emitting part including a hole injection layer and a first hole transporting layer between the first electrode and the first emitting material layer and a first electron transporting layer between the first emitting material layer and a P-type charge generation layer;
a second emitting part between the first emitting part and the second electrode and including a second emitting material layer, the second emitting part further includes a second hole transporting layer between the P-type charge generation layer and the second electrode, a second electron transporting layer between the second emitting material layer and the second electrode and an electron injection layer between the second electron transporting layer and the second electrode;
a P-type charge generation layer between the first emitting part and the second emitting part;
an N-type charge generation layer between the P-type charge generation layer and the first electron transporting layer; and
an intermediate charge generation layer between the P-type charge generation layer and the N-type charge generation layer,
wherein the P-type charge generation layer includes the organic compound of claim 1 and a hole injection dopant, and
wherein the intermediate charge generation layer includes a hole injection material and the organic compound doped to the hole injection material.

* * * * *